US010752878B2

(12) United States Patent
Eyal et al.

(10) Patent No.: US 10,752,878 B2
(45) Date of Patent: Aug. 25, 2020

(54) SUGAR MIXTURES AND METHODS FOR PRODUCTION AND USE THEREOF

(71) Applicant: Virdia, Inc., Raceland, LA (US)

(72) Inventors: Aharon Meir Eyal, Jerusalem (IL); Robert P. Jansen, Collinsville, IL (US); Revital Mali, Jerusalem (IL); Asher Vitner, Jerusalem (IL)

(73) Assignee: VIRDIA, INC., Raceland, LA (US)

( * ) Notice: Subject to any disclaimer, the term of this patent is extended or adjusted under 35 U.S.C. 154(b) by 0 days.

(21) Appl. No.: 15/933,210

(22) Filed: Mar. 22, 2018

(65) Prior Publication Data

US 2019/0032005 A1    Jan. 31, 2019

Related U.S. Application Data

(63) Continuation of application No. 15/191,376, filed on Jun. 23, 2016, now Pat. No. 9,963,673, which is a (Continued)

(30) Foreign Application Priority Data

Jul. 8, 2010   (IL) ......................... 206896
Jul. 29, 2010  (IL) ......................... 207313

(51) Int. Cl.
*C12N 1/22* (2006.01)
*C12P 7/10* (2006.01)
(Continued)

(52) U.S. Cl.
CPC .............. *C12N 1/22* (2013.01); *C01B 7/0737* (2013.01); *C12P 7/10* (2013.01); *C12P 19/02* (2013.01);
(Continued)

(58) Field of Classification Search
CPC ........... C13K 1/02; C13K 3/00; C13K 13/002
See application file for complete search history.

(56) References Cited

U.S. PATENT DOCUMENTS 1,344,671 A   6/1920   Bergius
1,391,664 A   9/1921   Bergius
(Continued)

FOREIGN PATENT DOCUMENTS

CA   2735396 A1   3/2010
CN   101001952 A  7/2007
(Continued)

OTHER PUBLICATIONS

Barton. "Table 18 Hoy's Cohesion Parameters for liquids (and solids and subcooled liquids) at 25 ° C." in CRC Handboook of solubility parameters and other cohesion parameters, Second Edition, January 1, 1991. CRC Press, Boca Raton, FL. pp. 123-138.
(Continued)

*Primary Examiner* — Liam J Heincer
(74) *Attorney, Agent, or Firm* — Wilson Sonsini Goodrich & Rosati

(57) ABSTRACT

A sugar mixture comprising: monosaccharides; oligosaccharides in a ratio≥0.06 to total saccharides; disaccharides in a ratio to total saccharides≥0.05; pentose in a ratio to total saccharides≥0.05; at least one alpha-bonded di-glucose; and at least one beta-bonded di-glucose. Also disclosed are methods to make and/or use such mixtures.

19 Claims, 6 Drawing Sheets

Related U.S. Application Data continuation of application No. 13/378,657, filed as application No. PCT/IL2011/000509 on Jun. 26, 2011, now Pat. No. 9,410,216.

(60) Provisional application No. 61/358,894, filed on Jun. 26, 2010, provisional application No. 61/491,243, filed on May 30, 2011, provisional application No. 61/500,169, filed on Jun. 23, 2011.

(51) Int. Cl.

| | | |
|---|---|---|
| C12P 19/02 | (2006.01) | |
| C12P 19/14 | (2006.01) | |
| C01B 7/07 | (2006.01) | |
| C13K 1/02 | (2006.01) | |
| C13K 7/00 | (2006.01) | |
| C13K 13/00 | (2006.01) | |

(52) U.S. Cl.
CPC .............. *C12P 19/14* (2013.01); *C13K 1/02* (2013.01); *C13K 7/00* (2013.01); *C13K 13/00* (2013.01); *A23V 2002/00* (2013.01); *C12P 2203/00* (2013.01); *Y02E 50/13* (2013.01); *Y02E 50/16* (2013.01); *Y02E 50/17* (2013.01)

(56) References Cited

U.S. PATENT DOCUMENTS

| | | | |
|---|---|---|---|
| 1,457,791 | A | 6/1923 | Norris et al. |
| 1,544,149 | A | 6/1925 | Hagglund |
| 1,547,893 | A | 7/1925 | Bergius |
| 1,688,726 | A | 10/1928 | McKee |
| 1,699,177 | A | 1/1929 | Bergius |
| 1,853,330 | A | 4/1932 | Barstow et al. |
| 1,890,491 | A | 12/1932 | Bergius et al. |
| 1,906,467 | A | 5/1933 | Heath |
| 1,919,623 | A | 7/1933 | Dreyfus |
| 2,008,284 | A | 7/1935 | Koch et al. |
| 2,146,326 | A | 2/1939 | Bergius et al. |
| 2,239,095 | A | 4/1941 | Hasche |
| 2,293,724 | A | 8/1942 | Faerber |
| 2,305,833 | A | 12/1942 | Warth |
| 2,347,945 | A | 5/1944 | Frey |
| 2,380,448 | A | 7/1945 | Katzen |
| 2,391,149 | A | 12/1945 | Frey |
| 2,440,442 | A | 4/1948 | Hillyer et al. |
| 2,474,669 | A | 6/1949 | Hereng |
| 2,692,291 | A | 10/1954 | Bryan |
| 2,743,219 | A | 4/1956 | Riehm |
| 2,752,270 | A | 6/1956 | Specht |
| 2,778,751 | A | 1/1957 | Richm |
| 2,890,972 | A | 6/1959 | Wheaton |
| 2,917,390 | A | 12/1959 | Apel et al. |
| 2,937,959 | A | 5/1960 | Reents et al. |
| 2,944,923 | A | 7/1960 | Riehm |
| 2,945,777 | A | 7/1960 | Riehm |
| 2,951,775 | A | 9/1960 | Apel |
| 2,989,569 | A | 6/1961 | Apel |
| 3,067,065 | A | 12/1962 | Kusama |
| 3,132,051 | A | 5/1964 | Nobile et al. |
| 3,212,933 | A | 10/1965 | Hess et al. |
| 3,251,716 | A | 5/1966 | Porter |
| 3,311,450 | A | 3/1967 | Alon et al. |
| 3,326,944 | A | 6/1967 | Lew |
| 3,394,056 | A | 7/1968 | Nadler et al. |
| 3,432,569 | A | 3/1969 | John |
| 3,497,330 | A | 2/1970 | Avraham et al. |
| 3,527,820 | A | 9/1970 | Jules |
| 3,562,289 | A | 2/1971 | Orlando et al. |
| 3,697,497 | A | 10/1972 | Alfons |
| 3,808,192 | A | 4/1974 | Dimitri |
| 3,839,318 | A | 10/1974 | Mansfield |
| 4,008,285 | A | 2/1977 | Melaja et al. |
| 4,018,637 | A | 4/1977 | Kimmel et al. |
| 4,036,939 | A | 7/1977 | Duhayon et al. |
| 4,075,406 | A | 2/1978 | Melaja et al. |
| 4,102,705 | A | 7/1978 | Pfeiffer et al. |
| 4,111,928 | A | 9/1978 | Holsopple et al. |
| 4,115,530 | A | 9/1978 | Coenen et al. |
| 4,174,976 | A | 11/1979 | Bose et al. |
| 4,184,845 | A | 1/1980 | Lin |
| 4,206,302 | A | 6/1980 | Favrot et al. |
| 4,230,681 | A | 10/1980 | Coenen et al. |
| 4,237,110 | A | 12/1980 | Forster et al. |
| 4,255,356 | A | 3/1981 | Coenen et al. |
| 4,257,818 | A | 3/1981 | Regnault et al. |
| 4,259,309 | A | 3/1981 | Coenen et al. |
| 4,272,502 | A | 6/1981 | Ziegenbein et al. |
| 4,277,626 | A | 7/1981 | Forss et al. |
| 4,278,471 | A | 7/1981 | Whittingham |
| 4,291,007 | A | 9/1981 | Baniel |
| 4,299,677 | A | 11/1981 | Venkatasubramanian et al. |
| 4,304,608 | A | 12/1981 | Regnault et al. |
| 4,328,004 | A | 5/1982 | Globus |
| 4,374,738 | A | 2/1983 | Kelley |
| 4,382,843 | A | 5/1983 | Black |
| 4,384,897 | A | 5/1983 | Brink |
| 4,420,644 | A | 12/1983 | Huibers et al. |
| 4,425,136 | A | 1/1984 | Pearson et al. |
| 4,470,851 | A | 9/1984 | Paszner et al. |
| 4,472,501 | A | 9/1984 | Takasawa et al. |
| 4,516,566 | A | 5/1985 | Chao et al. |
| 4,520,105 | A | 5/1985 | Sinner et al. |
| 4,533,743 | A | 8/1985 | Medeiros et al. |
| 4,556,432 | A | 12/1985 | Erckel et al. |
| 4,579,595 | A | 4/1986 | Sachetto et al. |
| 4,608,245 | A | 8/1986 | Gaddy et al. |
| 4,612,286 | A | 9/1986 | Sherman et al. |
| 4,615,742 | A | 10/1986 | Wright |
| 4,631,129 | A | 12/1986 | Heikkila |
| 4,645,658 | A | 2/1987 | Gaddy et al. |
| 4,647,704 | A | 3/1987 | Engel et al. |
| 4,668,340 | A | 5/1987 | Sherman |
| 4,677,198 | A | 6/1987 | Linnett et al. |
| 4,701,414 | A | 10/1987 | Van et al. |
| 4,713,413 | A | 12/1987 | Tegge et al. |
| 4,764,597 | A | 8/1988 | Dilling |
| 4,814,015 | A | 3/1989 | Quinlan |
| 4,837,315 | A | 6/1989 | Kulprathipanja |
| 4,840,903 | A | 6/1989 | Wu |
| 4,901,635 | A | 2/1990 | Williams |
| 4,934,177 | A | 6/1990 | Cuthbertson et al. |
| 4,946,946 | A | 8/1990 | Fields et al. |
| 4,958,016 | A | 9/1990 | Kerkenaar et al. |
| 4,966,650 | A | 10/1990 | Delong et al. |
| 4,990,696 | A | 2/1991 | Stauffer |
| 5,028,336 | A | 7/1991 | Bartels et al. |
| 5,049,494 | A | 9/1991 | Allenza |
| 5,081,026 | A | 1/1992 | Heikkilae et al. |
| 5,084,104 | A | 1/1992 | Heikkila et al. |
| 5,093,004 | A | 3/1992 | Hotier et al. |
| 5,114,491 | A | 5/1992 | Sarhaddar |
| 5,114,590 | A | 5/1992 | Hotier et al. |
| 5,132,476 | A | 7/1992 | Osterburg et al. |
| 5,138,110 | A | 8/1992 | Segall et al. |
| 5,174,865 | A | 12/1992 | Stultz et al. |
| 5,176,832 | A | 1/1993 | Dorta et al. |
| 5,188,673 | A | 2/1993 | Clausen et al. |
| 5,196,460 | A | 3/1993 | Lora et al. |
| 5,205,473 | A | 4/1993 | Coffin, Sr. |
| 5,227,446 | A | 7/1993 | Denzinger et al. |
| 5,238,826 | A | 8/1993 | Leleu et al. |
| 5,244,553 | A | 9/1993 | Goldstein |
| 5,332,842 | A | 7/1994 | Dickakian |
| 5,338,405 | A | 8/1994 | Patt et al. |
| 5,357,035 | A | 10/1994 | Gruber et al. |
| 5,407,580 | A | 4/1995 | Hester et al. |
| 5,411,594 | A | 5/1995 | Brelsford |
| 5,421,964 | A | 6/1995 | Mahler et al. |
| 5,480,490 | A | 1/1996 | Toth et al. |
| 5,538,637 | A | 7/1996 | Hester et al. |
| 5,571,378 | A | 11/1996 | Elofson et al. |
| 5,580,389 | A | 12/1996 | Farone et al. |

(56) References Cited

U.S. PATENT DOCUMENTS

| | | |
|---|---|---|
| 5,597,714 A | 1/1997 | Farone et al. |
| 5,602,286 A | 2/1997 | Muralidhara |
| 5,637,225 A | 6/1997 | Heikkilae et al. |
| 5,696,195 A | 12/1997 | Tuminello et al. |
| 5,698,667 A | 12/1997 | Speaks et al. |
| 5,705,369 A | 1/1998 | Torget et al. |
| 5,723,704 A | 3/1998 | Demail et al. |
| 5,726,046 A | 3/1998 | Farone et al. |
| 5,730,837 A | 3/1998 | Black et al. |
| 5,730,877 A | 3/1998 | Heikkilae et al. |
| 5,767,330 A | 6/1998 | Metz et al. |
| 5,782,982 A | 7/1998 | Farone et al. |
| 5,807,952 A | 9/1998 | Agblevor |
| 5,820,687 A | 10/1998 | Farone et al. |
| 5,837,831 A | 11/1998 | Gruening et al. |
| 5,847,238 A | 12/1998 | Muralidhara et al. |
| 5,859,270 A | 1/1999 | Kolstad et al. |
| 5,865,948 A | 2/1999 | Lora et al. |
| 5,876,505 A | 3/1999 | Klyosov et al. |
| 5,959,128 A | 9/1999 | Kolstad et al. |
| 5,969,195 A | 10/1999 | Stabel et al. |
| 5,980,593 A | 11/1999 | Friswell et al. |
| 5,998,607 A | 12/1999 | Heikkilae et al. |
| 6,001,410 A | 12/1999 | Bolen et al. |
| 6,007,636 A | 12/1999 | Lightner |
| 6,086,681 A | 7/2000 | Lindroos et al. |
| 6,093,217 A | 7/2000 | Froelich et al. |
| 6,136,078 A | 10/2000 | Craig |
| 6,172,204 B1 | 1/2001 | Sarkanen et al. |
| 6,207,209 B1 | 3/2001 | Jirjis et al. |
| 6,224,776 B1 | 5/2001 | Heikkilä et al. |
| 6,229,046 B1 | 5/2001 | Eyal et al. |
| 6,230,477 B1 | 5/2001 | Caillouet |
| 6,239,274 B1 | 5/2001 | Heikkilä et al. |
| 6,258,175 B1 | 7/2001 | Lightner |
| 6,262,318 B1 | 7/2001 | Heikkilä et al. |
| 6,352,845 B1 | 3/2002 | Buchanan et al. |
| 6,391,204 B1 | 5/2002 | Russo, Jr. |
| 6,409,841 B1 | 6/2002 | Lombard |
| 6,416,621 B1 | 7/2002 | Karstens |
| 6,419,788 B1 | 7/2002 | Wingerson |
| 6,419,828 B1 | 7/2002 | Russo, Jr. |
| 6,431,370 B1 | 8/2002 | Braunstein et al. |
| 6,451,123 B1 | 9/2002 | Saska et al. |
| 6,452,051 B1 | 9/2002 | Eyal |
| 6,512,110 B1 | 1/2003 | Heikkila et al. |
| 6,548,662 B1 | 4/2003 | Ohsaki et al. |
| 6,572,775 B2 | 6/2003 | Heikkila et al. |
| 6,610,867 B2 | 8/2003 | Jakel et al. |
| 6,620,292 B2 | 9/2003 | Wingerson |
| 6,663,780 B2 | 12/2003 | Heikkila et al. |
| 6,692,578 B2 | 2/2004 | Schmidt et al. |
| 6,699,457 B2 | 3/2004 | Cortright et al. |
| 6,719,957 B2 | 4/2004 | Brady et al. |
| 6,747,076 B2 | 6/2004 | Schneider et al. |
| 6,752,902 B2 | 6/2004 | Heikkila et al. |
| 6,824,599 B2 | 11/2004 | Swatloski et al. |
| 6,833,149 B2 | 12/2004 | Jirjis et al. |
| 6,846,657 B2 | 1/2005 | Heikkila et al. |
| 6,852,345 B2 | 2/2005 | Hill et al. |
| 6,875,349 B2 | 4/2005 | Heikkila et al. |
| 6,896,811 B2 | 5/2005 | Heikkila et al. |
| 6,911,565 B2 | 6/2005 | Heikkila et al. |
| 6,924,371 B2 | 8/2005 | Karki et al. |
| 6,936,110 B2 | 8/2005 | Thorre et al. |
| 6,942,754 B2 | 9/2005 | Izumi et al. |
| 6,953,873 B2 | 10/2005 | Cortright et al. |
| 6,964,757 B2 | 11/2005 | Cortright et al. |
| 6,964,758 B2 | 11/2005 | Cortright et al. |
| 6,987,183 B2 | 1/2006 | Heikkila et al. |
| 7,022,239 B2 | 4/2006 | Heikkila et al. |
| 7,026,152 B2 | 4/2006 | Ingram et al. |
| 7,037,378 B2 | 5/2006 | Jumppanen et al. |
| 7,109,005 B2 | 9/2006 | Eroma et al. |
| 7,198,925 B2 | 4/2007 | Foody |
| 7,208,570 B2 | 4/2007 | Saviainen |
| 7,229,558 B2 | 6/2007 | Heikkila et al. |
| 7,314,528 B2 | 1/2008 | Koivikko et al. |
| 7,361,273 B2 | 4/2008 | Heikkila et al. |
| 7,399,323 B2 | 7/2008 | Renninger et al. |
| 7,449,313 B2 | 11/2008 | Rush |
| 7,465,791 B1 | 12/2008 | Hallberg et al. |
| 7,498,430 B2 | 3/2009 | Hollingsworth |
| 7,501,025 B2 | 3/2009 | Bakker et al. |
| 7,503,981 B2 | 3/2009 | Wyman et al. |
| 7,514,247 B2 | 4/2009 | Rush |
| 7,524,660 B2 | 4/2009 | Caimi et al. |
| 7,578,927 B2 | 8/2009 | Marker et al. |
| 7,618,612 B2 | 11/2009 | Cortright et al. |
| 7,625,728 B2 | 12/2009 | Eroma et al. |
| 7,629,010 B2 | 12/2009 | Passarelli et al. |
| 7,649,086 B2 | 1/2010 | Belanger et al. |
| 7,652,180 B2 | 1/2010 | Osterholt et al. |
| 7,662,617 B2 | 2/2010 | Rush |
| 7,670,813 B2 | 3/2010 | Foody et al. |
| 7,678,358 B2 | 3/2010 | Eckert et al. |
| 7,699,958 B2 | 4/2010 | Griffith et al. |
| 7,713,725 B2 | 5/2010 | England et al. |
| 7,717,364 B2 | 5/2010 | Wingerson |
| 7,718,070 B2 | 5/2010 | Wahnon et al. |
| 7,771,964 B2 | 8/2010 | Kim et al. |
| 7,794,824 B2 | 9/2010 | Eckert et al. |
| 7,834,092 B2 | 11/2010 | Uradnisheck et al. |
| 7,883,882 B2 | 2/2011 | Franklin et al. |
| 7,901,511 B2 | 3/2011 | Griffin et al. |
| 7,959,811 B2 | 6/2011 | Airaksinen et al. |
| 7,993,709 B2 | 8/2011 | Brunet |
| 8,003,352 B2 | 8/2011 | Foody et al. |
| 8,022,260 B2 | 9/2011 | O'Connor et al. |
| 8,101,808 B2 | 1/2012 | Evanko et al. |
| 8,163,092 B2 | 4/2012 | Baniel et al. |
| 8,247,203 B2 | 8/2012 | Foody et al. |
| 8,314,267 B2 | 11/2012 | Brandvold |
| 8,382,905 B2 | 2/2013 | Takeshima et al. |
| 8,404,355 B2 | 3/2013 | Jansen et al. |
| 8,604,225 B2 | 12/2013 | Pedersen et al. |
| 8,637,660 B2 | 1/2014 | Fanselow et al. |
| 8,637,661 B2 | 1/2014 | Fanselow et al. |
| 8,722,878 B2 | 5/2014 | Raines et al. |
| 8,894,771 B2 | 11/2014 | Floyd et al. |
| 8,926,794 B2 | 1/2015 | Han et al. |
| 8,932,467 B2 | 1/2015 | Fosbol et al. |
| 9,115,467 B2 | 8/2015 | Jansen et al. |
| 9,410,216 B2 | 8/2016 | Eyal et al. |
| 9,476,106 B2 | 10/2016 | Eyal et al. |
| 9,512,495 B2 | 12/2016 | Eyal |
| 9,617,608 B2 | 4/2017 | Eyal et al. |
| 9,650,687 B2 | 5/2017 | Jansen et al. |
| 9,663,836 B2 | 5/2017 | Jansen et al. |
| 9,765,478 B2 | 9/2017 | Brandt et al. |
| 9,845,514 B2 | 12/2017 | Eyal et al. |
| 9,963,673 B2 | 5/2018 | Eyal et al. |
| 9,976,194 B2 | 5/2018 | Eyal et al. |
| 10,041,138 B1 | 8/2018 | Eyal et al. |
| 10,240,217 B2 | 3/2019 | Jansen et al. |
| 2001/0003797 A1 | 6/2001 | Guevara et al. |
| 2002/0061950 A1 | 5/2002 | Yamamoto et al. |
| 2002/0153317 A1 | 10/2002 | Heikkila et al. |
| 2002/0164731 A1 | 11/2002 | Eroma et al. |
| 2003/0013606 A1 | 1/2003 | Hampden-Smith et al. |
| 2003/0094416 A1 | 5/2003 | Heikkila et al. |
| 2003/0121516 A1 | 7/2003 | Hyoeky et al. |
| 2003/0156970 A1 | 8/2003 | Oberkofler et al. |
| 2003/0222021 A1 | 12/2003 | Ennelin et al. |
| 2004/0060673 A1 | 4/2004 | Phillips et al. |
| 2004/0074217 A1 | 4/2004 | Reaux |
| 2004/0108085 A1 | 6/2004 | Kettenbach et al. |
| 2004/0121446 A1 | 6/2004 | England et al. |
| 2004/0127371 A1 | 7/2004 | Arrowsmith et al. |
| 2004/0173533 A1 | 9/2004 | Farone et al. |
| 2004/0199025 A1 | 10/2004 | Stauffer |
| 2004/0199049 A1 | 10/2004 | Parasher et al. |
| 2004/0231661 A1 | 11/2004 | Griffin et al. |
| 2004/0237499 A1 | 12/2004 | Yogev et al. |

(56) References Cited

U.S. PATENT DOCUMENTS

| | | |
|---|---|---|
| 2005/0034823 A1 | 2/2005 | Brelid et al. |
| 2005/0136520 A1 | 6/2005 | Kinley et al. |
| 2005/0148056 A1 | 7/2005 | Levine et al. |
| 2005/0176110 A1 | 8/2005 | Leisola et al. |
| 2005/0211239 A1 | 9/2005 | Koivikko et al. |
| 2006/0024801 A1 | 2/2006 | Holtzapple et al. |
| 2006/0041059 A1 | 2/2006 | Fukasawa et al. |
| 2006/0051812 A1 | 3/2006 | Helin et al. |
| 2006/0134308 A1 | 6/2006 | Inglett |
| 2006/0207734 A1 | 9/2006 | Day et al. |
| 2007/0020375 A1 | 1/2007 | Jansen et al. |
| 2007/0031953 A1 | 2/2007 | Dunson et al. |
| 2007/0053987 A1 | 3/2007 | Bayer et al. |
| 2007/0112187 A1 | 5/2007 | Heikkila et al. |
| 2007/0178569 A1 | 8/2007 | Leschine et al. |
| 2007/0184555 A1 | 8/2007 | Banavali et al. |
| 2007/0197363 A1 | 8/2007 | Parrotta et al. |
| 2007/0219521 A1 | 9/2007 | Hird et al. |
| 2008/0021155 A1 | 1/2008 | Bono et al. |
| 2008/0029233 A1 | 2/2008 | Wingerson et al. |
| 2008/0032344 A1 | 2/2008 | Fallavollita |
| 2008/0033187 A1 | 2/2008 | Zhao et al. |
| 2008/0033188 A1 | 2/2008 | Dumesic et al. |
| 2008/0041366 A1 | 2/2008 | Wahnon et al. |
| 2008/0050792 A1 | 2/2008 | Zmierczak et al. |
| 2008/0053870 A1 | 3/2008 | Marker et al. |
| 2008/0057555 A1 | 3/2008 | Nguyen |
| 2008/0060638 A1 | 3/2008 | Koivikko et al. |
| 2008/0168982 A1 | 7/2008 | Vente et al. |
| 2008/0182305 A1 | 7/2008 | Foody et al. |
| 2008/0193992 A1 | 8/2008 | Levine |
| 2008/0202504 A1 | 8/2008 | Hilst |
| 2008/0216391 A1 | 9/2008 | Cortright et al. |
| 2008/0227161 A1 | 9/2008 | Levie et al. |
| 2008/0274509 A1 | 11/2008 | Filho et al. |
| 2008/0274528 A1 | 11/2008 | Dixon et al. |
| 2008/0299606 A1 | 12/2008 | Pompejus et al. |
| 2008/0300434 A1 | 12/2008 | Cortright et al. |
| 2008/0300435 A1 | 12/2008 | Cortright et al. |
| 2008/0305210 A1 | 12/2008 | Petersen |
| 2008/0317661 A1 | 12/2008 | Eckert et al. |
| 2008/0318043 A1 | 12/2008 | Eckert et al. |
| 2009/0053783 A1 | 2/2009 | Gokarn et al. |
| 2009/0056889 A1 | 3/2009 | Ren et al. |
| 2009/0061486 A1 | 3/2009 | Edwards et al. |
| 2009/0061495 A1 | 3/2009 | Beatty et al. |
| 2009/0062232 A1 | 3/2009 | Fujikawa et al. |
| 2009/0069550 A1 | 3/2009 | Belanger et al. |
| 2009/0084511 A1 | 4/2009 | Lampinen et al. |
| 2009/0124829 A1 | 5/2009 | Gong |
| 2009/0142848 A1 | 6/2009 | Wyman et al. |
| 2009/0155873 A1 | 6/2009 | Kashiyama et al. |
| 2009/0173339 A1 | 7/2009 | Heikkilae et al. |
| 2009/0176286 A1 | 7/2009 | O'Connor et al. |
| 2009/0218055 A1 | 9/2009 | Uusitalo et al. |
| 2009/0226979 A1 | 9/2009 | Retsina et al. |
| 2009/0226993 A1 | 9/2009 | Kumar et al. |
| 2009/0229599 A1 | 9/2009 | Zhang et al. |
| 2009/0234142 A1 | 9/2009 | Mascal |
| 2009/0286295 A1 | 11/2009 | Medoff et al. |
| 2009/0305942 A1 | 12/2009 | Day et al. |
| 2010/0009408 A1 | 1/2010 | England et al. |
| 2010/0012010 A1 | 1/2010 | Gooijer et al. |
| 2010/0024807 A1 | 2/2010 | Burke et al. |
| 2010/0028557 A1 | 2/2010 | Nagano |
| 2010/0043782 A1 | 2/2010 | Kilambi et al. |
| 2010/0043784 A1 | 2/2010 | Jensen |
| 2010/0048884 A1 | 2/2010 | Kilambi |
| 2010/0048924 A1 | 2/2010 | Kilambi |
| 2010/0069626 A1 | 3/2010 | Kilambi |
| 2010/0083565 A1 | 4/2010 | Gruter et al. |
| 2010/0086981 A1 | 4/2010 | Latouf et al. |
| 2010/0093995 A1 | 4/2010 | Baniel et al. |
| 2010/0116267 A1 | 5/2010 | Mraz et al. |
| 2010/0124772 A1 | 5/2010 | Sabesan |
| 2010/0136642 A1 | 6/2010 | Belanger et al. |
| 2010/0144001 A1 | 6/2010 | Horton |
| 2010/0146844 A1 | 6/2010 | Dumenil |
| 2010/0151527 A1 | 6/2010 | Endo et al. |
| 2010/0151535 A1 | 6/2010 | Franklin et al. |
| 2010/0152509 A1 | 6/2010 | Ekman |
| 2010/0159566 A1 | 6/2010 | Leschine et al. |
| 2010/0160624 A1 | 6/2010 | Cunningham |
| 2010/0167351 A1 | 7/2010 | Eyal et al. |
| 2010/0170504 A1 | 7/2010 | Zhang |
| 2010/0184151 A1 | 7/2010 | Tolan et al. |
| 2010/0184176 A1 | 7/2010 | Ishida et al. |
| 2010/0189706 A1 | 7/2010 | Chang et al. |
| 2010/0196979 A1 | 8/2010 | Birkmire et al. |
| 2010/0213130 A1 | 8/2010 | Airaksinen et al. |
| 2010/0233761 A1 | 9/2010 | Czartoski et al. |
| 2010/0249390 A1 | 9/2010 | Azuma et al. |
| 2010/0255554 A1 | 10/2010 | Benson et al. |
| 2010/0268000 A1 | 10/2010 | Parekh et al. |
| 2010/0269990 A1 | 10/2010 | Dottori et al. |
| 2010/0279354 A1 | 11/2010 | De |
| 2010/0279361 A1 | 11/2010 | South et al. |
| 2010/0279372 A1 | 11/2010 | Cho et al. |
| 2010/0287826 A1 | 11/2010 | Hoffman et al. |
| 2010/0305241 A1 | 12/2010 | Balakshin et al. |
| 2010/0305242 A1 | 12/2010 | Balakshin et al. |
| 2010/0305243 A1 | 12/2010 | Balakshin et al. |
| 2010/0305244 A1 | 12/2010 | Balakshin et al. |
| 2011/0003348 A1 | 1/2011 | Genta et al. |
| 2011/0003352 A1 | 1/2011 | Retsina et al. |
| 2011/0016545 A1 | 1/2011 | Gray et al. |
| 2011/0020873 A1 | 1/2011 | Ren et al. |
| 2011/0020910 A1 | 1/2011 | Glass et al. |
| 2011/0028672 A1 | 2/2011 | Dahlman et al. |
| 2011/0028710 A1 | 2/2011 | Baniel et al. |
| 2011/0033640 A1 | 2/2011 | Yamada et al. |
| 2011/0033896 A1 | 2/2011 | Boy et al. |
| 2011/0053238 A1 | 3/2011 | Ohgren et al. |
| 2011/0059316 A1 | 3/2011 | Kilambi et al. |
| 2011/0060132 A1 | 3/2011 | Lewis |
| 2011/0065159 A1 | 3/2011 | Raines et al. |
| 2011/0070131 A1 | 3/2011 | Schmidt et al. |
| 2011/0097776 A1 | 4/2011 | Johnson |
| 2011/0100359 A1 | 5/2011 | North |
| 2011/0105737 A1 | 5/2011 | Benjelloun et al. |
| 2011/0124057 A1 | 5/2011 | Genta et al. |
| 2011/0126448 A1 | 6/2011 | Dumenil |
| 2011/0129880 A1 | 6/2011 | Conners et al. |
| 2011/0129886 A1 | 6/2011 | Howard et al. |
| 2011/0143412 A1 | 6/2011 | Kim et al. |
| 2011/0146138 A1 | 6/2011 | Berry et al. |
| 2011/0151516 A1 | 6/2011 | Van et al. |
| 2011/0155559 A1 | 6/2011 | Medoff |
| 2011/0172411 A1 | 7/2011 | Heikkila et al. |
| 2011/0178290 A1 | 7/2011 | Baniel et al. |
| 2011/0183394 A1 | 7/2011 | Bell et al. |
| 2011/0192560 A1 | 8/2011 | Heikkila et al. |
| 2011/0201059 A1 | 8/2011 | Hall et al. |
| 2011/0245491 A1 | 10/2011 | Airaksinen et al. |
| 2011/0262984 A1 | 10/2011 | Nguyen |
| 2011/0263811 A1 | 10/2011 | Sawai et al. |
| 2011/0268652 A1 | 11/2011 | Machhammer et al. |
| 2011/0271875 A1 | 11/2011 | Ahmed et al. |
| 2011/0275860 A1 | 11/2011 | Beldring et al. |
| 2011/0281298 A1 | 11/2011 | Rawls et al. |
| 2011/0300617 A1 | 12/2011 | Genta et al. |
| 2011/0314726 A1 | 12/2011 | Jameel et al. |
| 2011/0318796 A1 | 12/2011 | Walther |
| 2012/0006320 A1 | 1/2012 | Nguyen |
| 2012/0021467 A1 | 1/2012 | Zhang et al. |
| 2012/0023810 A1 | 2/2012 | Fjare et al. |
| 2012/0036768 A1 | 2/2012 | Phillips et al. |
| 2012/0055466 A1 | 3/2012 | Cotti et al. |
| 2012/0058526 A1 | 3/2012 | Jansen et al. |
| 2012/0104313 A1 | 5/2012 | Garbero et al. |
| 2012/0116063 A1 | 5/2012 | Jansen et al. |
| 2012/0122170 A1 | 5/2012 | Ropars et al. |
| 2012/0134912 A1 | 5/2012 | Baniel et al. |
| 2012/0149924 A1 | 6/2012 | De et al. |

(56) References Cited

U.S. PATENT DOCUMENTS

| | | |
|---|---|---|
| 2012/0156517 A1 | 6/2012 | Vuori et al. |
| 2012/0167874 A1 | 7/2012 | Jansen et al. |
| 2012/0184026 A1 | 7/2012 | Eyal |
| 2012/0227733 A1 | 9/2012 | Eyal et al. |
| 2012/0264873 A1 | 10/2012 | Eyal et al. |
| 2012/0279497 A1 | 11/2012 | Jansen et al. |
| 2012/0304529 A1 | 12/2012 | O'Connor et al. |
| 2012/0308991 A1 | 12/2012 | Eiteman et al. |
| 2012/0323053 A1 | 12/2012 | Qiao et al. |
| 2013/0012610 A1 | 1/2013 | Belanger et al. |
| 2013/0019859 A1 | 1/2013 | Qiao et al. |
| 2013/0028832 A1 | 1/2013 | Eyal et al. |
| 2013/0028833 A1 | 1/2013 | Eyal et al. |
| 2013/0047979 A1 | 2/2013 | Eyal et al. |
| 2013/0115653 A1 | 5/2013 | Peterson et al. |
| 2013/0167836 A1 | 7/2013 | Floyd et al. |
| 2013/0167837 A1 | 7/2013 | Floyd et al. |
| 2013/0210101 A1 | 8/2013 | Parekh et al. |
| 2013/0216693 A1 | 8/2013 | Harrison et al. |
| 2013/0217070 A1 | 8/2013 | Zhao et al. |
| 2013/0252312 A1 | 9/2013 | Yoshikuni et al. |
| 2013/0276778 A1 | 10/2013 | Jansen et al. |
| 2014/0011241 A1 | 1/2014 | Beatty et al. |
| 2014/0014092 A1 | 1/2014 | Kazachkin et al. |
| 2014/0175331 A1 | 6/2014 | Jansen et al. |
| 2014/0200365 A1 | 7/2014 | De Haan et al. |
| 2014/0220651 A1 | 8/2014 | Raines et al. |
| 2014/0227161 A1 | 8/2014 | Manesh et al. |
| 2014/0271443 A1 | 9/2014 | Baker et al. |
| 2014/0275501 A1 | 9/2014 | Capanema et al. |
| 2014/0309416 A1 | 10/2014 | Teixeira et al. |
| 2014/0356915 A1 | 12/2014 | Retsina et al. |
| 2015/0020797 A1 | 1/2015 | Eyal et al. |
| 2015/0028255 A1 | 1/2015 | Eyal et al. |
| 2015/0048274 A1 | 2/2015 | Eyal et al. |
| 2015/0144126 A1 | 5/2015 | Jansen et al. |
| 2015/0176090 A1 | 6/2015 | Dumesic et al. |
| 2015/0197824 A1 | 7/2015 | Floyd et al. |
| 2016/0108481 A1 | 4/2016 | Eyal et al. |
| 2016/0108482 A1 | 4/2016 | Eyal et al. |
| 2016/0376546 A1 | 12/2016 | Eyal et al. |
| 2017/0037486 A1 | 2/2017 | Eyal et al. |
| 2017/0130282 A1 | 5/2017 | Eyal et al. |
| 2017/0369957 A1 | 12/2017 | Jansen et al. |
| 2018/0142314 A1 | 5/2018 | Eyal et al. |
| 2018/0148804 A1 | 5/2018 | Jansen et al. |
| 2018/0223383 A1 | 8/2018 | Eyal et al. |

FOREIGN PATENT DOCUMENTS

| | | |
|---|---|---|
| CN | 101016703 A | 8/2007 |
| CN | 101279722 A | 10/2008 |
| CN | 101313073 A | 11/2008 |
| CN | 101550431 A | 10/2009 |
| CN | 101787398 A | 7/2010 |
| CN | 102433358 B | 10/2013 |
| CZ | 301471 B6 | 3/2010 |
| DE | 4106373 A1 | 9/1992 |
| DE | 19721301 C1 | 10/1998 |
| DE | 102008064325 A1 | 7/2010 |
| EP | 0018621 A1 | 11/1980 |
| EP | 0317036 A1 | 5/1989 |
| EP | 0224721 B1 | 6/1991 |
| EP | 0247436 B1 | 1/1992 |
| EP | 0493842 A2 | 7/1992 |
| EP | 0504622 A1 | 9/1992 |
| EP | 0560546 A1 | 9/1993 |
| EP | 0446556 B1 | 8/1995 |
| EP | 0700957 A1 | 3/1996 |
| EP | 0878455 A1 | 11/1998 |
| EP | 0690931 B1 | 10/2001 |
| EP | 0697904 B1 | 6/2002 |
| EP | 1253241 A2 | 10/2002 |
| EP | 1272433 B1 | 1/2004 |
| EP | 1253241 A3 | 2/2004 |
| EP | 1878480 A1 | 1/2008 |
| EP | 1918031 A1 | 5/2008 |
| EP | 2336193 A1 | 6/2011 |
| EP | 1458805 B1 | 8/2011 |
| EP | 1733282 B1 | 1/2012 |
| EP | 2325246 B1 | 11/2013 |
| FR | 2604728 A1 | 4/1988 |
| GB | 1562682 A | 3/1980 |
| GB | 2034291 A | 6/1980 |
| GB | 2488918 B | 3/2014 |
| JP | 2001226409 A | 8/2001 |
| JP | 2010501013 A | 1/2010 |
| JP | 2010083850 A | 4/2010 |
| KR | 100564708 B1 | 3/2006 |
| KR | 20140108301 A | 9/2014 |
| WO | WO-8201723 A1 | 5/1982 |
| WO | WO-8403304 A1 | 8/1984 |
| WO | WO-9218557 A1 | 10/1992 |
| WO | WO-9305186 A1 | 3/1993 |
| WO | WO-9313265 A1 | 7/1993 |
| WO | WO-9417213 A1 | 8/1994 |
| WO | WO-9426380 A1 | 11/1994 |
| WO | WO-9502726 A1 | 1/1995 |
| WO | WO-9609350 A1 | 3/1996 |
| WO | WO-9641052 A1 | 12/1996 |
| WO | WO-9713732 A2 | 4/1997 |
| WO | WO-9713732 A3 | 5/1997 |
| WO | WO-9963145 A1 | 12/1999 |
| WO | WO-0125143 A1 | 4/2001 |
| WO | WO-0132715 A1 | 5/2001 |
| WO | WO-0202826 A1 | 1/2002 |
| WO | WO-03010339 A1 | 2/2003 |
| WO | WO-03029329 A2 | 4/2003 |
| WO | WO-03056038 A1 | 7/2003 |
| WO | WO-03078540 A2 | 9/2003 |
| WO | WO-03078540 A3 | 1/2004 |
| WO | WO-2004050983 A1 | 6/2004 |
| WO | WO-2004079017 A2 | 9/2004 |
| WO | WO-2004079017 A3 | 8/2005 |
| WO | WO-2006006164 A2 | 1/2006 |
| WO | WO-2006034581 A1 | 4/2006 |
| WO | WO-2006038863 A1 | 4/2006 |
| WO | WO-2006056838 A1 | 6/2006 |
| WO | WO-2006086861 A2 | 8/2006 |
| WO | WO-2006086861 A3 | 10/2006 |
| WO | WO-2006119357 A2 | 11/2006 |
| WO | WO-2006119357 A3 | 1/2007 |
| WO | WO-2007019505 A2 | 2/2007 |
| WO | WO-2007019505 A3 | 6/2007 |
| WO | WO-2007075476 A2 | 7/2007 |
| WO | WO-2007102638 A1 | 9/2007 |
| WO | WO-2007112314 A2 | 10/2007 |
| WO | WO-2007112314 A3 | 11/2007 |
| WO | WO-2007124400 A2 | 11/2007 |
| WO | WO-2007130984 A2 | 11/2007 |
| WO | WO-2008017145 A1 | 2/2008 |
| WO | WO-2008019468 A1 | 2/2008 |
| WO | WO-2007075476 A3 | 3/2008 |
| WO | WO-2008027699 A2 | 3/2008 |
| WO | WO-2008069830 A2 | 6/2008 |
| WO | WO-2008027699 A3 | 7/2008 |
| WO | WO-2007124400 A3 | 8/2008 |
| WO | WO-2008098036 A1 | 8/2008 |
| WO | WO-2008109877 A1 | 9/2008 |
| WO | WO-2008111045 A1 | 9/2008 |
| WO | WO-2008123419 A1 | 10/2008 |
| WO | WO-2008131229 A1 | 10/2008 |
| WO | WO-2008069830 A3 | 11/2008 |
| WO | WO-2008137639 A1 | 11/2008 |
| WO | WO-2008140617 A2 | 11/2008 |
| WO | WO-2008144903 A1 | 12/2008 |
| WO | WO-2009002785 A1 | 12/2008 |
| WO | WO-2009003167 A1 | 12/2008 |
| WO | WO-2008140617 A3 | 1/2009 |
| WO | WO-2009003292 A1 | 1/2009 |
| WO | WO-2009015663 A2 | 2/2009 |
| WO | WO-2009020459 A2 | 2/2009 |
| WO | WO-2009021733 A2 | 2/2009 |
| WO | WO-2009028969 A1 | 3/2009 |

(56) References Cited

FOREIGN PATENT DOCUMENTS

| | | |
|---|---|---|
| WO | WO-2009030713 A1 | 3/2009 |
| WO | WO-2009031164 A1 | 3/2009 |
| WO | WO-2009036674 A1 | 3/2009 |
| WO | WO-2009020459 A3 | 4/2009 |
| WO | WO-2006006164 A3 | 5/2009 |
| WO | WO-2009021733 A3 | 6/2009 |
| WO | WO-2009068711 A1 | 6/2009 |
| WO | WO-2009111026 A2 | 9/2009 |
| WO | WO-2009125400 A2 | 10/2009 |
| WO | WO-2009135480 A1 | 11/2009 |
| WO | WO-2009142837 A2 | 11/2009 |
| WO | WO-2009015663 A3 | 12/2009 |
| WO | WO-2009155982 A1 | 12/2009 |
| WO | WO-2009125400 A3 | 1/2010 |
| WO | WO-2010006840 A2 | 1/2010 |
| WO | WO-2010009343 A2 | 1/2010 |
| WO | WO-2010009515 A1 | 1/2010 |
| WO | WO-2010015404 A1 | 2/2010 |
| WO | WO-2010018105 A1 | 2/2010 |
| WO | WO-2010020977 A2 | 2/2010 |
| WO | WO-2009142837 A3 | 3/2010 |
| WO | WO-2010026244 A1 | 3/2010 |
| WO | WO-2010026572 A1 | 3/2010 |
| WO | WO-2010009343 A3 | 4/2010 |
| WO | WO-2010034055 A1 | 4/2010 |
| WO | WO-2010037109 A2 | 4/2010 |
| WO | WO-2010037178 A1 | 4/2010 |
| WO | WO-2010038021 A2 | 4/2010 |
| WO | WO-2010039152 A1 | 4/2010 |
| WO | WO-2010043424 A1 | 4/2010 |
| WO | WO-2010045576 A2 | 4/2010 |
| WO | WO-2010046619 A1 | 4/2010 |
| WO | WO-2010006840 A3 | 5/2010 |
| WO | WO-2010037109 A3 | 5/2010 |
| WO | WO-2010060183 A1 | 6/2010 |
| WO | WO-2010064229 A2 | 6/2010 |
| WO | WO-2010045576 A3 | 7/2010 |
| WO | WO-2010064229 A3 | 7/2010 |
| WO | WO-2010081231 A1 | 7/2010 |
| WO | WO-2010038021 A3 | 8/2010 |
| WO | WO-2010088486 A1 | 8/2010 |
| WO | WO-2010020977 A3 | 10/2010 |
| WO | WO-2010113129 A2 | 10/2010 |
| WO | WO-2010113130 A2 | 10/2010 |
| WO | WO-2010122554 A1 | 10/2010 |
| WO | WO-2010123932 A1 | 10/2010 |
| WO | WO-2010128272 A1 | 11/2010 |
| WO | WO-2010113129 A3 | 12/2010 |
| WO | WO-2010135804 A1 | 12/2010 |
| WO | WO-2010135805 A1 | 12/2010 |
| WO | WO-2010135806 A1 | 12/2010 |
| WO | WO-2010135807 A1 | 12/2010 |
| WO | WO-2010135832 A1 | 12/2010 |
| WO | WO-2010135833 A1 | 12/2010 |
| WO | WO-2010146331 A2 | 12/2010 |
| WO | WO-2010113130 A3 | 1/2011 |
| WO | WO-2011002660 A1 | 1/2011 |
| WO | WO-2011007043 A1 | 1/2011 |
| WO | WO-2011007369 A1 | 1/2011 |
| WO | WO-2011017587 A1 | 2/2011 |
| WO | WO-2011022840 A1 | 3/2011 |
| WO | WO-2011028554 A1 | 3/2011 |
| WO | WO-2011039751 A2 | 4/2011 |
| WO | WO-2011066487 A1 | 6/2011 |
| WO | WO-2011070602 A1 | 6/2011 |
| WO | WO-2011080131 A2 | 7/2011 |
| WO | WO-2011089589 A1 | 7/2011 |
| WO | WO-2011091044 A1 | 7/2011 |
| WO | WO-2011095977 A1 * | 8/2011 | ........... C01B 7/0737 |
| WO | WO-2011097719 A1 | 8/2011 |
| WO | WO-2011080131 A3 | 9/2011 |
| WO | WO-2011111189 A1 | 9/2011 |
| WO | WO-2011111190 A1 | 9/2011 |
| WO | WO-2010146331 A3 | 10/2011 |
| WO | WO-2011039751 A3 | 10/2011 |
| WO | WO-2011121181 A1 | 10/2011 |
| WO | WO-2011124639 A1 | 10/2011 |
| WO | WO-2011140222 A1 | 11/2011 |
| WO | WO-2011151823 A1 | 12/2011 |
| WO | WO-2011154604 A1 | 12/2011 |
| WO | WO-2011154967 A1 | 12/2011 |
| WO | WO-2011161141 A1 | 12/2011 |
| WO | WO-2011161685 A2 | 12/2011 |
| WO | WO-2011163084 A1 | 12/2011 |
| WO | WO-2012001688 A2 | 1/2012 |
| WO | WO-2012015575 A1 | 2/2012 |
| WO | WO-2012018740 A1 | 2/2012 |
| WO | WO-2012031270 A1 | 3/2012 |
| WO | WO-2012044168 A1 | 4/2012 |
| WO | WO-2011161685 A3 | 5/2012 |
| WO | WO-2012060767 A1 | 5/2012 |
| WO | WO-2012079021 A2 | 6/2012 |
| WO | WO-2012085684 A2 | 6/2012 |
| WO | WO-2012106727 A1 | 8/2012 |
| WO | WO-2012137201 A1 | 10/2012 |
| WO | WO-2012170520 A1 | 12/2012 |
| WO | WO-2013024162 A1 | 2/2013 |
| WO | WO-2013038399 A1 | 3/2013 |
| WO | WO-2013040514 A1 | 3/2013 |
| WO | WO-2013040702 A1 | 3/2013 |
| WO | WO-2013055785 A1 | 4/2013 |
| WO | WO-2013083876 A2 | 6/2013 |
| WO | WO-2013166469 A2 | 11/2013 |
| WO | WO-2013192572 A1 | 12/2013 |
| WO | WO-2014044753 A1 | 3/2014 |
| WO | WO-2014076612 A1 | 5/2014 |
| WO | WO-2014081605 A1 | 5/2014 |
| WO | WO-2014126471 A1 | 8/2014 |
| WO | WO-2014138553 A1 | 9/2014 |
| WO | WO-2014169079 A2 | 10/2014 |
| WO | WO-2014178911 A1 | 11/2014 |
| WO | WO-2015139141 A1 | 9/2015 |
| WO | WO-2016112134 A1 | 7/2016 |
| WO | WO-2016191503 A1 | 12/2016 |

OTHER PUBLICATIONS

Co-pending U.S. Appl. No. 16/016,467, filed Jun. 22, 2018.

Notice of Allowance dated Dec. 5, 2017 for U.S. Appl. No. 15/191,376.

Office Action dated May 4, 2017 for U.S. Appl. No. 15/191,376.

Rangamannar, et al. Improved wet bulk storage of bagasse for newsprint pulp production—part 1. Pulping conference TAPPI proceedings. 1993; 391-398.

U.S. Appl. No. 15/191,376 Notice of Allowance dated Mar. 21, 2018.

EP18175599.2 Extended European Search Report dated Oct. 8, 2018.

Abacherli, et al. Lignin Analytical Cluster, "Towards Standardisation of Methods". Rome, Forum 8, May 10-12, 2007.

Abacherli. Lignin structure and analytical methods. International Lignin Institute, Rue du Grand-Chêne 5, CH-1005 Lausanne, Switzerland Copyright ILI 2008, only for ILI members and only for personal use, Last update Jun. 20, 2008.

Abacherli. New lignins from agricultural plants. The international Lignin Institute, 5th international Forum' Sep. 7, 2000, Bordeaux (France).

Acevedo, et al. Surface Activity of Lignin Fractions isolated by Organic Solvents. Powerpoint. 2005.

Achyuthan, et al. Supramolecular Self-Assembled Chaos: Polyphenolic Lignin's Barrier to Cost-Effective Lignocellulosic Biofuels. Molecules. 2010; 15:8641-8688. doi:10.3390/molecules15118641.

Addi, et al. Flax lignin and lignans:Biosynthesis, Metabolism and Directed Modifications through a Genetic Engineering Approach. 2003.

Aden, et al. Lignocellulosic Biomass to Ethanol Process Design and Economics Utilizing Co-Current Dilute Acid Prehydrolysis and Enzymatic Hydrolysis for Corn Stover. National Renewable Energy Laboratory, NREL is a U.S. Department of Energy Laboratory Operated by Midwest Research Institute. Jun. 2002.

(56) References Cited

OTHER PUBLICATIONS

Adina, et al. Application of FTIR Spectroscopy for a Rapid Determination of Some Hydrolytic Enzymes Activity on Sea Buckthorn Substrate. Romanian Biotechnological Letters. 2010; 15(6):5738-5744.
ADM corn 42/43 syrup. Typical data information. Accessed Oct. 5, 2012.
Afanasiev, et al. Forecast of lignosulfonates properties as surfactant. 2005.
Afanasiev, et al. Stabilization effect of microparticles of sulfate lignin on water-oil emulsion. Powerpoint. 2005.
Agarwal, et al. FT raman spectroscopic study of softwood lignin. ISWPC. 1997.
Agarwal, et al. Near-IR surface-enhanced Raman spectrum of lignin. J. Raman Spectrosc. 2009; 40:1527-1534.
Agarwal, et al. Raman spectra of lignin model compounds. incorporating the 13th ISWFPC (International Symposium on Wood, Fibre, and Pulping Chemistry), held in Auckland, New Zealand (May 16-19, 2005).Appita 2005, pp. 1-8.
Agblevor, et al. Analysis of biomass sugars using a novel HPLC method. Appl Biochem Biotechnol. Mar. 2007;136(3):309-26.
Ahlkvist.J. Formic and Levulinic Acid from Cellulose via Heterogeneous Catalysis. PhD Report. 2014, Sweden.
Ahmed, et al. A simplified method for accurate determination of cell wall uronide content. Journal of Food Biochemistry.1977; 1:361-365.
Ahmed, et al. Preparation and studies on immobilized $\alpha$-glucosidase from baker's yeast *Saccharomyces cerevisiae* J. Serb. Chem. Soc. 2007; 72(12):1255-1263.
Albersheim. Metabolism of the Pectic Substances. For the degree of Doctor of Philosophy, California Institute of Technology Pasadena, California, 1959.
Albertson, et al. Addition Compounds of Sulfur Dioxide. Sep. 1943; 65:1687-1690.
Alizadeh, et al. Pretreatment of Switchgrass by Ammonia Fiber Explosion (AFEX). Applied Biochemistry and Biotechnology. 2005; 5(121-124):1133-1142.
Allosio-Ouarnier, et al. Application of High Performance Anion Exchange Chromatography to the Study of Carbohydrate Changes in Barley During Malting. Journal—Institute of Brewing 106(1):45-52. Jan. 2000.
Allsopp, et al. 130. The constitution of the cambium, the new wood and the mature sapwood of the common ash, the common elm and the scotch pine. May 10, 1940; 1078-1084.
Alonso-Fagundez, et al. Selective conversion of furfural to maleic anhydride and furan with Vo(x)/Al(2)O(3) catalysts. 2012 ;5: 1984-1990.
Ambalkar, et al. Synthesis of Furfural from Lignocellulosic Biomass as Agricultural Residues : A Review. The International Journal of Engineering and Science. 2012; 1(1): 30-36.
Amidon, et al. Biorefinery: Conversion of Woody Biomass to Chemicals, Energy and Materials. Journal of Biobased Materials and Bioenergy. 2008; 2:100-120.
Anderson. The isolation of pectic substances from wood. 1935; 531-539.
Anellotech. Scaling up economical, non-food biomass derived Benzene, Toluene and Xylenes for major biobased polymers. Presentation by Anellotech; San Francisco. 2013.
Antonoplis, et al. High pressure HCl conversion of cellulose to glucose. Lawrence Berkeley National Laboratory, University of California, Paper LBL,14221. Aug. 1981.
Arborgen. Purpose Grown Trees as an Economical and Sustainable Biomass Feedstock. Southeast Bioenergy conference, Presentation. 2010.
Argyropoulos. Oxidaton of Lignin in supercritical carbon dioxide. 2005.
Argyropoulus et al. Bioenergy Program. Presentation; NC State University. 2014.
ASTM Standards. Standard Test Method for Ash in Biomass. Designation: E1755-01 (Reapproved 2007).
Atalla, et al. Analysis of Lignin and Cellulose in Biological Energy Sources by Raman Microscopy. 2011.
Atchison, et al. Innovative Methods for Corn Stover Collecting, Handling, Storing and Transporting, Mar. 2003. National Renewable Energy Laboratory. Apr. 2004.
Atsuki. Action of highly concentrated hydrochloric acid on cellulose. Seniso Kogyo (1925), 1 53-61. CODEN: SKOGBJ ISSN: 0371-070X. Abstract only.
Badger. Ethanol from cellulose: a general review. Trends in new crops and new uses. 2002; 17-21.
Baker. Utilization of Sustainable Resources for Materials for Production of Carbon Fiber Structural and Energy Efficiency Applications. Oak Ridge National Laboratory, Tennessee, USA. Nordic Wood Biorefinery Conference, Stockholm, Sweden, Mar. 22-24, 2011.
Bakker. Advanced physical/chemical fractionation. Workshop of the EU FP6, Integrated Project BIOSYNERGY. Nov. 17, 2011.
Baniel, et al. Porogen derived membranes.1. Concept description and analysis. J. of Membrane Science. 1990; 54:271-283.
Baniel. Reactions and processes in Liquidliquid (L/L) systems. Pure & Appl. Chem. 1986; 58(6):879-883.
Bao, et al. Preparation of 5-hydroxymethylfurfural by dehydration of fructose in the presence of acidic ionic liquid. Catalysis Communications; 2008; 9: 1383-1388.
Barneto, et al. Thermogravimetric characterization of eucaliptus wood. Artigo Tecnico 2011, 72(7), 53-56.
Barta, et al. Catalytic disassembly of an organosolv lignin via hydrogen transfer from supercritical methanol. Green Chem. 2010; 12:1640-1647.
Barton. CRC handbook of solubility parameters and other cohesion parameters. CRC Press. Boca Raton. 1991; 122-138.
Basak, et al. Thermal Properties of Jute Constituents and Flame Retardant Jute Fabrics. Textile Res. J. 1993, 63(11), 658-666.
Baumberger, et al. An overview of the analytical tools in the quali/quantitative analysis of functional groups and inter unit bondings in lignin.II. Interunit bondings characterization. COST E41—Roma—Jun. 7-8, 2007.
Baumberger, et al. Analytical methods for lignin characterisation, used by users (end-users and R&D companies). Compilation of all the protocols received by Oct. 31, 2003.
Bayat-Makooi, et al. Hydrolysis of cellulose with hydrochloric acid enhanced by cations. Dep. Wood Paper Sci., North Carolina State Univ., Raleigh, NC, USA. Editor(s): Kennedy, John F. Cellul. Its Deriv. (1985), 135-41. Publisher: Horwood, Chichester, UK CODEN: 54GPAW. Abstract only.
Beck, et al. Production of ethanol by bioconversion of wood sugars derived from two-stage dilute acid hydrolysis of hardwood. Biomass. 1984; 6:101-110.
Beg, et al. Cyclic transport of Fe3+ as H[FeCl4] and H[FeBr4] through a dibutyl ether-benzene membrane. Journal of Membrane Science. 1985; 24:97-100.
Berg, et al. The breaking of ternary acetate-alcohol-water azeotropes by extractive distillation. Chem. Eng. Commun. 1986; 48:93-101.
Bergius. Conversion of wood to carbohydrates and problems in the industrial use of concentrated hydrochloric acid. Industrial and Engineering chemistry. 1937; 29(3):247-253.
Bergius. The utilisation of wood for the production of foodstuffs, alcohol and glucose. Chemical society institution. Nov. 15, 1933.
Bergius. Winslow Notes on Bergius Process. 1937.
Bergius. Wood Sugar Plants at Mannheim-Rheinau & Regensburg. 1945.
Berndes, et al. The contribution of biomass in the future global energy supply: a review of 17 studies. Biomass and Bioenergy. 2003; 25:1-28.
Berthold, et al. Association of water to polar groups; estimations by an adsorption model for ligno-cellulosic materials. Colloids Surfaces A:Physicochem. Eng. Aspects. 1996; 112:117-129.
Bilanicova, et al. Improvements in Enzymatic Preparation of Alkyl Glycosides. Czech J. Food Sci. 2010I28(1): 69-73.
Binder, et al. Mechanistic insights on the conversion of sugars into 5-hydroxymethylfurfural. Energy Environ. Sci., 2010; 3:765-771.

(56) References Cited

OTHER PUBLICATIONS

Binder, et al. Simple chemical transformation of lignocellulosic biomass into furans for fuels and chemicals. J Am Chem Soc. Feb. 11, 2009;131(5):1979-85. doi: 10.1021/ja808537j.
Biology Online. "Oligosaccharide". Downloaded Mar. 27, 2017. 1 page.
Bizzari, et al. CEH Marketing Research Report, LIGNOSULFONATES. 671.5000 A. Jan. 2009.
Blommel, et al. Production of conventional liquid fuels from sugars. Virent energy systems. Aug. 25, 2008. 1-14.
Bo, et al. Mutual Solubilities for Water—o—Nitrotoluene System and Distribution Coefficients for Furfural and Acetic Acid in Water—o—Nitrotoluene System. J. Chem. Eng. Data; 2010;55;5191-5195.
Bochek. Effect of Hydrogen Bonding on Cellulose Solubility in Aqueous and Nonaqueous Solvents. Russian Journal of Applied Chemistry, vol. 76, No. 11, 2003, pp. 1711-1719.
Boeriu. Characterisation of structure-dependent functional properties. 2003.
Bonini, et al. Degradation and recovery of fine chemicals through singlet oxygen treatment of lignin. 2003.
Bonini, et al. New Materials from Lignin. 2005.
Bonini, et al. Qualitative 13C NMR spectra of lignin. Analytical methods for lignin characterisation. International Lignin Institute Version: 1.2, Last date of review: Aug. 2008.
Bonini. Low cost steam exploded lignin from straw: degradation and use. The international Lignin Institute, 5th international Forum' Sep. 7, 2000, Bordeaux (France).
Bourbonnais, et al. Lignin Oxidation by Laccase Isozymes from Trametes versicolor and Role of the Mediator 2,29-Azinobis(3-Ethylbenzthiazoline- 6-Sulfonate) in Kraft Lignin Depolymerization. Applied and environmental microbiology. May 1995; 61(5):1876-1880.
Bozell et al. Top Value Added Chemicals from Biomass vol. I—Results of Screening for Potential Candidates from Sugars and Synthesis Gas Top Value Added Chemicals From Biomass vol. I : Results of Screening for Potential Candidates. NREL report.2004: 1-76.
Bozell. The Use of Renewable Feedstocks for the Production of Chemicals and Materials—A Brief Overview of Concepts. National Renewable Energy Laboratory, 1617 Cole Boulevard, Golden, CO 80401. 2010.
Braun, et al. Lignin-based carbon fibers: Oxidative thermostabilization of kraft lignin. Carbon.2005; 43:385-394.
Bridgwater, et al. Identification and market analysis of most promising added-value products to be co-produced with the fuels. Project No: 212831, Project end date: May 31, 2010; 1-132.
Brito, et al. Chemical composition changes in eucalyptus and pinus woods submitted to heat treatment. Bioresource Technology. 2008; 99:8545-8548.
Brodin, et al. Characteristics of lignin blends intended for carbon fibre production. 2008.
Brown. Determination of Dry Substance in Beet Sugar Juices, A Precision Method. Industrial and Engineering chemistry. Jul. 1924; 16(7):746-748.
Brown, et al. Initial Market Assessment for Small-Scale Biomass-Based CHP, Prepared under Task No. WF6N.1050. National Renewable Energy Laboratory. Jan. 2008.
Brown. Mixed acid recovery with the APU™ acid sorption system. ECO-TEC, Technical Paper 147, Jan. 1997.
Brownell, et al. Steam-Explosion Pretreatment of Wood: Effect of Chip Size, Acid, Moisture Content and Pressure Drop. Biotechnology and Bioengineering. 1986; XXVIII:792-801.
Brummer, et al. Understanding Carbohydrate Analysis. Chapter 2. Copyright 2005 by Taylor & Francis Group, LLC.
Brunner. Near critical and supercritical water. Part I. Hydrolytic and hydrothermal processes. J. of Supercritical Fluids. 2009; 47:373-381.
Bulushev, et al. Catalysis for conversion of biomass to fuels via pyrolysis and gasification: A review. Catalysts Today. 2001; 171: 1-13.
Bunker. The Wartime Production of Food Yeast in Germany. 2010.
Burchell, et al. The development of novel activated carbon composites. 17th Annual Conference on Fossil Energy Materials, Wyndham Baltimore Inner Harbor Hotel, Baltimore, Maryland, Apr. 22-24, 2003.
Busche. The Klason lignin determination as applied to aspenwood with special: reference to acid-soluble lignin. The Institute of Paper Chemistry, Appleton, Wisconsin,Doctors Dissertation, A thesis submitted Jun. 1960.
Bustos, et al. Modeling of the Hydrolysis of Sugar Cane Bagasse with Hydrochloric Acid. Applied Biochemistry and Biotechnology. 2003; 104:51-68.
Bykov. Characterization of Natural and Technical Lignins using FTIR Spectroscopy. Master's Thesis, Division of Chemical Technology Department of Chemical Engineering and Geosciences, Lulea University of Technology. Feb. 2008.
Byrne. Expression, purification and crystallisation of membrane proteins. 2011.
Cai, et al. Integrated furfural production as a renewable fuel and chemical platform from lignocellulosic biomass. J. Chem. Technol. Biotechnol. 2014; 89: 2-10.
Campa et al. Capillary Electrophoresis of Neutral Carbohydrates. Methods in molecular biology.2008; 384:247-305.
Campa et al. Capillary electrophoresis of sugar acids. Methods in molecular biology. 2008; 384: 307-355.
Campbell et al. The bleaching action of alkaline hydrogen peroxide on wood. The Biochemical journal. 1938; 32(4): 702-707.
Campbell. The Degradation of wood by simultaneous action of ethyl alcohol and hydrochloric acid. 1929; 1225-1232.
Campbell,et al. The Saccharification of Wood by the Bergius process at Suddeutschen Holzversucherung Werke A.G. Regensburg. Report on visit to Suddeutschen Holzversucherung Werke A.G. Regensburg.CIOS trip No. 764, this target was visited on Aug. 9, 1945.
Campos. Calculations of VLE in electrolytes systems using chemical theory: aqueous acis chloridric system. 2nd Mercosur Congress on Chemical Engineering; 4th Mercosur Congress on Process Systems Engineering. 2008.
Canetti, et al. Thermal degradation behaviour of isotactic polypropylene with lignin. Polym. Degr. and stability 2006, 91, 494-498.
Capraru, et al. Contribution to the modification and characterization of different types of lignins. Cellulose Chem. Technol. 2009; 43(9-10):409-418.
Cardona, et al. Production of bioethanol from sugarcane bagasse: Status and perspectives. Bioresource Technology. 2010; 101:4754-4766.
Carole, et al. Opportunities in the Industrial Biobased Products Industry. Applied Biochemistry and Biotechnology. 2004; 113-116:871-88.
Carr. The Biobased Revolution: How Biotechnology and Policy Are Changing the Way Materials Are Made. ASC Fall Convention & Expo. Oct. 11, 2005.
Carrott, et al. Lignin—from natural adsorbent to activated carbon: A review. Bioresource Technology 2007; 98:2301-2312.
Carvalheiro, et al. Hemicellulose biorefineries: a review on biomass pretreatments. Journal of Scientific and Industrial Research. 2008; 67:849-864.
Carvalho, et al. Comparison of different procedures for the detoxification of eucalyptus hemicellulosic hydrolysate for use in fermentative processes. J Chem Technol Biotechnol 2006; 81:152-157.
Castro et al., Ecologically safe alkyl glucoside-based gemini surfactants. ARKIVOC, xii (2005): 253-267.
Cateto, et al. Lignin-based polyurethane materials. Proceedings of the 10th International Chemical and Biological Engineering Conference—CHEMPOR 2008 Braga, Portugal, Sep. 4-6, 2008 E.C. Ferreira and M. Mota (Eds.).
Cateto, et al. Monitoring of lignin-based polyurethane synthesis by FTIR-ATR. Barcelona, Apr. 27-28, 2005.
Cateto, et al. Oxypropylation of Lignins and Characterization of the Ensuing Polyols. Laboratory of Separation and Reaction Engineering, Braganca Polytechnic Institute, School of Engineering—

(56) References Cited

OTHER PUBLICATIONS

University of Porto, Ecole Francaise de Papeterie et des Industries Graphiques, Institut National Polytechnique de Grenoble. 2007. Powerpoint.
Cateto, et al. Rigid Polyurethane foams from lignin-based polyols. Laboratory of Separation and Reaction Engineering. 2008.
Cayle, et al. The application of Mathews' Formula in Enzymatic Starch Conversions. Mar. 1966; 43:237-244.
Cazacu, et al. Lignin—component of complex materials. 2005; 64-71.
Cazacu, et al. Lignin characterization for its use in complex polymeric systems. Polymer Nanomaterials for Food Packaging, Characterization Needs, Safety and Environmental Issues, Sep. 1-2, 2010, London.
Celunol. EESI Congressional Briefing. Sep. 22, 2006.
Cetin, et al. Studies on Lignin-Based Adhesives for Particleboard Panels. Turk J Agric for. 2003; 27:183-189.
Chakar, et al. Review of current and future softwood kraft lignin process chemistry. Industrial crops and products. 2004; 20:131-141.
Chalov, et al. Continuous hydrolysis of plant tissue polysaccharides with 46-48% hydrochloric acid. III. Absorption of hydrogen chloride by moist wood. Izvestiya Vysshikh Uchebnykh Zavedenii, Lesnoi Zhurnal (1966), 9(6), 139-43. CODEN: IVZLAL ISSN: 0536-1036. Abstract only.
Chalov, et al. Continuous hydrolysis of plant tissue polysaccharides with 46-48% hydrochloric acid. IV. The problem of the limit concentration of sugars in the hydrolyzate. Sbornik Trudov, Vsesoyuznyi Nauchno-Issledovatel'skii Institut Gidroliza Rastitel'nykh Materialov (1965), 13 3-18. CODEN: SVGSAN ISSN: 0371-4322. Abstract only.
Chalov, et al. Continuous hydrolysis of plant tissues with 46-48% hydrochloric acid. VII. Composition of products of hydrolytic destruction of cellulose by concentrated hydrochloric acid. Zhurnal Prikladnoi Khimii (Sankt-Peterburg, Russian Federation) (1967), 40(4), 929-30. CODEN: ZPKHAB ISSN: 0044-4618. Abstract only.
Chalov, et al. Continuous hydrolysis of plant tissues with 46-48% hydrochloric acid. II. Effect of hydrogen chloride on oven-dry wood. Izv. Vysshikh Uchebn. Zavedenii, Lesn. Zh. (1963), 6(2), 141-4. Abstract only.
Chalov, et al. Continuous hydrolysis of wood with 46-48% hydrochloric acid. 1962), 5(No. B), 141-8. CODEN: IVZLAL ISSN: 0536-1036. Abstract only.
Chalov, et al. Differential hydrolysis of wood with concentrated hydrochloric acid in diffusion equipment. 1961), 4(6), 138-46. CODEN: IVZLAL ISSN: 0536-1036. Abstract only.
Chalov, et al. Equilibrium state in the system cellulose-hydrogen chloride-water-hydrolysis products. USSR. Sb. Tr. Vses. Nauch.-Issled. Inst. Gidroliza Rastit. Mater. (1968), 17 173-9. From: Ref. Zh., Khim. 1969, Abstr. No. 15p. 23. Abstract only.
Chalov, et al. Hydrolysis of difficult-to-hydrolyze polysaccharides of wood with 30-6% hydrochloric acid at 20-40.deg. USSR. Sb. Tr. Vses. Nauch.-Issled. Inst. Gidroliza Rast. Mater. (1969), 18 58-66. From: Ref. Zh., Khim. 1970, Abstr. No. 11P29. Abstract only.
Chalov, et al. Hydrolysis of hemicellulose components of pinewood with 30-36% hydrochloric acid at 30-40.deg. Gidroliznaya i Lesokhimicheskaya Promyshlennost (1968), 21(3), 4-6. CODEN: GLKPA2 ISSN: 0016-9706. Abstract only.
Chalov, et al. Hydrolysis of hemicellulose components of pinewood with 30-36% hydrochloric acid. Zhurnal Prikladnoi Khimii (Sankt-Peterburg, Russian Federation) (1961), 34 1601-8. CODEN: ZPKHAB ISSN: 0044-4618. Abstract only.
Chalov, et al. Hydrolysis of lignocellulose with 38-41% hydrochloric acid at 20°. Vysshikh Uchebn. Zavedenii, Lesn. Zh. (1964), 7(2), 137-43. Abstract only.
Chalov, et al. Hydrolysis of pinewood lignocellulose with 41% hydrochloric acid in a [6-] diffuser unit. Izvest. Vysshikh Ucheb. Zavedenii, Lesnoi Zhur. (1961), 4(No. 2), 131-7. Abstract only.
Chalov, et al. Hydrolysis of polysaccharides of pinewood with 38-41% hydrochloric acid at 20°. Zhurnal Strukturnoi Khimii (1962), 35(No. 6), 1347-55. CODEN: ZSTKAI ISSN: 0136-7463. Abstract only.
Chalov, et al. Hydrolysis of polysaccharides of plant fiber in concentrated aqueous and gaseous hydrochloric acid. Zhurnal Prikladnoi Khimii (Sankt-Peterburg, Russian Federation) (1960), 33 2743-50. CODEN: ZPKHAB ISSN: 0044-4618. Abstract only.
Chalov, et al. Hydrolysis of wood with concentrated hydrochloric acid. Gidroliz. i Lesokhim. Prom. (1959), 12(No. 3), 3-5. Abstract only.
Chalov, et al. Hydrolysis of wood with concentrated hydrochloric acid. Gidroliznaya i Lesokhimicheskaya Promyshlennost (1959), 12(No. 4), 1-4. Abstract only.
Chalov, et al. Hydrolysis of wood with gaseous hydrochloric acid under atmospheric pressure. Gidroliznaya i Lesokhimicheskaya Promyshlennost (1959), 12 14-18. Abstract only.
Chalov, et al. Two-stage hydrolysis of wood by use of mechanochemical degradation of lignocellulose in the presence of hydrochloric acid. Sbornik Trudov. Gosudarstvennyi Nauchno-issledovatel'skii Institut Gidroliznoi i Surl'fitno-spirtovoi Promyshlennosti (1966), 15 189-98. CODEN: SGSSAC. Abstract only.
Chalov, et al. Withdrawal of the heat of absorption during hydrolysis of wood with gaseous hydrogen chloride. 1962), 5(No. 1), 155-62. CODEN: IVZLAL ISSN: 0536-1036. Abstract only.
Chalov, Sorption of Hydrogen Chloride by moist lignocellulose. SB. TR. VNII Gidroliza Rastitel'N. Mater. 1975; 25:41-49.
Chambost, et al. Guided tour: Implementing the forest biorefinery (FBR) at existing pulp and paper mills. Pulp & Paper Canada. 2008; 109(7):1-9.
Chandra, et al. Substrate Pretreatment: The Key to Effective Enzymatic Hydrolysis of Lignocellulosics? Adv Biochem Engin/Biotechnol. 2007; 108: 67-93.
Chang, et al. Modification of wood with isopropyl glycidyl ether and its effects on decay resistance and light stability. Bioresource Technology. 2006; 97:1265-1271.
Chaow-U-Thai et al. Removal of ash from sugarcane leaves and tops. International Journal of Biosciences.2012; 2(5): 12-17.
Chen, et al. Application of Molecular Fragments Variable Connectivity Index to Predicting Boiling Points of Alcohols. J. Iran. Chem. Soc. Dec. 2010; 7(4):1012-1020.
Cheng et al. A novel method to prepare L-arabinose from xylose mother liquor by yeast-mediated biopurification. Microbial cell factories.2011; 10 (43): 1-11.
Chevalier, et al. Vapor-Liquid Equilibrium Data for the Systems H2O-H2SO4-HCI, H2O-H2SO4-HBr, and H2O-HBr at 780 mmHg Pressure. J. Chem. Eng. Data. 1980; 25:271-273.
Chidambaram, et al. A two-step approach for the catalytic conversion of glucose to 2,5-dimethylfuran in ionic liquids. Green Chem. 2010; 12: 1254-1262.
Chinese Office action dated Dec. 3, 2014 for CN Application No. 2011800414270.
Choudhary et al. Conversion of Xylose to Furfural Using Lewis and Brønsted Acid Catalysts in Aqueous Media. ASC Catalysis.2012; 2: 2022-2028.
Choudhary et al. Highly efficient aqueaous oxidation of furfural to succinic acid using reusable heterogeneous acid catalyst with hydrogen peroxide. Chem. Lett. 2012; 41: 409-411.
Christiernin. Composition of Lignin in Outer Cell-Wall Layers. Doctoral Thesis, Royal Institute of Technology. 2006.
Ciolacu, et al. New aspects concerning formulation of furan and lignin-based bio-adhesive. 2008.
Claricone Clarifiers and FiltraCone treatment plants. CB&I. Accessed Nov. 30, 2011.
Coetzee, et al. Determination of pectin content of eucalyptus wood. Holzforschung. 2011; 65:327-331.
Cognis. MCT Redbook. Solvent Extraction Reagents and Applications. Cognis miningchemicals technology. 2010.
Cole. XCV. The determination of reducing sugars by titration of ferricyanide. Biochem. 1933 xxvii, pp. 723-726.
Coma, et al. alpha-Glucosidase and N-Acetyl-p-o-glucosaminidase Isoenzymes in Serum. Clin. Chem. 1992; 38(2):223-226.

(56) References Cited

OTHER PUBLICATIONS

Compere, et al. Evaluation of Lignin from Alkaline-Pulped Hardwood Black Liquor. Oak Ridge National Laboratory, US Department of Energy, under contract DE-AC05-000R22725, ORNLITM-2005/88. May 2005.
Compere, et al. Improving the fundamental properties of lignin-based carbon fiber for transportation application. Oak Ridge National Lab. 2009.
Compere, et al. Low cost carbon fiber from renewable resources. Carbon. 1998; 36(7-8):1119-1124.
Conner, et al. Kinetic modeling of hardwood prehydrolysis. Part II. Xylan removal by dilute hydrochloric acid prehydrolysis. Wood and Fiber Science. 1985; 17(4):540-548.
Constantinescu, et al. Composites based on natural and recycled synthetic polymers. 2005.
Constantinescu, et al. Lignin hydrophobization by different esterification reactions. ILI—Forum 8 , May 10-12, 2007.
Constantinescu, et al. Study of the surface properties of some polyolefin/lignocellulosic composites treated by plasma. Cellulose Chem. Technol. 2007; 41(7-8):463-472.
Co-pending U.S. Appl. No. 15/261,560, filed Sep. 9, 2016.
Co-pending U.S. Appl. No. 15/492,319, filed Apr. 20, 2017.
Crittenden, et al. Extraction of hydrogene chloride from aqueous solutions. Industrial and Engineering Chemistry. Feb. 1954; 46(2):265-274.
Cui. Structural Analysis of Polysaccharides. Chapter 3. Copyright 2005 by Taylor & Francis Group, LLC.
Curtis, et al. Equilibria in furfural-water systems under increased pressure and the influence of added salts upon the mutual solubilities of furfural and water. Aus. J. Sci. Res; 1948; 1(2): 213-235.
Dave, et al. Molecular organization of lignin during carbonization. Polymer. 1993; 34(15):3144-3154.
David, et al. 31P-NMR analysis of bio-oils obtained from the pyrolysis of biomass. Biofuels. 2010; 1(6):839-845.
David, et al. Cross-Polarization/Magic Angle Spinning (CP/MAS) 13C Nuclear Magnetic Resonance (NMR) Analysis of Chars from Alkaline-Treated Pyrolyzed Softwood. Energy & Fuels. 2009; 23:498-501.
Dayton, et al. Biomass Hydropyrolysis in a Pressurized Fluidized Bed Reactor. Energy and Fuels.2013; 27: 3778-3785.
De Guzman. Bio-adipic acid prepares for entry. ICIS Chemical Business Sep. 27, 2010. www.icis.com.
De Jong, et al. Lignin as additive in paper production. Agrotechnology & Food Innovations, Wageningenur. Fibre and Paper Technology. Feb. 2005.
De Jong, et al. The simultaneous colouring and U.V. stabilisation of materials using dyed lignin. The international Lignin Institute, 5th international Forum' Sep. 7, 2000, Bordeaux (France).
De Los Rios, et al. Removal of Metal Ions from Aqueous Solutions by Extraction with Ionic Liquids. J. Chem. Eng. Data. 2010; 55:605-608.
De Wild, et al. Pyrolysis of Wheat Straw—Derived Organosolv Lignin. Ch. 5, pp. 101-122. 2011.
De Wild. Lignin Valorisation for Chemicals and Fuels by Catalytic Pyrolysis. International Biomass Valorisation Congress, Amsterdam—The Netherlands, Sep. 13-15, 2010.
Demirbas. Furfural Production from Fruit Shells by Acid-Catalyzed Hydrolysis, Energy Sources, Part A: Recovery, Utilization, and Environmental Effects. 2006; 28(2):157-165.
Demirbas. Products from lignocellulosic materials via degradation processes. Energy Sources, Part A. 2008; 30:27-37.
Diaz, et al. Variations in fiber length and some pulp chemical properties of Leucaena varieties. Industrial Crops and Products. 2007; 26(2): 142-150.
dictionary.com. "Oligosaccharide". Downloaded Mar. 27, 2017. 2 pages.
Dimmel et al. Electron transfer reactions in pulping systems ( II ): electrochemistry of Anthraquinone / Lignin model QUINONEMETHIDES. IPC Thechnical Paper series. 1984; 141: 1-22.
Dimmel, et al. Fundamentals of selectivity in pulping and bleaching: Delignification reactions. Members of the Institute of Paper Chemistry. The Institute of Paper Chemistry. 1986; Project 3475.
Dimmel et al. IPC Technical Paper Series No. 139 Electron Transfer Reactions in Pulping Systems ( I ): Theory and Applicability to Anthraquinone Pulping. 1984; 139: 1-15.
Dimov, et al. Influence of the amount and concentration of hydrochloric acid on the composition of wheat straw during pre-hydrolysis. Chem. Technol. Inst., Sofia, Bulg. Papier (Paris) (1960), 14 673-6. CODEN: PPERA3 ISSN: 0370-1174. Abstract only.
Diouf, et al. Radical Scavenging Capacity of Lignin Derivatives and Its Oxidative Stabilization Effect on Polyethylene. 2008.
Dipardo. Outlook for Biomass Ethanol Production and Demand. Energy Information Administration. 2008; 1-14.
Doorn, et al. CID-Based ICP-AES Instrumantation for Cntinuous On-Line Analysis of Aqueous Industrial Waste Streams. Conference report. 1997; Vancouver (Canada).
Draucker. Novel solvent systems for the development of sustainable technologies. Georgia Institute of Technology. Aug. 2007.
Drenkow. Wood Saccharification. A Modified Rheinau Process. 1976. DouglasDrenkow.com/write2a.html.
Drougge, et al. Application of Kraft lignin as metal binder. 2008.
Duque. Acid-functionalized nanoparticles for hydrolysis of lignocellulosic feedstocks. Master of Science, Department of Biological and Agricultural Engineering, College of Engineering, Kansas State University, Manhattan, Kansas. 2009.
Dutta et al. Direct conversion of cellulose and lignocellulosic biomass into chemicals and biofuel with metal chloride catalysts. Journal of Catalysis; 2012; 288; 8-15.
Dyadic. AlternaFuel® 200P, Product #326, (For considerations in biomass saccharification applications). 2010.
Dyadic. Enzyme Development for Fuel Ethanol Production from Pre-treated Biomass, Technical Report May 2010, Saccharification I.D: Sacc May 17, 2010.
Eckert, et al. Tunable solvents for fine chemicals from the biorefinery. Green Chem. 2007; 9: 545-548.
Economy, et al. Activated carbon fibers—past, present, and future. 1996; 321-358.
Eggeman, et al. Process and economic analysis of pretreatment technologies. Bio. Tech. 2005; 96:2019-2025.
Ehara, et al. A comparative study on chemical conversion of cellulose between the batch type and flow type systems in supercritical water. Cellulose. 2002; 9:301-311.
Elhanan, et al. Solvent Sublation of Iron( III) Chloride by Tri-n-Octylamine. Analytical chemistry. Apr. 1969; 40(4):671-674.
Elliott, et al. Pretreatment technologies for advancing anaerobic digestion of pulp and paper biotreatment residues. Water Research. 2007; 41:4273-4286.
Eminov et al. Highly selective and near-quantitative conversion of fructose to 5-hydroxymethylfurfural using mildly acidic ionic liquids. ACS Sustainable Chemistry & Engineering; 2014; 1-17.
Encyclopaedia Britannica. Biochemistry. "Oligosaccharide". Downloaded Mar. 27, 2017. 1 page.
Esteves, et al. Chemistry and ecotoxicity of heat-treated pine wood extractives. Wood Sci Technol. Jul. 11, 2010. DOI 10.1007/s00226-010-0356-0.
European search report dated May 4, 2015 for EP Application No. 12768483.5.
European search report dated Sep. 11, 2015 for EP Application No. 11797729.8.
European search report dated Oct. 9, 2015 for EP Application No. 12768483.5.
Excoffier, et al. Saccharification of Steam-Exploded Poplar Wood. Biotechnology and bioengineering. Dec. 20, 1991; 38(11):1308-1317.
Extended European search report dated Jan. 20, 2016 for EP Application No. 11797729.8.
Eyal, et al. A process for defluorination and purification of wet process phosphoric acids containing high al concentrations. Solvent Extraction and ion exchange. 1984; 2(4):677-697.
Eyal, et al. Extraction of Strong Mineral Acids by Organic Acid-Base Couples. Ind. Eng. Chem. Process Des. Dev. 1982, 21, 334-337.

(56) References Cited

OTHER PUBLICATIONS

Eyal, et al. pH dependence of carboxylicand mineral acid extraction by amine-based extractants: effects of pKa, Amine Basicity, and diluent properties. Ind. Eng. Chem. Res. 1995; 34:1789-1798.

Eyal, et al. Potassium Nitrate through Solvent Separation of Strong Acids. Ind. Eng. Chem. Process Des. 1985; 24:387-390.

Eyal, et al. Recovery and concentration of strong mineral acids from dilute solutions through LLX.I: review of parameters for adjusting extractant propert and analysis of process options. Solvent Extraction and ion exchange. 1991; 9(2):195-210.

Eyal, et al. Sulfuric acid recovery through solvent aided decomposition of ammonium sulfate. Solvent Extraction and ion exchange. 1986; 44:803-821.

Eyal, et al. Wet process phosphoric acid defluorination by aminebased extractants. Solvent Extraction and ion exchange. 1984; 2(4&5):659-675.

Fahim, et al. Liquid-Liquid Equilibria of the Ternary System Water + Acetic Acid + 1-Hexanol. J. Chem. Eng. Data. 1997; 42:183-186.

Farrell, et al. Solving Pitch Problems in Pulp and Paper Processes by the Use of Enzymes or Fungi. Advances in Biochemical Engineering/Biochemical Engineering/1997/pp. 198-212.

Feldman, et al. Lignin in blends with synthetic polymers. 2007.

Fenner, et al. Examination of the Thermal Decomposition of Kraft Pine Lignin by Fourier Transform Infrared Evolved Gas Analysis. J. Agric. Food Chem. 1981; 29:846-849.

Ferrari, et al., Ethanol production from eucalyptus wood hemicellulose hydrolysate by pichia stipitis, 1992, biotech and bioengineering, 40:753-759.

Ferraz, et al. Estimating the chemical composition of biodegraded pine and eucalyptus wood by DRIFT spectroscopy and multivariate analysis. Bioresource Technology. 2000; 74:201-212.

Fierro, et al. Methodical study of the chemical activation of Kraft lignin with KOH and NaOH. Microporous and Mesoporous Materials. 2007; 101:419-431.

Foran, et al. Beyond 2025: Transitions to the biomass-alcohol economy using ethanol and methanol. Working Paper Series 99/07. Dec. 1999.

Fox. Chemical and thermal charaterization of three industrial lignins and their corresponding lignin esters. A Thesis for the degree of Master of Science with a Major in Forest Products in the College of Graduate Studies University of Idaho, May 2006.

Foxit. Chemicals partition in wood. Mar. 2011.

Froass, et al. Nuclear Magnetic Resonance Studies. 4. Analysis of Residual Lignin after Kraft Pulping. Ind. Eng. Chem. Res. 1998; 37:3388-3394.

Funaoka, et al. Design and functions of structure controllable lignin-based polymers. 2005.

Fungsin, et al. Conversion of cassava waste into sugar using Aspergillus niger and Trichoderma reesei for ethanol production. 2010.

Gabilondo, et al. Lignin low molar mass fractions involvement in the synthesis of PF matrices. 2007.

Galbe, et al. A review of the production of ethanol from softwood. Appl Microbiol Biotechnol. 2002; 59:618-628.

Galbe, et al. Process Engineering Economics of Bioethanol Production. Adv Biochem Engin/Biotechnol. 2007; 108:303-327.

Galego, et al. Mechanism of the thermal resinification of pure furfural . Revista CENIC, Ciencias Fisicas. 1975; 6(1):163-180. Abstract only.

Gamez et al. Study of the hydrolysis of sugar cane bagasse using phosphoric acid. Journal of Food Engineering.2006; 74: 78-88.

Gani et al. Molecular Design of Solvents for Liquid Extraction Based on UNIFAC. Fluid Phase Equilibria. 1983; 13: 331-340.

Garna, et al. Kinetic of the hydrolysis of pectin galacturonic acid chains and quantification by ionic chromatography. Food Chemistry. 2006; 96:477-484.

Gaspar, et al. Oxidaton of Lignin in supercritical carbon dioxide. III meeting, Barcelona, Apr. 27-28, 2005.

Genencor. Enzyme Products for Fuel Ethanol Production. Genencor, 2007 Danisco US Inc.

Georgieva, et al. Enzymatic hydrolysis and ethanol fermentation of high dry matter wet-exploded wheat straw at low enzyme loading. Applied biochemistry and biotechnology. 2008;148:35-44.

Georgopoulos, et al. Thermoplastic polymers reinforced with fibrous agricultural residues. 2009.

Gibbs et al. An Economic Value Chain Using Nonfood Biomass Intermediates for Bioplastics Production. Presentation; General Biomass Company; 2013.

Glasser. Lignin retrospect and prospect. 2010.

Glazkova, et al. Effect of temperature on the extraction of prehydrolysis products from lignocellulose chips. Gidroliznaya i Lesokhimicheskaya Promyshlennost (1974), (6), 12-13. CODEN: GLKPA2 ISSN: 0016-9706. Abstract only.

Goldstein, et al. The hydrolysis of cellulose with superconcentrated hydrochloric acid. Biotechnology and Bioengineering Symposium (1984), vol. Date 1983, 13(Symp. Biotechnol. Fuels Chem., 5th, 1983), 17-25. CODEN: BIBSBR ISSN: 0572-6565. Abstract only.

Goldstein. Potential for Converting Wood into Plastics, Chemicals from wood may regain importance as the cost of petroleum continues to rise. SCIENCE, Sep. 12, 1975; 189(4206):847-852.

Goncalves, et al. Hydroxymethylation and oxidation of Organosolv lignins and utilization of the products. Bioresource Technology. 2001; 79:103-111.

Gonzalez-Serrano, et al. Development of Porosity upon Chemical Activation of Kraft Lignin with ZnCl2. Ind. Eng. Chem. Res. 1997; 36:4832-4838.

Gonzalez-Serrano, et al. Removal of water pollutants with activated carbons prepared from H3PO4 activation of lignin from kraft black liquors. Water Research. 2004; 38:3043-3050.

Gosselink, et al. Analysis of isolated lignin samples using organic and alkaline SEC and MALDI-TOF-MS. Agrotechnology & Food Sciences Group. 2006.

Gosselink, et al. Analytical protocols for characterisation of sulphur-free lignin. Industrial Crops and Products. 2004; 19:271-281.

Gosselink, et al. Characterisation and application of NovaFiber lignin. Industrial Crops and Products. 2004; 20:191-203.

Gosselink, et al. Co-ordination network for lignin—standardisation, production and applications adapted to market requirements (EUROLIGNIN). Industrial Crops and Products 2004; 20:121-129.

Gosselink, et al. Development of lignin based products. Canada Biomass Business Day, Amstelveen (NL), Oct. 22, 2008.

Gosselink, et al. FT-IR characterisation of lignins with help of PCA. Cost E41 Spectrometric techniques used for the analysis of Carbohydrates, Lignin and Extractives Barcelona, Apr. 25 26, 2005.

Gosselink, et al. Lignin depolymerization under supercritical process conditions. Agrotechnology & Food Sciences Group. 2008.

Gosselink, et al. Selective oxidation of lignin by periodate. ILI 8th Forum May 11, 2007 May 10-12, 2007.

Gosselink, et al. Valorization of biorefinery lignins. ILI Lignin workshop, Zurich/Dubendorf (CH), Oct. 28, 2008.

Gosselink, et al. Valorization of lignin resulting from biorefineries. Jun. 4, 2008, RRB4 Rotterdam.

Goto, et al. Supercritical Thermal Decomposition of Cellulose: Experiments and Modeling. Ind. Eng. Chem. Res. 1990; 29:1091-1095.

Grant, et al. Tall oil production and processing. Grant and Hockh's Chemical Dictionary 5th ed. 1987.

Gray, et al. Sugar Monomer and Oligomer Solubility, Data and Predictions for Application to Biomass Hydrolysis. Applied Biochemistry and Biotechnology. 2003; 105-108:179-193.

Górecka, et al. The application of ICP-MS and ICP-OES in determination of micronutrients in wood ashes used as soil conditioners. Talanta. Dec. 15, 2006;70(5):950-6.

Greenwald. The dissociation of some calcium salts. Mar. 7, 1938; 437-452.

Grethlein, et al. The Cost of Ethanol Production from Lignocellulosic Biomass—A Comparison of Selected Alternative Processes . USDA. Specific Cooperative Agreement No. 58/1935-2-050. Apr. 30, 1993.

Gretland, et al. Characterisation of lignosulphonates and sulphonated kraft lignin by hydrophobic interaction chromatography. 2005.

Griffith, et al. Low cost carbon fiber for transportation application. USDE. 2003.

(56) References Cited

OTHER PUBLICATIONS

Grigoriev, et al. Polyoxometalate Oxidation of Phenolic Lignin Models. In: ACS Symposium Series 785. Oxidative delignification chemistry. Fundamentals and catalysis. Washington, DC: American Chemical Society. 2001; Chapter 18: 297-312.
Grinbaum. An Integrated method for Development and Scaling up of Extraction Processes. "Ion Exchange and Solvent Extraction", Y. Marcus, A. Sangupta (eds.), vol. 15, Elsevier, 2002.
Guerra, et al. On the Propensity of Lignins to Associate. Organic Chemistry of Wood Components Laboratory Department of Forest Biomaterials Science & Engineering North carolina State Raleigh, North Carolina USA. 2007.
Guirguis, et al. Purification of phosphoric acid by a mixture of hydrophobic and hydrophilic extractants. Adv. Process. Met. Mater., Sohn Int. Sym. 2006; 3:451-465.
Gutierrez, et al. Analysis of Lipophilic extractives from wood and pitch deposits by solid-phase extraction and gas chromatography. J. of Chromatography A. 1998; 823:449-455.
Gutierrez, et al. Enzymatic Removal of Free and Conjugated Sterols Forming Pitch Deposits in Environmentally Sound Bleaching of Eucalypt Paper Pulp. Environ. Sci. Technol. 2006; 40:3416-3422.
Gutierrez, et al. Fungal Degradation of Lipophilic Extractives in Eucalyptus globulus Wood. Applied and environmental microbiology. Apr. 1999; 65(4):1367-1371.
Gutierrez, et al. Microbial and enzymatic control of pitch in the pulp and paper industry. Appl Microbiol Biotechnol. 2009; 82:1005-1018.
Gutierrez, et al. The biotechnological control of pitch in paper pulp manufacturing. Trends in Biotechnology. 2001; 19(9):340-348.
Haensel, et al. Pyrolysis of wood-based polymer compounds. J. Anal. Appl. Pyrolysis. 2010; 87:124-128.
Hage, et al. Effects of process severity on the chemical structure of Miscanthus ethanol organosolv lignin. Polymer Degradation and Stability. 2010; 95:997-1003.
Hagglund. Hydrochloric acid lignin (preliminary communication). Berichte der Deutschen Chemischen Gesellschaft [Abteilung] B: Abhandlungen (1923), 56B 1866-8. CODEN: BDCBAD ISSN: 0365-9488. Abstract only.
Hagglund. Report of the research activities of the Cellulose Laboratory (Stockholm, Sweden) during the year 1941. Svensk Papperstidning (1942), 45 123-35. Abstract only.
Hagglund. The Decomposition of Wood by Acids wood Saccharification. Chemistry of Wood. New York: Academic Press, 1951. 631. Chapter IV. 390-413.
Hagglund. Wood Saccharification. A Modified Rheinau Process. 2011.
Hall, et al. Wood saccharification. USDA. Unasylva. 2007; 10(1).
Hall. Polyhydric alcohol from wood. US Department of Agriculture, Forest Service, Forest Products Laboratory, Madison, Wisconsin. No. 1984. Jul. 1954.
Hallac, et al. Biomass Characterization and Organosolv Pretreatment of Buddleja davidii. School of Chemistry and Biochemistry, Institute of Paper Science and Technology, Georgia Institute of Technology, Atlanta, GA. 2009.
Hallac, et al. Biomass Characterization of Buddleja davidii: A Potential Feedstock for Biofuel Production. J. Agric. Food Chem. 2009; 57(4):1275-1281.
Hallac, et al. Chemical Transformations of Buddleja davidii Lignin during Ethanol Organosolv Pretreatment. Energy Fuels. 2010; 24:2723-2732.
Hallac. Fundamental understanding of the biochemical conversion of buddleja davidii to fermentable sugars. Georgia Institute of Technology. May 2011.
Hallac. Lignin, a crash course. Dec. 23, 2009. Powerpoint.
Hallal et al. Electrochemical polymerization of furfural on a platinum electrode in aqueous solutions of potassium biphthalate. Materials Research; 2005; 8(1); 23-29.
Hamelinck, et al. Ethanol from lignocellulosic biomass: techno-economic performance in short-, middle- and long-term. Biomass and Bioenergy; 2005; 28; 384-410.
Hamelinck, et al. Production of advanced biofuels. International Sugar Journal. 2006; 108(1287):168-175.
Han, et al. Optimizing lignocellulosic feedstock for improved biofuel productivity and processing. Biofuels, Bioprod. Bioref. 2007; 1:135-146.
Hanchar, et al. Separation of glucose and pentose sugars by selective enzyme hydrolysis of AFEX-treated corn fiber. Appl Biochem Biotechnol. Apr. 2007;137-140(1-12):313-25. doi: 10.1007/s12010-007-9061-3.
Harada, et al. Formation of Isoamylase by Pseudomonas. Applied Microbiology. Oct. 1968; 16(10):1439-1444.
Harris. Derived products and chemical utilization of wood waste. Forest Products Laboratory; Forest Service US Department of Agriculture; Rept. No. R1666-10. Jun. 1949.
Harris, et al. Hydrolysis of wood cellulose with hydrochloric acid and sulfur dioxide and the decomposition of its hydrolytic products. Journal of Physical and Colloid Chemistry. (1949), 53:344-51. Abstract only.
Harris, et al. The Madison Wood-Sugar Process. US Dept. of Agriculture. Jun. 1946; 1-21.
Harris. Progress in the Chemistry of Lignin 1943-1954, Report No. 2020. USDA. Mar. 1955.
Harrison. CLVII. A note on the solubilities of calcium soaps. 1924; 1222-1223.
Hasegawa, et al. New Pretreatment Methods Combining a Hot Water Treatment and Water/Acetone Extraction for Thermo-Chemical Conversion of Biomass. Energy & Fuels. 2004; 18:755-760.
Hatch, et al. acid retardation, A Simple Physical Method for Separation of Strong Acids from Their Salts. I & E C process design and development. Oct. 1963; 2(4):253-263.
Hatcher. Chemical structural studies of natural lignin by dipolar dephasing solid-state $^{13}$C nuclear magnetic resonance. Org. Geochem. 1987; 11(1):31-39.
Hatcher. Dipolar-Dephasing $^{13}$C NMR Studies of Decomposed Wood and Coalified Xylem Tissue:Evidence for Chemical Structural Changes Associated with Defunctionalization of Lignin Structural Units during Coalification. Energy. Fuels. 1988; 2:48-58.
Havlik, et al. Atmospheric leaching of EAF dust with diluted sulphuric acid. Hydrometallurgy. 2004; doi:10.1016/j.hydromet.2004.10.008.
Hawley, et al. Comparison of hydrogen fluoride saccharification of lignocellulosic materials with other saccarification technologies. Energy in Agriculture. 1983; 2:219-244.
Hayashi, et al. Preparation of activated carbon from lignin by chemical activation. Carbon. 2000; 38:1873-1878.
Hayes, et al. The Biofine Process: Production of Levulinic Acid, Furfural and Formic Acid from Lignocellulosic Feedstocks. Biorefinery (8b). 2011.
Heinonen, et al. Chromatographic recovery of monosaccharides for the production of bioethanol from wood. Ind. Eng. Chem. Res. 2010; 49:2907-2915.
Held. Catalytic conversion of renewable plant sugars to fungible liquid hydrocarbon fuels using the bioforming process. TAPPI IBBC session 3. Virent Energy systems. Oct. 15, 2009.
Hellenbrand et al. Integration of Wet Oxidation and Nanofiltration for Treatment of Recalcitrant Organics in Wastewater. Kinetic, Catalysts and Reaction Engineering; 1997; 36;5054-5062.
Hendriks, et al. Pretreatments to enhance the digestibility of lignocellulosic biomass. Bioresource Technology. 2009; 100:10-18.
Heppolette, et al. Effect of a-methylation on the parameters characterizing hydrolysis in water for a series of halides and sulfonates. Canadian Journal of Chemistry. 1966; 44:677-684.
Hergert. Infrared Spectra of Lignin and Related Compounds.11 Conifer Lignin and model compounds—Hergert in J. Org. Chem. 1960; 25:405-413.
Hernadez, et al. Role of lignin structure in foams formations and their stability. 2007.
Herrera, et al. Effect of the hydrochloric acid concentration on the hydrolysis of sorghum straw at atmospheric pressure. Journal of Food Engineering.2004; 63:103-109.
Herrera, et al. Production of Xylose from Sorghum Straw Using Hydrochloric Acid. Journal of Cereal Science. 2003; 37:267-274.

(56) References Cited

OTHER PUBLICATIONS

Herty. Advanced Materials Development Center. HCI Clean Tech Composite Sample—Extracted Wood Sample. 2010.

Hettenhaus et al. Cellulase Assessment Report and Recommendations for Future Work. Ethanol Production from Biomass Hydrolysis; NREL report; 1997.

Heuts, et al. Chrysosporium lucknowense cellulase production platform for applications in biorefineries. DYADIC® Netherlands. 2010.

Higgins, et al. Hydrolysis of cellulose using HCL: A comparison between liquid phase and gaseous phase processes. Agricultural wastes. 1982; 4:97-116.

Hinz, et al. Hemicellulase production in Chrysosporium lucknowense C1. Journal of Cereal Science. 2009; 50(3):318-323. doi:10.1016/j.jcs.2009.07.005.

Hirst, et al. CCCLXXXII.—The action of highly concentrated hydrochloric acid on cellulose and on some derivatives of glucose and of xylose. 1923; 3226-3235.

Hiwale, et al. Industrial Applications of Reactive Distillation: Recent Trends. International Journal of Chemical Reactor Engineering, vol. 2 [2004], Review R1. 1-54.

Hoareau et al. Sugar cane bagasse and curaua lignins oxidized by chlorine dioxide and reacted with furfuryl alcohol : characterization and stability. Polymer Degradation and Stability. 2004; 86: 567-576.

Hodge. Chemistry of Browning Reactions in Model Systems. Agricultural and Food Chemistry. Oct. 14, 1953; 1(15):928-943.

Holladay, et al. Top Value-Added Chemicals from Biomass vol. II—Results of Screening for Potential Candidates from Biorefinery Lignin. Pacific Northwest National Laboratory, Prepared for the U.S. Department of Energy. Oct. 2007.

Holm, et al. Ionic Liquids in the Pretreatment of Lignocellulosic Biomass. chapter 24, 545-560. 2011.

Holota, et al. One-stage hydrolysis of beechwood sawdust by gaseous hydrogen chloride. Vyskum (1967), (2), 105-18. CODEN: DRVYAP ISSN: 0012-6136. Abstract only.

Holtman, et al. An NMR Comparison of the Whole Lignin from Milled Wood, MWL, and REL Dissolved by the DMSO/NMI Procedure. Journal of Wood Chemistry and Technology. 2007; 27:179-200.

Holtman, et al. Quantitative 13C NMR Characterization of MWL isolated by milling techniques. J Wood Chem Technol. 2006; 26:21-34.

Horsley, et al. Azeotropic Data-II, No. 35, Advances in Chemistry Series. American Chemical Society, Washington, D.C. 1962.

Horvath, et al. IUPAC-NIST Solubility Data Series 68. Halogenated Aliphatic Hydrocarbon Compounds C3-C1 With Water. J. Phys. Chem. Ref. Data. 1999; 28(3):649-777.

Hou-Rui, et al. Novel Isolates for Biological Detoxification of Lignocellulosic Hydrolysate. Appl Biochem Biotechnol 2009; 152:199-212.

Howarth, et al. Methane and the greenhouse-gas footprint of natural gas from shale formations, A letter. Climatic Change, Accepted: Mar. 13, 2011, DOI 10.1007/s10584-011-0061-5.

Hu, et al. Chemical profiles of switchgrass. Bioresource Technology. 2010; 101:3253-3257.

Huang, et al. A review of separation technologies in current and future biorefineries. Separation and Purification Technology. 2008; 62:1-21.

Huber. Breaking the Chemical and Engineering Barriers to Lignocellulosic Biofuels: Next Generation. Based on the: Jun. 25-26, 2007 ,Workshop, Washington D.C.

Huber, et al. Synthesis of Transportation Fuels from Biomass: Chemistry, Catalysts, and Engineering. Chemical Reviews. Published on Web Jun. 27, 2006 Page EST: 54.3, 10.1021/cr068360d.

Hutchins, et al. Aqueous polar aprotic solvents. Efficient sources of nucleophilic oxygen. J. Org. Chem. 1983; 48:1360-1362.

Hyttinen, et al. Comparison of VOC emissions between air-dried and heat-treated Norway spruce (*Picea abies*), Scots pine (*Pinus sylvesteris*) and European aspen (*Populus tremula*) wood. Atmospheric Environment. 2010; 44:5028-5033.

Ibarra, et al. Isolation of high-purity residual lignins from eucalypt paper pulps by cellulase and proteinase treatments followed by solvent extraction. Enzyme and Microbial Technology. 2004; 35:173-181.

IBBC. Sequential Lignin Recovery & Purification (SLRP). Poster Session at the IBBC/BioPro Expo Mar. 14-16, 2011.

Ibrahim, et al. Comparison of alkaline pulping with steam explosion for glucose production from rice straw. Carbohydrate Polymers. 2011; 83:720-726.

IntechFibres. Microscopic Analysis of pulps, papers and boards: For a Fundamental Knowledge of Fibre Structure. IntechFibers, research in fibers Nov. 2007.

International search report and written opinion dated Mar. 9, 2012 for PCT/IL2011/000509.

International search report and written opinion dated May 23, 2012 for PCT Application No. U.S. Appl. No. 12/024,033.

International search report and written opinion dated Jul. 18, 2012 for PCT/IB2011/003310.

International search report and written opinion dated Aug. 31, 2012 for PCT/IL2012/050118.

Iranmahboob, et al. Optimizing acid-hydrolysis: a critical step for production of ethanol from mixed wood chips. Biomass and Bioenergy. 2002; 22:401-404.

IsoClear 42% high fructose 80% solids corn syrup. Technical product information. Cargill. Updated Aug. 14, 2012.

Itzkowitz. Biodiesel from sugars. 2011.

Izydorczyk, et al. Polysaccharide Gums: Structures, Functional Properties, and Applications. Chapter 6. Copyright 2005 by Taylor & Francis Group, LLC.

Izydorczyk. Understanding the Chemistry of Food Carbohydrates. Chapter 1. Copyright 2005 by Taylor & Francis Group, LLC.

Jacobsen, et al. Cellulose and Hemicellulose Hydrolysis Models for Application to Current and Novel Pretreatment Processes. Applied Biochemistry and Bio. 2000; 84-86:81-96.

Jacobsen et al. Xylose Monomer and Oligomer Yields for Uncatalyzed Hydrolysis of Sugarcane Bagasse Hemicellulose at Varying Solids Concentration. Industrial & Engineering Chemistry Research; 2002; 41; 1454-1461.

Jiang, et al. Perdeuterated pyridinium molten salt (ionic liquid) for direct dissolution and NMR analysis of plant cell walls. Green Chem. 2009; 11:1762-1766.

Johannis. Rhenium- and molybdenum-catalyzed Dehydration Reactions. PhD Thesis. Utrecht University, The Netherlands, 1984.

Johnson. Effects of Dilute Acid Hydrolyzate Components on Glucose Degradation. National Bioenergy Center, NREL, 1617 Cole Blvd., Golden, Colorado 80401, USA. 2011.

Johnson, et al. Stability Patterns of Methoxy Phenols under Alkaline Hydrolysis Conditions. 2011.

Johnson, et al. Use of lignin in the biorefinery. 7th International Forum of the International Lignin Institute,Barcelona, Spain, Apr. 27-28, 2005.

Kadam, et al. Generating Process and Economic Data Needed for Preliminary Design of PureVision Biorefineries. DOE Project No. DE-FG36-05GO85004, Final Nonproprietary Technical Report. Dec. 28, 2007.

Kadla, et al. Lignin-based carbon fibers for composite fiber applications. Carbon. 2002; 40:2913-2920.

Kaewwongsa, et al. Intestinal digestibility of the residual components of cassava pulp solid state fermentation by *Saccharomyces cerevisiae*. Suranaree J. Sci. Technol. 2009; 16(4):291-296.

Kamm, et al. Chemical and biochemical generation of carbohydrates from lignocellulose-feedstock (Lupinus nootkatensis)—quantification of glucose. Chemosphere. 2006; 62:97-105.

Kamm, et al. Definition and technical status of Biorefineries. BioreFuture 2008, Tuesday Feb. 12, 2008, Brussels.

Kamm et al. Internationale Bioraffinerie-Systeme Internationale Bioraffinerie-Systeme. Presentation; Brandenburgische Technische Universitat Cottbus; Frankfurt; 2006.

Karinen et al. Biorefining: heterogeneously catalyzed reactions of carbohydrates for the production of furfural and hydroxymethylfurfural. ChemSusChem; 2011; 4; 1002-1016.

(56) References Cited

OTHER PUBLICATIONS

Katzen, et al. A View of the History of Biochemical Engineering. Advances in Biochemical Engineering/Biotechnology. 2000; 70:77-91.

Kauko. Similarity of the action of hydrochloric acid upon cellulose and humus. Ann. acad. sci. Fennicae (1927), 26A(No. 15), 3-7. Abstract only.

Kauper. Sulfur-free lignin from alkaline pulping as emulsifiers. The international Lignin Institute, 5th international Forum' Sep. 7, 2000, Bordeaux (France).

Keller, et al. Microbial Pretreatment of Biomass, Potential for Reducing Severity. Applied Biochemistry and Biotechnology. 2003; 105-108:27-41.

Khan, et al. Kinetic Study on Palm Oil Waste Decomposition. Biofuel's Engineering Process Technology. 2011. Chapter 22, pp. 523-536.

Khan, et al. PROTOBIND 1075—An Indigenous Economical and Eco-friendly Renewable Raw Material for the Plywood Industry. 2011.

Khezami, et al. Production and characterisation of activated carbon from wood components in powder: Cellulose, lignin, xylan. Powder Technology. 2005; 157:48-56.

Kim, et al. Continuous Countercurrent Extraction of Hemicellulose from Pretreated Wood Residues. Applied Biochemistry and Biotechnology. 2001; 91-93:253-267.

Kim, et al. Enzyme hydrolysis and ethanol fermentaion of liquid hot water and AFEX pretreated distillers' grains at high-solid loadings. Bio. Tech. 2008; 99:5206-5215.

Kim, et al. Pretreatment and fractionation of corn stover by ammonia recycle percolation process. Bioresource Technology. 2005; 96:2007-2013.

Kim, et al. Pretreatment of Corn Stover by Low-Liquid Ammonia Recycle Percolation Process. Applied Biochemistry and Biotechnology. 2006; 133:41-57.

Kim, et al. Supercritical CO2 pretreatment of lignocellulose enhances enzymatic cellulose hydrolysis. Bioresource Technology. 2001; 77:139-144.

Kimberley, et al. A colorimetric method for the quantitation of galacturonic acid. Applied biochemistry and biotechnology. 1993; 43:51-54.

Kinders, et al. Saccharification of HCl-treated substrate provided by HCL-Cleantech, Technical Report, Mar. 2010. Dyadic International Inc. // Confidential and Proprietary Information.

Kindsigo et al. Degradation of lignins by wet oxidation : model water solutions. Proc. Estonian Acad. Sci. Chem.; 2006; 55(3); 132-144.

Kintner III, et al. Carbohydrate Interference and Its Correction in Pectin Analysis Using the m-Hydroxydiphenyl Method. Journal of Food Science. 1982; 47:756-759.

Kireble, et al. The Electromotive Force Measurements of Hydrochloric Acid Solutions with and without Sucrose and their Relation to the Rate of Sucrose Hydrolysis. Chemical Laboratory of Trinity college. Jan. 1935; 57:19-22.

Kjellstrand, et al. Development of toxic degradation products during heat sterilization of glucose-containing fluids for peritoneal dialysis: influence of time and temperature. Perit Dial Int. 1995;15(1):26-32.

Klein, et al. Modelling of lignin thermolysis. MIT. 1981; 77-88.

Kobayashi, et al. A continuous process for the synthesis of hexyl beta-D-glucoside in aqueous phase using immobilized-glucosidase and with 1-hexanolextractive product recovery. Biotechnology Letters. 2000; 22:1845-1848.

Kobayashi, et al. Synthesis of alkyl glycosides through b-glucosidase-catalyzed condensation in an aqueous-organic biphasic system and estimation of the equilibrium constants for their formation. Journal of Molecular Catalysis B: Enzymatic. 2000; 11:13-21.

Kokol. Enzymatic functionalisation of fibre forming polymers using lignin substrates. Institute of Engineering Materials and Design, University of Maribor, Smetanova ul. 17, SI-2000 Maribor, Slovenia. 2008.

Kokol. Maribor Enzymatic functionalisationof fibre-forming polymers using lignin substrates. COST 50E / ILI workshop, Oct. 27-29, 2008, Dubendorf, Switzerland.

Konn et al. Chemical Reactions in Chemimechanical Pulping : Material Balances of Wood Components in a CTMP Process. Journal of pulp and paper science; 2002; 28; 395-399.

Koplan, et al. Certain Activated Carbon From China. U.S. International Trade Commission, Investigation No. 731-TA-1103 (Preliminary), Publication 3852, May 2006.

Korotkov, et al. Continuous hydrolysis of plant tissues with 46-48 hydrochloric acid. VI. The effect of heat on wood saturated with gaseous hydrogen chloride, with simultaneous increase of the partial pressure of hydrogen chloride. Sbornik Trudov, Vsesoyuznyi Nauchno-Issledovatel'skii Institut Gidroliza Rastitel'nykh Materialov (1965), 14 180-91. Abstract only.

Koski. Applicability of crude tall oil for wood protection. Acta Univ. Oul. C 293, 2008, OULUN YLIOPISTO, OULU 2008.

Kosswig, et al. A new Process for Obtaining Hydrogen Chloride from Dilute Hydrochloric Acid. Chemical Economy & Engineering Review. Jun. 1983; 15(6)(No. 169):30-33.

Koullas, et al. Analytical methods for lignin characterization—differential scanning calorimetry. Cellulose Chem. Technol. 2006; 40(9-10):719-725.

Kovalev, et al. Reaction of sprucewood pulp with hydrogen chloride dissolved in dichloroethane. Sbornik Trudov Ukrainskogo Nauchno-IssledovateIskogo Instituta Tsellyulozno-Bumazhnoi Promyshlennosti (1966), No. 9 51-69. CODEN: SUTBAU ISSN: 0453-8560. Abstract only.

Kozlowski, et al. The role of high dispersion lignin in creation of UV protection in textiles. 8 Forum ILI, Rome, 2007.

Krall, et al. Pectin Hydrolysis: Effect of Temperature , Degree of Methylation, pH, and Calcium on Hydrolysis Rates. J. Agric. Food Chem. 1998; 46:1311-1315.

Kubo, et al. Lignin-based Carbon Fibers: Effect of Synthetic Polymer Blending on Fiber Properties. Journal of Polymers and the Environment. Apr. 2005; 13(2):97-105.

Kubo, et al. Poly(Ethylene Oxide)/Organosolv Lignin Blends: Relationship between Thermal Properties, Chemical Structure, and Blend Behavior. Macromolecules. 2004; 37:6904-6911.

Kubo, et al. Preparation of carbon fibers from softwood lignin by atmospheric acetic acid pulping. Carbon. 1998; 36(7-8):1119-1124.

Kubo, et al. Surface Porosity of Lignin/PP Blend Carbon Fibers. Journal of Wood Chemistry and Technology. 2007; 27: 257-271.

Kubo, et al. Thermal Decomposition Study of Isolated Lignin Using Temperature Modulated TGA. Journal of Wood Chemistry and Technology. 2008; 28(2):106-121.

Kucuk, et al. Biomass Conversion Processes. Energy Conyers. Mgmt. 1997; 38(2):151-165.

Kumar, et al. Effect of Enzyme Supplementation at Moderate Cellulase Loadings on Initial Glucose and Xylose Release From Corn Stover Solids Pretreated by Leading Technologies. Biotechnology and Bioengineering. Feb. 1, 2009; 102(2):457-567.

Kumar, et al. Methods for Pretreatment of Lignocellulosic Biomass for Efficient Hydrolysis and Biofuel Production. Ind. Eng. Chem. Res. 2009; 48:3713-3729.

Kunamneni, et al. Fungal laccase—a versatile enzyme for biotechnological applications. Communicating Current Research and Educational Topics and Trends in Applied Microbiology. 2007; 233-245.

Kunkes, et al. Catalytic conversion of biomass to monofunctional hydrocarbons and targeted liquid-fuel classes. Science. Oct. 17, 2008;322(5900):417-21. doi: 10.1126/science.1159210. Epub Sep. 18, 2008.

Kusama, et al. Wood saccharification by gaseous hydrogen chloride. Chisso Corp., Tokyo, Kogyo Kagaku Zasshi. 1966. Parts 1-V and VIII. Abstracts only.

Laine. Structures of hemicelluloses and pectins in wood and pulp. degree of Doctor of Science, Helsinki University of Technology,Department of Chemical Technology, Laboratory of Organic Chemistry, Espoo, Finland, 2005.

Lake. A radically-new *liquid*-lignin recovery and purification process. TechLake & Associates LLC. Feb. 25, 2010.

Lake. Potential Commercial uses for lignin. Southeastern Bioenergy Confrence, Tifton GA, Aug. 4, 2010.

(56) References Cited

OTHER PUBLICATIONS

Lake. Potential Commercial uses for lignin. TechLake & Associates LLC, Presentation to BDC, Durham NC, Oct. 2, 2009.
Lam, et al. Kinetic Modeling of Pseudolignin Formation in Steam Exploded Woody Biomass. 2011.
Lam. Steam explosion of biomass to produce durable wood pellets. The University of British Columbia (Vancouver). May 2011.
Lange, et al. Lignocellulose conversion: an introduction to chemistry, process and economics. Biofuels, Bioprod. Bioref. 2007; 1:39-48.
Lapan, et al. Hydrochloric and sulfuric acid hydrolyzates of fir wood. Izvestiya Nauchno-Issledovatel'skogo Instituta Nefte-i Uglekhimicheskogo Sinteza pri Irkutskom Universitete (1970), 12 102-4. CODEN: INEUBO ISSN: 0367-9195. Abstract only.
Lavarack, et al. The acid hydrolysis of sugarcane bagasse hemicellulose to produce xylose, arabinose, glucose and other products. Biomass and Bioenergy. 2002; 23:367-380.
Lebedev, et al. Hydrolysis of cellulose with concentrated hydrochloric acid at different temperatures. Sb. Tr., Gos. Nauchn.-Issled. Inst. Gidrolizn. i Sul'fitno-Spirt. Prom. (1961), 9 7-19. Abstract only.
Lebedev, et al. Hydrolysis of wood with concentrated hydrochloric acid solutions at different temperatures. Sb. Tr., Gos. Nauchn.-Issled. Inst. Gidrolizn. i Sul'fitno-Spirt. Prom. (1961), 9 20-35. Abstract only.
Lee, et al. Dilute-Acid Hydrolysis of Lignocellulosic Biomass. Advances in Biochemical Engineering/ Biotechnology. 1999; 65:93-115.
Lee, et al. Ionic Liquid-Mediated Selective Extraction of Lignin From Wood Leading to Enhanced Enzymatic Cellulose Hydrolysis. Biotechnology and Bioengineering. Apr. 1, 2009; 102(5):1368-1376.
Lee, et al. Novolak PF resins prepared from phenol liquefied Cryptomeria japonica and used in manufacturing moldings. Bioresource Technology. 2008; 99:7247-7254.
Lee, et al. Solvent Extraction of Zinc from Strong Hydrochloric Acid Solution with Alamine336. Bull. Korean Chem. Soc. 2009; 30(7):1526-1530.
Leonard, et al. Fermentation of wood sugars to ethyl alcohol. US Department of Agriculture, Forest Service, Forest Products Laboratory, Madison, Wisconsin. No. R1466. Dec. 1944.
Lepifre, et al. Enzymatic lignin modification for resin applications. 6th international confrence textile and polymer biotechnology, Ghent, Sep. 2009.
Leschinsky, et al. Detailed Mass Balance of the Autohydrolysis of Eucalyptus Globulus at 170C. BioResources. 2009; 4(2): 687-703.
Leshchuk, et al. Continuous hydrolysis of plant tissue with 45-48% hydrochloric acid. V. Equilibrium in the system polysaccharides-hydrolysis products-hydrochloric acid. Gidrolizn. i Lesokhim. Prom. (1965), 18(5), 10-13. Abstract only.
Leshchuk, et al. Intensification of differential hydrolysis of softwood with concentrated hydrochloric acid in a diffusion apparatus. USSR. Sb. Tr. Vses. Nauch.-Issled. Inst. Gidroliza Rast Mater. (1968), 17 16-73. From: Ref. Zh., Khim. 1969, Abstr. No. 17P20. Abstract only.
Leshchuk, et al. Penetration of concentrated hydrochloric acid into the pores of wood particles and the formation of hydrolyzates within the particles. Sbornik Trudov. Gosudarstvennyi Nauchno-issledovatel'skii Institut Gidroliznoi i Sul'fitno-spirtovoi Promyshlennosti (1966), 15 156-67. CODEN: SGSSAC. Abstract only.
Lewkowski et al. Synthesis, chemistry and applications of 5-hydroxymethylfurfural and its derivatives. Arkivoc; 2001; I; 17-54.
Li, et al. Acidolysis of Wood in Ionic Liquids. Ind. Eng. Chem. Res. 2010; 49(7):3126-3136.
Li, et al. Efficient Acid-Catalyzed Hydrolysis of Cellulose in Ionic Liquid. Advanced Synthesis & Catalysis; 2007; 349; 1847-1850.
Li, et al. Ethanol Organosolv Lignin-based Rigid Polyurethane Foam Reinforced with Cellulose Nanowhiskers. Institute of Paper Science and Technology. 2011.
Li, et al. Interaction of Supercritical Fluids with Lignocellulosic Materials. Ind. Eng. Chem. Res. 1988; 27:1301-1312.
Li, et al. Kraft Lignin-based Rigid Polyurethane Foam. Institute of Paper Science and Technology. 2011.
Li, et al. Lignin depolymerization/repolymerization and its critical role for delignification of aspen wood by steam explosion. Bioresource Technology 98 (2007) 3061-3068.
Li, et al. Steam explosion lignins; their extraction, structure and potential as feedstock for biodiesel and chemicals. Bioresource Technology. 2009.
LigniMatch. Future use of lignin in value added products: A roadmap for possible Nordic/Baltic innovation. The roadmap compiles inputs from the detailed technical reports delivered in the LigniMatch project during 2007-2009. For more information, see the project website at http://www.chalmers.se/gmv/EN/projects/lignimatch.
Liitia, et al. Application of Solid-State $_{13}$C NMR Spectroscopy and Dipolar Dephasing Technique to Determine the Extent of Condensation in Technical Lignins. Solid State Nuclear Magnetic Resonance. 2002; 21:171-186.
Lin, et al. Ethanol fermentation from biomass resources: current state and prospects. Appl Microbiol Biotechnol. 2006; 69:627-642.
Lin et al. Liquid phase reforming of rice straw for furfural production. International Journal of Hydrogen Energy; 2013; 4-10.
Lin, et al. Liquid-Liquid Equilibria for Ternary Mixtures of Water + Ethanol with 1-Hexanol, Butyl Propionate, or Ethyl Caproate. J. Chem. Eng. Data. 2003; 48:587-590.
Liu, et al. Citrus Pectin: Characterization and Inhibitory Effect on Fibroblast Growth Factor-Receptor Interaction. J. Agric. Food Chem. 2001; 49:3051-3057.
Liu et al. Effects of lignin-metal complexation on enzymatic hydrolysis of cellulose. Journal of agricultural and food chemistry. 2010; 58(12): 7233-7238.
Liu, et al. Partial flow of compressed-hot water through corn stover to enhance hemicellulose sugar recovery and enzymatic digestibility of cellulose. Bioresource Technology. 2005; 96:1978-1985.
Liu, et al. Solvation of Extracted Complex Metal Acids. VII. An Improved Model. The Journal of Physical Chemistry. 1974; 78(25):2572-2575.
Liu. Understanding Starches and Their Role in Foods. Chapter 7. Copyright 2005 by Taylor & Francis Group, LLC.
Locke. Chemical Conversion Products from wood. USDA. Aug. 1960.
Loe, et al. Vanillin from wood: A CO2-friendly and sustainable bio-chemical. Lignin-based vanillin draws on the original biorefinery concept. Specialty Chemicals Magazine. May 1, 2011. 30-31.
Long, et al. Application of the Ho Acidity Function to kinetics and Mechenisms of acid Catalysis. Mar. 30, 1957; 935-1010.
Lora., et al. Autohydrolysis sf aspen milled wood lignin. AYMANC. An. J. Chem. 1980; 58:669-676.
Lora, et al. Recent Industrial Applications of Lignin: A Sustainable Alternative to Nonrenewable Materials. Journal of Polymers and the Environment, Apr. 2002; 10(1-2):39-48.
Lora, et al. Use of sulfur-free lignin in wood adhesives: Industrial experiences and environmental impacts. 2005; 8-14.
Lora. GreenValue-Technologies and Products. GreenValueEnterprises LLC, Media, PA, USA. 2011.
Lora. Lignin recovery technology transfer: first industrial implementation of the LPS process in India. 2005.
Lora. Non-Wood Biorefinery Developments Outside North America. 2011.
Lund, et al. Enzymatic modification of kraft ligninthrough oxidative coupling with water-soluble phenols. Appl Microbiol Biotechnol. 2001; 55:6*9-703.
Lynd, et al. Strategic Biorefinery Analysis: Analysis of Biorefineries, Jan. 24, 2002-Jul. 1, 2002. Subcontract Report, NREL/SR-510-35578, Jan. 10, 2005.
Ma, et al. Conversion of fructose to 5-hydroxymethylfurfural with a functionalized ionic liquid. BioResources; 2011; 7; 533-544.
Mabee, et al. Updates on Softwood-to-Ethanol Process Development. Applied Biochemistry and Biotechnology, 2006;129-132:55-70.

(56) References Cited

OTHER PUBLICATIONS

Macala et al. Hydrogen transfer from supercritical methanol over a solid base catalyst: a model for lignin depolymerization. ChemSusChem. 2009; 2: 215-217.
Mackenzie, et al. The solvent extraction of some major metals an overview. 2010.
Mai, et al. Biotechnology in the wood industry. Appl Microbiol Biotechnol; 2004; 63:477-494.
Malherbe, et al. Lignin Chemistry and Selected Applications. ILI—International Lignin Institute, Internal work for Umbrella. Aug. 23, 2007.
Malutan, et al. Contribution to the Study of Hydroxymethylation Reaction of Alki lignin. BioResources. 2008; 3(1):13-20.
Malutan, et al. Contributions to the lignin modification by hydroxymethylation and epoxidation. 2008.
Manninen, et al. Comparing the VOC emissions between air-dried and heat-treated Scots pine wood. Atmospheric Environment. 2002; 36:1763-1768.
Marcano, et al. Surface activity of lignin fractions obtained at different pH values. 2005.
Marchal, et al. Conversion into acetone and butanol of lignocellulosic substrates pretreated by steam explosion. Biotechno!ogy Letters. 1986; 8(5):365-370.
Marchal, et al. Large-Scale Enzymatic Hydrolysis of Agricultural Lignocellulosic Biomass. Part 2: Conversion into Acetone-Butanol. Bioresource Technology. 1992; 42:205-217.
Marcotullio et al. Bioenergy II : Furfural Destruction Kinetics during Sulphuric Acid-Catalyzed Production from Biomass Bioenergy II : Furfural Destruction Kinetics during Sulphuric Acid-Catalyzed Production from Biomass. International journal of Chemical Reactor Engineering; 2009; 7; Article A67.
Marcotullio et al. Furfural production in modern lignocellulose-feedstock biorefineries. Presentation; Delft University of Technology; St. Petersburg; 2013.
Marcotullio. The chemistry and technology of furfural production in modern Lignicellulose-feedstock biorefineries. PhD thesis. 2011; Delft University, Italy.
Marker, et al. Optical properties of glucose. 2009.
Marone, et al. Effect of particle sizes on the kinetics of drying of a hydrochloric acid hydrolysate mass. Gidroliznaya i Lesokhimicheskaya Promyshlennost (1976), (3), 15. CODEN: GLKPA2 ISSN: 0016-9706. Abstract only.
Marsh et al. Possible Uses of Corncob Cellulose in the Explosives Industry. The journal of Industrial and Engineering Chemistry; 1921; 13(4); 296-298.
Martin, et al. Engineering a mevalonate pathway in *Escherichia coli* for production of terpenoids. Nature Biotechnology. 2003; 21(7):796-802.
Martin, et al. Studies on thermal properties of sisal fiber. Thermochemica Acta 2010, 506, 14-19.
Martinez-Inigo, et al. Time course of fungal removal of lipophilic extractives from Eucalyptus globulus wood. Journal of Biotechnology. 2000; 84:119-126.
Martin-Sampedro, et al. Combination of steam explosion and laccase-mediator treatments prior to Eucalyptus globulus kraft pulping. Bioresource Technology 2011; 102:7183-7189.
Mascal, et al. Direct, High Yield Conversion of Cellulose into Biofuel. Angew. Chem. Int. Ed. 2008; 7:7924-7926.
Mascal, et al. High-Yield Chemical Conversion of Biomass into Biofuels and Value added Products. Clean Technology 2010, www.ct-si.org, ISBN 978-1-4398-3419-0. 124-127.
Mascal et al. Towards the efficient, total glycan utilization of biomass. ChemSusChem; 2009; 2(5); 423-426.
Masura. A mathematical model for neutral sulfite pulping of various broadleaved wood species. Wood Science and Technology. 1998; 32:1-13.
Mathias, et al. Production of Vanillin by Oxidation of Pine Kraft Lignins with Oxygen. Holzforschung. 1995; 49:273-278. Abstract only.
Mattinen, et al. Polymerization of different lignins by laccase. BioResources. 2008; 3(2):549-565.
McAloon, et al. Determining the Cost of Producing Ethanol from Corn Starch and Lignocellulosic Feedstocks. National Renewable Energy Laboratory, Contract No. DE-AC36-99-GO10337, NREL/TP-580-28893. Prepared under Task No. BFP1.7110. Oct. 2000.
McFeeters, et al. Measurement of Pectin Methylation in Plant Cell Walls. Analytical biochemistry. 1984; 139:212-2 17.
McKenzie, et al. Levulinic acid. Organic Syntheses, Coll. vol. 1, p. 335 (1941); vol. 9, p. 50 (1929). Apr. 29, 2010.
McMillan. Processes for Pretreating Lignocellulosic Biomass: A Review. NatioRnenaewlable Energy Laboratory, A Division of Midwest Research Institute, Operated for the U.S. Department of Energy , Under Contract No. DE-AC02-83CH 10093. Nov. 1992.
Medical Dictionary: thefreedictionary.com. "Oligosaccharide". Downloaded Mar. 27, 2017. 2 pages.
Meindersma et al. Production of discrete oxygenated target chemicals from pyrolysis oil. A Report by Eindhoven University of Technology. Netherlands. Jun. 2009.
Meister. Product synthesis, polymer characterization and applications testing of lignin graft copolymers. The international Lignin Institute, 5th international Forum' Sep. 7, 2000, Bordeaux (France). Membralox ceramic membrane products. Pall corporation. 2004; 1-12.
Menchikov, et al. An Effective Method for Alcohol Preparation by Hydrolysis of Organohalides in the Presence of Copper and its Salts in Aqueous DMSO. Mendeleev Commun. 1995; 5(6): 223-224.
Mendes, et al. Extraction of hemicelluloses prior to kraft cooking: a step for an integrated biorefinery in the pulp mill. XXI Tecnicelpa Conference and Exhibition/VI CIADICYP 2010. Oct. 12-15, 2010.
Mesfun et al. Integration of hot water extraction in biomass based CHP plants—possibilities for green-chemicals and increased electricity production. Master's Thesis. 2010; Lulea University of Technology.
Meyer. Nanotechnology for fibers characterisation. CTP's Scientific and Technological Unit 'Process Pulp-IntechFibers', Jan. 5, 2009.
Michalka. Optimization of Sugar Consumption in the Fermentation of Temulose for Ethanol Production, 2007.
Mielenz. Ethanol production from biomass: technology and commercialization status. Current Opinion in Microbiology. 2001; 4:324-329.
Mikkola, et al. Hydrolytic decomposition of glycosides in aqueous acids. ARKIVOC 2009 (iii) 39-53.
Miljkovic. Carbohydrates, Synthesis, Mechanisms, and Stereoelectronic Effects. Springer Science+Business Media, LLC 2009.
Miller. Characteristics and Availability of Commercially Important Woods, Chapter 1. Forest Products Laboratory. 1999. Wood handbook—Wood as an engineering material.
Miller. Structure of Wood. Chapter 2. 2009.
Miller. Utilization of wood under Germany's four year plan. Forests Products Division, Bureau of Foreign and Domestic Commerce U.S. Department of Commerce, Washington. 2009; 495-503.
Miller. Vapor-Liquid Equilibria below 0° C. of Hydrogen Chloride Solutions Saturated with Calcium Chloride. J. Chem. Eng. Data. 1990; 35:436-440.
Miller. Vapor-Liquid Equilibria of Water-Hydrogen Chloride Solutions below 0° C. J. Chem. Eng. Data 1983; 28:363-367.
Miller. Vapor-Liquid Equilibria of Water-Hydrogen Chloride-Sodium Chloride-Water Solutions below 0° C. J. Chem. Eng. Data. 1985; 30:296-301.
Minina, et al. Hydrolysis of various types of cellulosic raw materials with highly concentrated hydrochloric acid. I. Effect of time, temperature, and acid ratio on the yield of sugars. USSR. Strukt. Modif. Khlop. Tsellyul. (1966), No. 3 315-24. From: Ref. Zh., Khim. 1969, Abstr. No. 1P31. Abstract only.
Miyazawa, et al. Polysaccharide Hydrolysis Accelerated by Adding Carbon Dioxide under Hydrothermal Conditions. Biotechnol. Prog. 2005; 21:1782-1785.
Moelwyn-Hughes. The kinetics of the hydrolysis of certain glucosides, part 11: trehalose, umethylglucoside and tetramethyl-a-amethyglucoside. Nov. 23, 1928; 81-92.
Mohan et al. Pyrolysis of Wood/Biomass for Bio-oil: A Critical Review. Energy & Fuels 20:848-889 (2006).

(56) References Cited

OTHER PUBLICATIONS

Montane, et al. Activated carbons from lignin: kinetic modeling of the pyrolysis of Kraft lignin activated with phosphoric acid. Chemical Engineering Journal. 2005; 106:1-12.
Mooney, et al. The effect of initial pore volume and lignin content on the enzymatic hydrolysis of softwoods. Bioresource Technology. 1998; 64:113-119.
Moreschi, et al. Hydrolysis of Ginger Bagasse Starch in Subcritical Water and Carbon Dioxide. J. Agric. Food Chem. 2004; 52, 1753-1758.
Morreel, et al. Mass Spectrometry-Based Sequencing of Lignin Oligomers. Plant Physiology. Aug. 2010; 153:1464-1478.
Mosier, et al. Characterization of acid catalytic domains for cellulose hydrolysis and glucose degradation. Biotechnology and bioengineering, Sep. 20, 2002; 79(6):1-9.
Mosier, et al. Characterization of Dicarboxylic Acids for Cellulose Hydrolysis. Biotechnol. Prog. 2001; 17:474-480.
Mulder, et al. Lignin based controlled released coating. 2011.
Mullen, et al. Production of Deoxygenated Biomass Fast Pyrolysis Oils via Product Gas Recycling. Energy & Fuels; 2013; A-H.
Munoz, et al. Bioethanol production from bio-organosolv pulps of Pinus radiata and Acacia dealbata. J Chem Technol Biotechnol. 2007; 82:767-774.
Mussatto, et al. Production, characterization and application of activated carbon from brewer's spent grain lignin. Bioresource Technology. 2010; 101:2450-2457.
Myrvold. A new model for the structure of lignosulphonates. 2005.
Mythili, et al. Synthesis, mechanical, thermal and chemical properties of polyurethanes based on cardanol. Bull. Mater. Sci. Jun. 2004 ;27(3):235-241.
Naae. New lignin chemicals and applications: new uses in petroleum recovery. The international Lignin Institute, 5th international Forum' Sep. 7, 2000, Bordeaux (France).
Nagamatsu, et al. Cascade-type flow of lignocellulosic components through the phase-separation system. J. Adv. Sci. 2001; 13(3):517-520.
Nagy, et al. Catalytic hydrogenolysis of ethanol organosolv lignin. Holzforschung. 2009; 63:513-520.
Nagy, et al. Characterization of CO2 precipitated Kraft lignin to promote its utilization. Green Chem. 2010; 12:31-34.
Nassar, et al. Mechanism of thermal decomposition of lignin. Wood and fiber Science. 1984; 16(3):441-453.
Neureiter et al. Dilute-acid hydrolysis of sugarcane bagasse at varying conditions. Applied Biochemistry and Biotechnology. Mar. 2002, vol. 98, Issue 1-9, pp. 49-58.
Nevell. The hydrolysis of cotton cellulose by hydrochloric acid in benzene. Dep. Polym. Fibre Sci., Univ. Manchester Inst. Sci. Technol., Manchester, UK. Carbohydrate Research (1976), 49 163-74. CODEN: CRBRAT ISSN: 0008-6215. Abstract only.
Nguyen, et al. Is gel permeation chromatography applicable to lignin? 2007.
Nguyen, et al. Molecular weight and functional group analysis of a Soda lignin fractionated by ultrafiltration and selective dissolution. 2008.
Nguyen, et al. Molecular weight in LignoAnalyse 1, "Is GPC applicable to lignin?". Rome, Forum 8, May 10-12, 2007.
Nguyen. GPC-2D FTIR : a novel technique for fractionated lignin characterization. SERMACS 2009.
Nikam et al. Density and Viscosity Studies of Glucose and Fructose Solutions in Aqueous and in NH4CL. Journal of Molecular Liquids; 2000; 87; 97-105.
Nitz. Lignin based polymer compounds and liquid wood. The international Lignin Institute, 5th international Forum' Sep. 7, 2000, Bordeaux (France).
Nogueira, et al. Crude tall-oil sodium salts micellization in aqueous solutions studied by static and dynamic light scattering. Colloids and Surfaces A: Physicochemical and Engineering Aspects. 2001; 191: 263-268.
Norgren. Self-Aggregation of Kraft Lignin in Aqueous Solutions. 2005; 23-30 .
Norman, et al. LXXIV. Studies on pectin. V. The hydrolysis of pectin. May 1, 1930; 649-660.
Notice of allowance dated Apr. 8, 2016 for U.S. Appl. No. 13/378,657.
Novozymes application sheet. Cellic® CTec2 and HTec2-Enzymes for hydrolysis of lignocellulosic materials, Fuel Ethanol. 2010.
Novozymes application sheet. CellicTM CTec and Htec, Advanced enzymes for hydrolysis of lignocellulosic materials. Novozymes A/S No. 2009-05048-01. 2009.
Novozymes. The key to the first commercially viable enzymes for cellulosic ethanol. 2010. www.bioenergy.novozymes.com.
NREL. Enzyme Sugar-Ethanol Platform Project. National Renewable Energy Laboratory , Operated for the U.S. Department of Energy by Midwest Research Institute • Battelle • Bechtel. 2010.
nutrients review.com. "Oligosaccharides". Downloaded Mar. 27, 2017. 4 pages.
NWBC. Program, 3rd Nordic Wood Biorefinery Conference (NWBC 2011), Stockholm, Sweden, Mar. 22-24, 2011.
NWBC-2009 The 2 nd Nordic Wood Biorefinery Conference. All Presentations; 2009.
Nyanhongo, et al. A new robust antioxidant activity measuring method based on laccase oxidation of syringaldazine. Graz University of Technology. 2009.
Nystrand. Feasibility of lignocellulose as feedstock for biological production of super absorbent polymers. Department of Physics, Chemistry and Biology Master's Thesis; Linköping University Department of Physics, Chemistry and Biology 581 83 Linköping. Oct. 2010.
Odincovs, et al. The influence of temperature on the hydrolysis of wood and cellulose with concentrated hydrochloric acid. Trudy Inst. Lesokhoz. Problem, Akad. Nauk Latv. S.S.R. (1951), No. 2 68-82. Abstract only.
Odintsov, et al. Hydrolysis of woods with concentrated acids. Lesokhimicheskaya Promyshlennost (1940), 3(No. 9), 14-19. Abstract only.
Office action dated Feb. 13, 2014 for U.S. Appl. No. 13/378,657.
Office action dated May 10, 2016 for U.S. Appl. No. 14/009,858.
Office action dated May 10, 2016 for U.S. Appl. No. 14/033,205.
Office action dated May 23, 2016 for U.S. Appl. No. 14/537,530.
Office action dated Jun. 8, 2015 for U.S. Appl. No. 13/378,657.
Office action dated Jul. 31, 2014 for U.S. Appl. No. 13/378,657.
Office action dated Aug. 7, 2014 for U.S. Appl. No. 13/378,657.
Office action dated Aug. 24, 2013 for U.S. Appl. No. 13/380,504.
Office action dated Nov. 9, 2015 for U.S. Appl. No. 13/378,657.
Office action dated Dec. 24, 2014 for U.S. Appl. No. 13/378,657.
Oh, et al. Pretreatment of Lignocellulosic Biomass using Combination of Ammonia Recycled Percolation and Dilute-Acid Process. J. Int. Eng. Chem. 2002; 8(1):64-70.
Oliet, et al. Solvent effects in autocatalyzed alcohol-water pulping comparative study between ethanol and methanol as delignifying agents. Chemical Engineering Journal. 2002; 87:157-162.
Olsson, et al. Fermentation of lignocellulosic hydrolysates for ethanol production. Enzyme and Microbial Technology. 1996; 18:312-331.
On, et al. Studies on pulp and paper mill fiber residues as resources. (II). Studies on acid hydrolysis of sludge. Coll. Eng., Jeonbuk Univ., Jenzu, S. Korea. Polpu, Chongi Gisul (1985), 17(1), 38-44. CODEN: PCGIDY ISSN: 0253-3200. Abstract only.
Onda et al. Selective Hydrolysis of Cellulose and Polysaccharides into Sugars by Catalytic Hydrothermal Method Using Sulfonated Activated-carbon. Journal of Japan Petroleum Institue.2012; 55(2): 73-86.
Ong. Conversion of lignocellulosic biomass to fuel ethanol—a brief review. The planter kuala lumpur. 2004; 80(941):517-524.
Ornl. Manufacturing of Carbon Fibers Using Microwave Assisted Plasma Technology. Managed and operated by UT-Battelle, LLC for the U.S. Department of Energy under contract DE-AC05-00OR22725. 2005.
Oudia, et al. Analytical pyrolysis study of biodelignification of cloned Eucalyptus globulus (EG) clone and Pinus pinaster Aiton kraft pulp and residual lignins. J. Anal. Appl. Pyrolysis. 2009; 85:19-29.
Ouensanga, et al. Thermal degradation of sugar cane bagasse. Thermochimica acta 1988, 125, 89-97.

(56) References Cited

OTHER PUBLICATIONS

Ouyang, et al. Chemical modification of lignin assisted by microwave irradiation. Holzforschung, vol. 65, 2011, DOI 10.1515/HF.2011.067.
Oxford Dictionary. "Oligosaccharide". Downloaded Mar. 27, 2017. 1 page.
Palmqvist, et al. Fermentation of lignocellulosic hydrolysates. II: inhibitors and mechanisms of inhibition. Bioresource Technology. 2000; 74:25-33.
Pan, et al. Bioconversion of Hybrid Poplar to Ethanol and Co-Products Using an Organosolv Fractionation Process : Optimization of Process Yields. Biotechnology and bioengineering. 2006; 94: 851-861.
Pan, et al. Biorefining of Softwoods Using Ethanol Organosolv Pulping: Preliminary Evaluation of Process Streams for Manufacture of Fuel-Grade Ethanol and Co-Products. Biotechnology and bioengineering. May 20, 2005; 90(4).
Pandey, et al. Lignin depolymerization and conversion: a review of thermochemical methods. Chemical Engineering and Technology. 2011; 34(1):29-41.
Papadopoulos, et al. The behavior of lignin during hydrolysis of sweetgum wood with concentrated hydrochloric acid at moderate temperatures. Dep. Wood Paper Sci., North Carolina State Univ., Raleigh, NC, USA. Holzforschung (1981), 35(6), 283-6. CODEN: HOLZAZ ISSN: 0018-3830. Abstract only.
Papadopoulou, et al. The Challenge of Bio-Adhesives for the Wood Composite Industries. 2008.
Papadopoulou et al. The Challenge of Bio-Adhesives for the Wood Composite Industries. Report; Theassaloniki, Greece. 2012.
Papadopoulous, et al. Behavior of sweetgum wood xylan and lignin during hydrolysis with concentrated hydrochloric acid at moderate temperatures. Dep. Wood Pap. Sci., North Carolina State Univ., Raleigh, NC, USA. Journal of Applied Polymer Science: Applied Polymer Symposium (1983), 37(Proc. Cellul. Conf., 9th, 1982, Part 2), 631-40. CODEN: JPSSDD ISSN: 0271-9460. Abstract only.
Papajannopoulous, et al. GC-MS analysis of oleoresin of three Greek pine species. Holz als Roh- und Werkstoff. 2001; 59:443-446.
Parisi. Advances in Lignocellulosics Hydrolysis and in the Utilization of the Hydrolyzates. Advances in Biochemical Engmeering/Biotechnology. 1989; 38:53-87.
Parpot et al. Electrochemical investigations of the oxidation-reduction of furfural in aqueous medium. Electrochimica Acta; 2004; 49; 397-403.
Pasco, et al. High Temperature Alkali Treatment of Kraft Black Liquor. This poster was presented at the 15th International Symposium on Wood, Fibre and Pulping Chemistry in Oslo on Jun. 15-18, 2009.
Pasquini, et al. Extraction of lignin from sugar cane bagasse and Pinus taeda wood chips using ethanol-water mixtures and carbon dioxide at high pressures. J. of Supercritical Fluids. 2005; 36:31-39.
Pasquini, et al. Sugar cane bagasse pulping using supercritical CO2 associated with co-solvent 1-butanol/water. J. of Supercritical Fluids. 2005; 34:125-131.
Paszner, et al. High-yield Organosolv process for conversion of cellulosic biomass to ethanol. Fac. For., Dep. Harvest. Wood Sci., Vancouver, BC, Can. Energy from Biomass and Wastes (1989), 12 1297-318. CODEN: EBWADU ISSN: 0277-7851. Abstract only.
Patel, et al. Medium and long-term Opportunities and Risks of the Biotechnological Production of Bulk Chemicals from Renewable Resources—The Potential of White Biotechnology the BREW project. Utrecht University. Sep 2006. www.chem.uu.nl/nws.
Paul, et al. Optical absorption and fluorescence studies on imidazolium ionic liquids comprising the bis (trifluoromethanesulphonyl)imide anion. J. Chem. Sci.; 2006; 118(4); 335-340.
Pazur. Reversibility of enzymatic transglucosylation reactions. Received for publication, Jan. 17, 1955, pp. 531- 538.
Pearl. Vanillin from Lignin Material. J. Am. Chem. Soc., 1942; 64(6):1429-1431.

Pecina, et al. GC-MS and HPLC analyses of lignin degradation products in biomass hydrolyzates. Fresenius Z Anal Chem. 1986; 325:461-465.
Pending Claims dated Jun. 7, 2016 for U.S. Appl. No. 14/009,858.
Pending Claims dated Jun. 7, 2016 for U.S. Appl. No. 14/033,205.
Pepper, et al. Improvements in the acidolysis procedure for lignin isolation and in the procedure for the analysis of lignin oxidation products. Can J. Chem. 1961; 39:390-391.
Pepper, et al. The effect of initial acid concentration on the lignin isolated by the acidolysis of aspen wood. Can J. Chem. 1961; 39:1454-1461.
Pepper, et al. The Isolation of a Representative Lignin Fraction From Wood and Straw Meals. Canadian J. of Chemistry. 1962; 40:1026-1028.
Perez, et al. Study of the behavior of metal adsorption in acid solutions on lignin using a comparison of different adsorption isotherms. Lat. Am. appl. res. v.37 n. 2 Bahia Blanca abr. 2007.
Perlack, et al. Biomass as feedstock for a bioenergy and bioproducts industry: the technical feasibility of a billion-ton annual supply. U.S. Department of Energy, under contract DE-AC05-00OR22725. Apr. 2005.
Perng et al. Pilot Treatment of OCC-based Paper Mill Wastewater Using Pulsed Electrocoagulation. Water Qual. Res. J. Canada; 2007; 42(1); 63-71.
Perng et al. Treatment of a Specialty Paper Mill Wastewater Using a Pilot-scale Pulsed Electrocoagulation Unit. Taiwan J for Sci; 2007; 22(3); 355-366.
Perry, et al. Chemical Engineers' Handbook. The McGraw-Hill Companies. 1999.
Pessoa Jr, et al. Acid hydrolysis of hemicellulose from sugarcane bagasse. Braz. J. Chem. Eng. vol. 14 No. 3 São Paulo Sep. 1997.
Peterson, et al. Thermochemical biofuel production in hydrothermal media: A review of sub and supercritical water technologies. Energy & Enviromental Science. 2008; 1:32-65.
Petkevich, et al. Hydrolysis of wood with concentrated hydrochloric acid in a pilot battery of diffusers. Sb. Tr., Gos. Nauchn.-Issled. Inst. Gidrolizn. i Sul'fitno-Spirt. Prom. (1960), 8 47-65. Abstract only.
Pettersen. The Chemical Composition of Wood. In: Rowell M., ed. The chemistry of solid wood. Advances in chemistry series 207. Washington, DC: American Chemical Society ; 1984: Chapter 2.
Philip, et al. Review Polyhydroxyalkanoates: biodegradable polymers with a range of applications. J Chem Technol Biotechnol. 2007; 82:233-247.
Phillips, et al. Thermochemical Ethanol via Indirect Gasification and Mixed Alcohol Synthesis of Lignocellulosic Biomass. National Renewable Energy Laboratory, Technical Report NREL/TP-510-41168. Apr. 2007.
Phillips. Technoeconomic Analysis of a Lignocellulosic Biomass Indirect Gasification Process to Make Ethanol. Ind. Eng. Chem. Res. 2007; 46:8887-8897.
Pielhop, et al. Two-step approach for the conversion of kraft lignin into aromatic chemicals. NWBC 2011, Stockholm, Mar. 21-24, 2011.
Pierce. Instruction Acylation Derivatization Reagents. Pierce, Rockford, IL 61105, US. 2010.
Ping, et al. Evaluation of grape stalks as bioresource. Industrial crops and products. 2011; 33:200-204.
Pisarnitsky, et al. Effect of Acid Hydrolysis of Oak Wood on Its Aroma-Forming Complex. Applied Biochemistry and Microbiology. 2004; 40(6):613-616.
Pogaku, et al. Whey Protein Isolate-Starch System—A Critical Review. International Journal of Food Engineering: vol. 3 : Iss. 6, Article 1. 2007.
Poltoratskii, et al. Liquid-Vapor Equilibrium and Ionization of HCl in the System HCl-H2SO4-H2O at 298 K. Russian Journal of General Chemistry. 2002; 72(9):1339-1342.
Polymer Science. Making Polyurethane. Polymer Science Learning Center, Department of Polymer Science the University of Southern Mississippi. 2005.
Pontin. First, Cure Malaria. Next Global Warming. The New York times/SundayBusiness/Bright Ideas. Jun. 3, 2007.
Popa, et al. A comparison concerning separation and characterization of polyphenols from spruce wood bank. 2010.

(56) References Cited

OTHER PUBLICATIONS

Popa, et al. Composites based on natural resources: lignocelluloses, lignins and furan resins. 2008.
Popa, et al. On the interaction of lignins, furan resins and furfuryl alcohol in adhesive systems. Cellulose Chem. Technol. 2007; 41(2-3):119-123.
Pospiech, et al. Studies on iron(III) removal from chloride aqueous solutions by solvent extraction and transport through polymer inclusion membranes with D2EHPA. Physicochem. Probl. Miner. Process. 2010; 44:195-204.
Prater, et al. Determination of Sulfur Dioxide in Dehydrated Foods. Industrial and engineering chemistry. Mar. 1944; 16(3):153-157.
Priefert, et al. Biotechnological production of vanillin. Appl Microbiol Biotechnol. 2001; 56:296-314. Abstract only.
Pu, et al. Ionic Liquid as a Green Solvent for Lignin. Journal of Wood Chemistry and Technology. 2007; 27:23-33.
Pu, et al. NMR Characterization of C3H and HCT Down-Regulated Alfalfa Lignin. Bioenerg. Res. 2009; 2:198-208.
Pulping and Bleaching, PSE 476 powerpoint. 2011.
Purolite. Corn sweetener refining with ion exchange resins guide. The Purolite Compant. 2007. 60 pages. www.purolite.com.
Pye. The Alcell Process—A Proven Alternative to Kraft Pulping. 1990 Pulping Conference, TAPPI Proceedings. 991-996.
Qian, et al. Acidic Sugar Degradation Pathways an Ab Initio Molecular Dynamics Study. Applied Biochemistry and Biotechnology. 2005;121-124:989-997.
Quinde. Enzymes in the pulp and paper industry: a review. 1994.
Qvintus-Leino. Utilisation of lignin in fiber board gluing. VTT Processes, Finland. 2003.
Rabinovich. Wood hydrolysis industry in the Soviet Union and Russia: a mini-review. Cellulose Chem. Technol.2010; 44(4-6):173-186.
Radiotis, et al. Optimizing Production of Xylose and Xylooligomers from Wood Chips. 3rd NWBC, Stockholm, Sweden Mar. 23, 2011.
Ragan, et al. LignActiv—Activated Carbon from Renewable Resources—Lignin. Nordic Wood Biorefinery Conference. Stockholm, Mar. 24, 2011.
Ragauskas, et al. From wood to fuels Integrating biofuels and pulp production. Industrial biotechnology. 2006; 2(1):55-65.
Ragauskas, et al. The Path Forward for Biofuels and Biomaterials. Science. Jan. 26, 2006; 311:484-489.
Ragauskas. Forest BioRefinery Lignin. School of Chemistry and Biochemistry, Georgia Institute of Technology. 2010.
Ragauskas. Rediscovering the Future of Lignin Chemistry. 2003.
Ramiah, et al. TGA and DTA of Cellulose, Hemicellulose, Lignin. J. Appl. Poly. Sci. 1970, 14, 1323-1337.
Raz. Literature review on concentrated HCl hydrolysis of lignocellulosic material. Aug. 2008.
Raz. Weyland bioethanol report. 2010.
Readnour, et al. Thermodynamic Properties for the Dissociation of Bisulfate Ion and the Partial Molal Heat Capacities of Bisulfuric Acid and Sodium Bisulfate over an Extended Temperature Range. Inorganic Chemistry. Oct. 1969; 8(10):2174-2182.
Reese. A microbiological process report; enzymatic hydrolysis of cellulose. Appl Microbiol. Jan. 1956;4(1):39-45.
Reinhold. SEC of lignins. Mainz, Germany. 2007.
Reith. Development of integrated lignocellulose biorefinery for co-production of chemicals, transportation fuels, electricity and heat. EU FP6 Integrated Project Biosynergy. 2009.
RIGA/Latvia. Wood-based adhesives: environmental aspects. 5th EU Programme project WOODPRO Integration of Latvian State Institute of Wood Chemistry in European Research Area. Workshop, Jul. 20-21, 2005.
Ritcey et al. Development of Industrial Solvent Extraction Processes. (Report) Gordon M. Ritcey & Associates, Inc; Nepean, Ontario, Canada.2004.
Robbins, et al. Liquid-Liquid Extraction Operations and Equipment. Sec. 15. 2009.
Robertson. Factors Governing the Nitration of Cellulose. PhD Thesis; Cornell University. 1946.
Robertson. The fractional extraction and quantitative determination of pectic substances in grapes and musts. Am. J. Enol. Vitic. 1979; 30(3):182-186.
Rockwood, et al. Energy Product Options for Eucalyptus Species Grown as Short Rotation Woody Crops. Int. J. Mol. Sci. 2008; 9:1361-1378; DOI: 10.3390/ijms9081361.
Rogers, et al. The Advanced Materials Webinar Series: Carbon Fibers. Southern Advanced Materials in Transportation Alliance (SAMTA). 2011.
Roman-Leshkov et al. Production of dimethylfuran for liquid fuels from biomass-derived carbohydrates. Nature; 2007; 447; 982-985.
Rondinini, et al. Reference value standards and primary standards for pH measurements in Organic Solvents and Water + Organic Solvent Mixtures of Moderate to High Permittivities. Pure & Appl. Chem. 1987; 59(11):1549-1560.
Rout et al. Supercritical $CO_2$ Fractionation of Bio-oil Produced from Mixed Biomass of Wheat and Wood Sawdust. Energy & Fuels; 2009; 13; 6181-6188.
Rovio, et al. Determination of monosaccharide composition in plant fiber materials by capillary zone electrophoresis. Journal of Chromatography A. 2008; 1185:139-144.
Rovio, et al. Determination of neutral carbohydrates by CZE with direct UV detection. Electrophoresis. 2007; 28:3129-3135.
Rozmarin, et al. Fermentative evaluation of prehydrolyzates from chemical cellulose manufacturing. II. Study on some factors affecting the inversion process. Rom. Revista Padurilor-Industria Lemnului-Celuloza si Hirtie: Celuloza si Hirtie (1977), 26(4), 158-62. CODEN: RPLHDX ISSN: 0258-2287. Abstract only.
Rugg. Optimization of the NYU continuous cellulose hydrolysis process. B01447 Biofuels Information Center. Dec. 1982.
Ruiz-Angel et al. Reversed-phase liquid chromatography analysis of alkyl-imidazolium ionic liquids II. Effects of different added salts and stationary phase influence. Journal of chromatography A; 2008, 1189; 476-482.
Ruiz-Rosa, et al. The production of submicron diameter carbon fibers by the electrospinning of lignin. Carbon. 2010; 48:696-705.
Rumbold. Selection of production hosts for real-life feedstock utilization. TNO Kwaliteit van Leven, Oct. 20, 2007.
Rutten, et al. Measurements of the heats of dilution and description of the system $H_2O/H_2SO_4$/HCl with a solvation model. Fluid Phase Equilibria. 1998; 153:317-340.
Saadatmand, et al. Prehydrolysis in softwood pulping produces a valuable biorefinery fraction for material utilization. Environ. Sci. Technol. Jul. 7, 2012; DOI: 10.1021/es301699n.
Saari et al. Adsorption Equilibria of Arabinose, Fructose, Galactose, Rhamnose, Sucrose, and Xylose on Ion-Exchange Resins. J. Chem. Eng.; 2010; 55; 3462-3467.
Saariaho. Resonance raman spextroscopy in the analysis of residual lignin and other unsaturated structures in chemical pulps. Helsinki University of Technology (Espoo, Finland) on Jan. 14, 2005.
Saddler et. al. Pretreatment of Lodgepole Pine Killed by Mountain Pine Beetle Using the Ethanol Organosolv Process: Fractionation and Process Optimization. Ind. Eng. Chem. Res. 2007;46: 2609-2617.
Saeman. Kinetics of the hydrolysis of wood and of the decomposition of sugars in dilute acid at high tempratures. USDA. Sep. 1944.
Saha, et al. Dilute Acid Pretreatment, Enzymatic Saccharification, and Fermentation of Rice Hulls to Ethanol. Biotechnol. Prog. 2005; 21:816-822.
Sakai et al. Effect of lignocellulose-derived inhibitors on growth of and ethanol production by growth-arrested Corynebacterium glutamicum R. Applied and environmental microbiology; 2007; 73(7); 2349-2353.
Saltberg et al. Removal of metal ions from wood chips during acidic leaching 1: Comparison between Scandinavian softwood, birch and eucalyptus. Nordic Pulp and Paper Research Journal. 2006; 21: 507-512.
Saltberg, et al. Removal of metal ions from wood chips during acidic leaching 2: Modeling leaching of calcium ions from softwood chips. Nordic Pulp and Paper Research J. 2006; 21(4):513-519.
Samuel, et al. Structural Characterization and Comparison of Switchgrass Ball-milled Lignin Before and after Dilute Acid Pretreatment. Appli. Micr. BioTech. 2010, 162:62-74.

(56) References Cited

OTHER PUBLICATIONS

Sanchez, et al. Structural analysis of acid catalysed furfuraldehyde resins by thermal degradation techniques. Eur. Polym. J. 1994; 30(1):43-50.
Sanchez, et al. Trends in biotechnological production of fuel ethanol from different feedstocks. Bioresource Technology. 2008; 99:5270-5295.
Sanders, et al. Shuttle hydrochloric acid process for the preparation of oligosaccharides containing products from wood. Comm. Eur. Communities, [Rep.] EUR (1987), (EUR 11084, Degrad. Lignocellul. Ruminants Ind. Processes), 97-101. CODEN: CECED9 ISSN: 0303-755X. Abstract only.
Sannigrahi, et al. Cellulosic biorefineries—unleashing lignin opportunities. Current Opinion in Environmental Sustainability. 2010; 2:383-393.
Sannigrahi, et al. Effects of two-stage dilute acid pretreatment on the structure and composition of lignin and cellulose in loblolly pine. Bioenerg. Res 2008; 1 (3-4): 205-214.
Sannigrahi, et al. Pseudo-lignin and pretreatment chemistry. Energy Environ. Sci. 2011; 4:1306-1310.
Saquin, et al. Lignin Oxidative Chemistry Using Supercritical / Expanded Media. 2005.
Sarkanen, et al. The development of plasticizers for alkylated kraft ligninbased polymeric materials. 2005.
Sasaki, et al. Cellulose hydrolysis in subcritical and supercritical water. J. of Supercritical Fluids. 1998; 13:261-268.
Sassner, et al. Techno-economic evaluation of bioethanol production from three different lignocellulosic materials. Biomass and bioenergy. 2008; 32:422-430.
Satin Sweet@ 65% High Maltose Corn Syrup. Cargill foods. www.cargillfoods.com Updated Aug. 12, 2014.
Sato, et al. Determination of monosaccharides derivatized with 2-aminobenzoic Acid by capillary electrophoresis. Ana. BioChem. 1997; 251: 119-121.
Scaringelli, et al. Pre-hydrolysis of sweetgum wood—an integrated approach to the conversion of lignocellulose from wood into useful chemicals. Report (1979), (NSF/RA-790218; Order No. PB80-108640), 38 pp. From: Gov. Rep. Announce. Index (U. S.) 1980, 80(5), 810. Abstract only.
Schaefer. Bio-Based opportunities in chemicals & energy. Novozymes. London, UBS. Nov 17, 2010.
Schaeffer. ASTM activated carbon standards. 2002.
Schlamadinger, et al. Effects of the Kyoto protocol on forestry and bioenergy products for mitigation of net carbon emissions. IEA Bioenergy, proceedings of the workshop. Apr. 1998. 202 pages.
Schlea, et al. Extraction of Iron, Cobalt, and Nickel Sulfates by Organic liquids. Industrial and engineering chemistry. Jun. 1957; 49(6):1056-1057.
Schoenemann. The New Rheinau Wood Saccharification Process. Institute of Chemical Technology. Jul. 27, 1953; 1-49.
Schuchardt et al. Hydrolysis of sugar cane bagasse with hydrochloric acid, promoted by metallic cations. Journal of Chemical Technology & Biotechnology. 1986; 36:329-334.
Schultz, et al. Proposed Mechanism for the Nitrobenzene Oxidation of Lignin. Holzforschung—International Journal of the Biology, Chemistry, Physics and Technology of W. 1986; 40(2):93-97.
Schutz. The hydrolysis of wood with hydrochloric acid or chlorides as catalysts in acetic acid solution. Zellwolle, Kunstseide, Seide (1942), 47:8-9. Abstract only.
Scifinder. Steam pretreatment of wood in relation to enzymatic hydrolysis. Final report. Energy Res. Abstr. 1989, 14(17), Abstr. No. 35904.
Scurfield, et al. Amino-Acid Composition of Wood Proteins. J. Experimental Botany. 1970; 21(6):857-68.
Segatin, et al. Thermodynamics of the Solubility of Water in 1-Hexanol, 1-Octanol, 1-Decanol, and Cyclohexanol. Monatshefte fur Chemie. 2004; 135:241-248.
Sen, et al. A Review of Cellulose Non-Derivatizing Solvent Interactions with Emphasis on Activity in Inorganic Molten Salt Hydrates. Sustainable Chemistry & Engineering. 2013:858-870.
Sena-Martins, et al. Enzyme modified lignins for environment—friendly products. 2005.
Sendich, et al. Recent process improvements for the ammonia fiber expansion (AFEX) process and resulting reductions in minimum ethanol selling price. Bio. Tech. 2008; 99:8429-8435.
Sevcik, et al. Rapid analysis of carbohydrates in aqueous extracts and hydrolysates of biomass using a carbonate-modified anion-exchange column. J Chromatogr A. Mar. 4, 2011;1218(9):1236-43. doi: 10.1016/j.chroma.2011.01.002. Epub Jan. 11, 2011.
Sharkov, et al. Conversion of difficult-to-hydrolyze wood polysaccharides to an easy-to-hydrolyze condition with hydrogen chloride under pressure. USSR. Sb. Tr., Vses. Nauch.-Issled. Inst. Gidroliza Rast. Mater. (1971), No. 21 65-74, 205. Abstract only.
Sharkov. Production of Polyhydric Alcohols from Wood Polysaccharides. Angew. Chem. internat. Edit. 1963; 2(8):405-492.
Shatalov, et al. Kinetics of organosolv delignification of fibre crop *Arundo donax* L. Industrial Crops and Products. 2005; 21:203-210.
Sheehan, et al. Energy and Environmental Aspects of Using Corn Stover for Fuel Ethanol. Journal of Industrial Ecology. 2004; 7(3-4):117-146.
Shen, et al. Lignin-Based Activated Carbon Fibers and Controllable Pore Size and Properties. Journal of Applied Polymer Science. 2011; 121:989-994.
Shen, et al. Product overview and market projection of emerging bio-based plastics, Utrecht University. PRO-BIP 2009.
Sherrard, et al. Review of wood saccharification processes in the United States Prior to World War II. Industrial and Engineering Chemistry. 1945. 37(1):1-10.
Shimizu, et al. Integrated process for total utilization of wood components by steam-explosion pretreatment. Biomass and bioenergy. 1998; 14(3):195-203.
Shorr, et al. Phase equilibria and the telomerization reaction. I & EC Fundamentals. 1963; 39(1):86-87.
Shulga. Advanced application of lignin-based adhesives. 2005; 42-47.
Shulga, et al. Effect of rheological properties of the lignin-based adhesive on aggregating of light-textured soil. 2008.
Sidiras, et al. Simulation of acid-catalysed organosolv fractionation of wheat straw. Bioresource Technology. 2004; 94:91-98.
Sigma. Enzymatic Assay of α-Glucosidase. Sigma quality control test procedure. Sigma Product information, Revised: Aug. 9, 1996.
Sigma. Enzymes and Reagents for Alternative Energy. Sigma-Aldrich. Biofiles. 2010; 5(5).
Simonell, et al. Lignin Pyrolysis Products, Lignans, and Resin Acids as Specific Tracers of Plant Classes in Emissions from Biomass Combustion. Environ. Sci. Technol. 1993; 27:2533-2541.
Singh, et al. Visualization of Biomass Solubilization and Cellulose Regeneration During Ionic Liquid Pretreatment of Switchgrass. Biotechnology and Bioengineering. Sep. 1, 2009; 104(1):68-75.
Sluiter, et al. Compositional analysis of lignocellulosic feedstocks. 1. Review and description of methods. Journal of agricultural and food chemistry. 2010; 58:9043-9053.
Sluiter, et al. Determination of Ash in Biomass, Laboratory Analytical Procedure (LAP), Issue Date: Jul. 17, 2005. Technical Report, NREL/TP-510-42622, Jan. 1, 2008.
Sluiter, et al. Determination of Sugars, Byproducts, and Degradation Products in Liquid Fraction Process Samples. Laboratory Analytical Procedure (LAP), Contract No. DE-AC36-99-GO10337. Issue Date: Dec. 8, 2006.
Sluiter, et al. Determination of Sugars, Byproducts, and Degradation Products in Liquid Fraction Process Samples, Laboratory Analytical Procedure (LAP), Issue Date: Dec. 8, 2006. Technical Report, NREL/TP-510-42623, Jan. 1, 2008.
Sluiter, et al. Determination of Total Solids in Biomass and Total Dissolved Solids in Liquid Process Samples, Laboratory Analytical Procedure (LAP), Issue Date: Mar. 31, 2008. Technical Report, NREL/TP-510-42621, Revised Mar. 2008.
So, et al. Economic Analysis of Selected Lignocellulose-to-Ethanol Conversion Technologies. Applied Biochemistry and Biotechnology. 1999; 77-79:633-640.
Soloman, et al. Grain and cellulosic ethanol: History, economics, and energy policy. Biomass and Bioenergy. 2007; 31:416-425.

(56) References Cited

OTHER PUBLICATIONS

Spaccini, et al. Molecular characteristics of humic acids extracted from compost at increasing maturity stages. Soil Biology & Biochemistry. 2009 41:1164-1172.
Srinorakutara, et al. Approach of Cassava Waste Pretreatments for Fuel Ethanol Production in Thailand. 2010.
Srinorakutara, et al. Utilization of Waste from Cassava Starch Plant for Ethanol Production. The Joint International Conference on "Sustainable Energy and Environment (SEE)" Dec. 1-3, 2004, Hua Hin, Thailand. 344-349.
Srndovic. Ultrastructure of the primary cell wall of softwound fibres studied using dynamic FT_IR spectroscopy. Licentiate Thesis, Royal Institute of Technology. Stockholm 2008.
Starr, et al. Water-enhanced solubility of carboxylic acids in organic solvents and its applications to extraction processes. Lawrence Berkeley Laboratory, University of California, Nov. 1991.
Steele. Recent breakthroughs in enzymes for biomass hydrolysis. Genecor. National Ethanol Conference, Feb. 23-25, 2009, San Antonio, Texas.
Steinbuchel. Polymeric and low molecular weight hydrophobic chemicals produced by microorganisms from renewables. Renewable Resources & Biorefineries Conference, Sep. 6-8, 2006, York, UK.
Stepnowski et al. Analysis of Environmental Fate and Quantitative Methods for Determination of Ionic Liquids. Conference report; International Conference on Enviromental Science and Technology. 2007; KOS, Greece.
Stewart. Lignin as a base material for materials applications: Chemistry, application and economics. Industrial crops and products. 2008; 207:202-207.
Stranges. Friedrich Bergius and the Rise of the German Synthetic Fuel Industry. Isis. Dec. 1984; 75(4):43-667.
Stranges. Synthetic fuel production in prewar and world war II Japan: A case study in technological failure. Annals of Science. 1993; 50:229-265.
Structure of Wood. US Department of Agriculture, Forest Service, Forest Products Laboratory , Research Note FPL-04. Mar. 1980.
Sudo, et al. A New Carbon Fiber from Lignin. Journal of Applied Polymer Science. 1992; 44:127-134.
Sudo, et al. A New Modification Method of Exploded Lignin for the Preparation of a Carbon Fiber Precursor. Journal of Applied Polymer Science. 1993; 48:1485-1491.
Suess. Interaction of organic compounds with calcium carbonate-I. Association phenomena and geochemical implications. Geochimia et Cosmochimic Acata. 1970; 34:157-168.
Sun, et al. Hydrolysis of lignocellulosic materials for ethanol production: a review. Bioresource Technology. 2002; 83:1-11.
Svensson. Minimizing the sulfur content in Kraft lignin. Degree Project, ECTS 30.0,At STFI-Packforsk, Stockholm, 2008.
Taherzadeh, et al. Acid-Based hydrolysis Processes for Ethanol from Lignocellulosic materials: A Review. Bioethaol review, BioResources. 2007; 2(3):472-499.
Taherzadeh, et al. Pretreatment of Lignocellulosic Wastes to Improve Ethanol and Biogas Production: A Review. Int. J. Mol. Sci. 2008; 9:1621-1651; DOI: 10.3390/ijms9091621.
Takagaki et al. Catalytic Transformations of Biomass-Derived Materials into Value-Added Chemicals. Catalysis Surveys from Asia. 2012; 16: 164-182.
Tanaka, et al. Effect of Pore Size in Substrate and Diffusion of Enzyme on Hydrolysis of Cellulosic Materials with Cellulases. Biotechnology and Bioengineering. 1998; 32:698-706.
Tanase, et al. Mass Balance of Extractives Around Impressafiner in Mill and Pilot Scale. 2009. 1-6.
Tang, et al. Effect of Inorganic Salts on Pyrolysis of Wood, Cellulose, and Lignin Determined by Differential Thermal Analysis. U.S. Forest Service Research FPL 82 Jan. 1968.
TAPPI. Acid-insoluble lignin in wood and pulp. T 222 om-88, TAPPI 1988.
Tarabanko, et al. Mechanism for the Catalytic Oxidation of Lignin to Vanillin. Kinetic and Catalitysis. 2004; 45(4):569-577.

Tejado, et al. Isocyanate modified lignins for formulations of novolac resins. ILI's 7th Forum and Eurolignin meeting, Barcelona 2005.
Telysheva. Applicability of a free radical (DPPH) method for estimation of antioxidant activity of lignin and its derivatives. The international Lignin Institute, 5th international Forum' Sep. 7, 2000, Bordeaux (France).
Terashima, et al. Solid state NMR spectroscopy of specifically 13C-enriched lignin in wheat straw from coniferin. Phytochemistry. 1997; 46(5):863-870.
The US Pushes for Advanced Biofuels Market Growth. Global Data; A report.2010: 1-7.
Thielemans, et al. Lignin Esters for Use in Unsaturated Thermosets: Lignin Modification and Solubility Modeling. Biomacromolecules. 2005; 6:1895-1905.
Thompson, et al. Comparison of Pretreatment Methods on the Basis of Available Surface Area. Bioresource Technology. 1992; 39:155-163.
Thomsen. How 'green' are algae farms for biofuel production? Biofuels. 2010; 1(4):515-517.
Timell, et al. The acid hydrolysis of glycosides II. Effect of substituents at C-5. Canadian Journal of Chemistry. 1965; 43:2296-2305.
Timell. The acid hydrolysis of glycosides I. General conditions and the effect of the nature of the aglycone. Canadian Journal of Chemistry. 1964; 42:1456-1471.
Timur, et al. Characterization and application of activated carbon produced from oak cups pulp. Journal of Analytical and Applied Pyrolysis. 2010; 89:129-136.
Toledano, et al. Characterization of key functional groups of lignin. 5th Italian meeting on lignocellulosic chemistry. Sep. 1-4, 2009— Villa Monastero Varenna (Lecco) Italy.
Toledano, et al. Study of fractionation of lignin by ultrafiltration and selective recipitation. 2009.
Tomani, et al. Development and demonstration of the lignoboost process. 2007.
Trickett. Utilization of Baggase for the production of C5 and C6 sugars. MS Thesis; University of Natal, Durban, South Africa. 1982.
Trinh et al. Fast Pyrolysis of Lignin Using a Pyrolysis Centrifuge Reactor. Energy & Fuels. 2013; 27 (7): 3802-3810.
Troitskii. Colloid chemical mechanism of the separation of some elements by extraction. Russ. Chem. Rev. 163; 32:116-120.
UK examination report dated Jul. 30, 2012 for GB 1205500.0.
UK search and examination report dated May 11, 2012 for GB Application No. 1205501.8.
UK search and examination report dated May 27, 2014 for GB Application No. 1208154.3.
UK search and examination report dated Jul. 18, 2012 for GB Application No. 1208154.3.
UK search and examination report dated Dec. 6, 2012 for GB Application No. 1205501.8.
Unal, et al. Dechlorination of Bleached Kraft Pulp by Laccase Enzyme Produced from Some White-Rot Fungi. Turk J Biol. 2001; 25:67-72.
Updegraff et al. Semimicro determination of cellulose in biological materials. Analytical biochemistry. 1969; 32(3):420-424.
Uraki, et al. Preparation of activated carbon fibers with large specific surface area from softwood acetic acid lignin. J Wood Sci. 2001; 47:465-469.
Urban, et al. Characterization of polymer-based monolithic capillary columns by inverse size-exclusion chromatography and mercury-intrusion porosimetry. Journal of Chromatography A. 2008; 1182:161-16.
U.S. Appl. No. 13/132,573, filed Sep. 15, 2011.
U.S. Appl. No. 13/195,721, filed Aug. 1, 2011.
U.S. Appl. No. 13/316,327, filed Dec. 9, 2011.
U.S. Appl. No. 13/320,535, filed Jan. 10, 2012.
U.S. Appl. No. 13/378,657, filed Dec. 15, 2011.
U.S. Appl. No. 13/380,504, filed Jan. 19, 2012.
U.S. Appl. No. 13/491,485, filed Jun. 7, 2012.
U.S. Appl. No. 13/499,638, filed Apr. 1, 2012.
U.S. Appl. No. 13/577,213, filed Aug. 3, 2012.
U.S. Appl. No. 13/577,215, filed Aug. 3, 2012.

(56) References Cited

OTHER PUBLICATIONS

U.S. Appl. No. 61/473,134, filed Apr. 7, 2011.
U.S. Appl. No. 61/483,777, filed May 9, 2011.
U.S. Appl. No. 61/487,319, filed May 18, 2011.
U.S. Appl. No. 61/524,350, filed Aug. 17, 2011.
U.S. Appl. No. 61/528,257, filed Aug. 28, 2011.
U.S. Appl. No. 61/539,196, filed Sep. 26, 2011.
U.S. Appl. No. 61/539,239, filed Sep. 26, 2011.
U.S. Appl. No. 61/539,272, filed Sep. 26, 2011.
U.S. Appl. No. 61/545,823, filed Oct. 11, 2011.
U.S. Appl. No. 61/552,402, filed Oct. 27, 2011.
U.S. Appl. No. 61/559,529, filed Nov. 14, 2011.
U.S. Appl. No. 61/561,181, filed Nov. 17, 2011.
USDA. A USDA Regional Roadmap to Meeting the Biofuels Goals of the Renewable Fuels Standard by 2022. A USDA Report. 2010.
Usde. Advanced Technologies for the Control of Sulfur Dioxide Emissions from Coal-Fired Boilers, A report on three projects conducted under separate. Clean Coal Technology. Topical Report No. 12, Jun. 1999.
Vaghela et al. Electrolytic synthesis of succinic acid in a flow reactor with solid polymer electrolyte membrane. Journal of Applied Electrochemistry. 2002; 32: 1189-1192.
Van Bramer. An Introduction to Mass Spectrometry. Widener University, Department of Chemistry, One University Place, Chester, PA 19013. 1998.
Van Dam. Characterization of Sulfur-free lignins from alkaline pulping of annual fibre crops. The international Lignin Institute, 5th international Forum' Sep. 7, 2000, Bordeaux (France).
Van Dam, et al. Emerging markets for lignin and lignin derivatives. The quest of taming the last of the "wild bio-polymers". 2005.
Van De Pas, et al. Epoxy Resins from Lignin-derived Phenols. SCION next generation biomaterials. Poster 2009.
Van Dyke. Enzymatic Hydrolysis of Cellulose—A Kinetic Study. For the degree of Doctor of Science at the Massachusetts Institute of Technology, Sep. 1972.
Van Sprongsen, et al. Separation and recovery of the constituents from lignocellulosic biomass by using ionic liquids and acetic acid as co-solvents for mild hydrolysis. Chemical Engineering and Processing. 2011; 50:196-199.
Van-Putten et al. Hydroxymethylfurfural, a versatile platform chemical made from renewable resources. Chemical reviews. 2013;113: 1499-1597.
Vasile, et al. Thermogravimetry (TG) and derivative thermogravimetry (DTG) of lignin. Analytical methods for lignin characterization. International Lignin Institute Version: 1.2 Last date of review: Aug. 2008.
Vassilev, et al. An overview of the chemical composition of biomass. Fuel, vol. 89, Issue 5, May 2010, pp. 913-933. Available online Nov. 10, 2009.
Vazquez, et al. Acetosolv pine lignin as copolymer in resins for manufacture of exterior grade plywoods. Bioresource Technology. 1999; 70:209-214.
Vazquez, et al. Effect of chemical modification of lignin on the gluebond performance of lignin-phenolic resins. Bioresource Technology. 1997; 60:191-198.
Vennestrom, et al. Beyond petrochemicals: the renewable chemicals industry. Angewandte Chemie Int. Ed. 2011; 50:10502-10509.
Von Sivers, et al. A techno-economical comparison of three processes for the production of ethanol from pine. Bioresource Technology. 1995; 51:43-52.
Vulfson, et al. Glycosidases in organic solvents: I. Alkyl-fl-glucoside synthesis in a water-organic two-phase system. Enzyme Microb. Technol. Dec. 1990; 12:950-954.
Vuori, et al. Liquefaction of Kraft Lignin: 1. Primary Reactions under Mild Thermolysis Conditions. Holzforschung—International Journal of the Biology, Chemistry, Physics and Technology of Wood , vol. 42 (3) de Gruyter—Jan. 1, 1988.
Vuyyuru et al. Conversion of Cellulosic Biomass into Chemicals using Heterogeneous and Electrochemical Catalysis. MS Thesis, Berlin University, 2012.

Wallmo, et al. Effect of precipitation conditions on properties of lignin from the LignoBoost process. 2007.
Wang. David Wang's Wood Chemistry Class. Basic Lignin Chemistry. 2011.
Wang et al. A Route for Lignin and Bio-Oil Conversion: Dehydroxylation of Phenols into Arenes by Catalytic Tandem Reactions. Angewandte Chemie. 2013; 52: 11499-11503.
Wang, et al. Influence of steaming explosion time on the physicchemical properties of cellulose from Lespedeza stalks (*Lespedeza crytobotrya*). Bioresource Technology. 2009; 100:5288-5294.
Wang, et al. Molecular Characteristics of Kraft-AQ Pulping Lignin Fractionated by Sequential Organic Solvent Extraction. Int. J. Mol. Sci. 2010; 11:2988-3001.
Wang, et al. Understanding the Conformation of Polysaccharides. Chapter 5. Copyright 2005 by Taylor & Francis Group, LLC.
Wang, et al. Understanding the Physical Properties of Food Polysaccharides. Chapter 4. Copyright 2005 by Taylor & Francis Group, LLC.
Wang. Thermal Modification of Wood. Faculty of Forestry University of Toronto. 2011.
Warren. Future Lower Cost Carbon Fiber for Autos: International Scale-up & What is Needed. Oak Ridge National Laboratory, Tennessee, USA. 2007.
Wasserscheid & Welton. Ionic Liquids in Synthesis. A book ; Published by Wiley-VCH Verlag GmbH & Co. KGaA. 2007:1-709.
Wei, et al. Effects of surfactant on biochemical and hydrothermal conversion of softwood hemicellulose to ethanol and furan derivatives. Process Biochemistry. 2011; 46(9): 1785-1792.
Weingarten, et al. Kinetics of furfural production by dehydration of xylose in a biphasic reactor with microwave heating. Green Chem. 2010; 12:1423-1429.
Werner et al. Ionic liquids in chemical engineering. Annual review of chemical and biomolecular engineering. 2010; 1: 203-230.
Williams. Ethanol production potential and costs from lignocellulosic resources in California. 15th European Biomass Conference & Exhibition, May 7-11, 2007, Berlin, Germany.
Wilson, et al. Detection of tannins in modern and fossil barks and in plant residues by high-resolution solid-state $^{13}$C nuclear magnetic resonance. Org. Geochem. 1988; 12(6):539-546.
Winandy, et al. Wood-plastic composites using thermomechanical pulp made from oxalic acid-pretreated red pine chips. 7th Global WPC and Natural Fibre Composites Congress and Exhibition, Jun. 18-19, 2008 in Kassel / Germany.
Winston, et al. Characterization of the lignin residue from hydrolysis of sweetgum wood with superconcentrated hydrochloric acid. Holzforschung Bd.1986; 40:Suppl. 45-50.
Wood, et al. Determination of Methanol and Its Application to Measurement of Pectin Ester Content and Pectin Methyl Esterase Activity. Analytical biochemistry. 1971; 39:418-428.
Woodbridge et al. Nitrocellulose from wood pulp. J. Ind.Eng. Chem. 1920; 12(4):380-384.
Wood-Ethanol Report. Environment Canada. 1999.
Wooley, et al. Lignocellulosic biomass to ethanol process design and economics utilizing co-current dilute acid prehydrolysis and enzymatic hydrolysis current and futuristic scenarios. National Renewable Energy Laboratory. NREL/TP 580-26157. Jul. 1999.
Wright et al. Techno-Economic Analysis of Biomass Fast Pyrolysis to Transportation Fuels. Technical Report: NREL/TP-6A20-46586. 2010.
Wyman. Biomass ethanol: Technical Progress, Opportunities, and Commercial Challenges. Annu. Rev. Energy Environ. 1999; 24:189-226.
Wyman, et al. Comparative sugar recovery data from laboratory scale application of leading pretreatment technologies to corn stover. Bioresource Technology. 2005; 96: 2026-2032.
Wyman, et al. Coordinated development of leading biomass pretreatment technologies. Bioresource Technology. 2005; 96:1959-1966.
Wyman et al. Pretreatment : The Key to Unlocking Low Cost Cellulosic Ethanol Ethanol Production in Brazil and the United States. Presentation. CAFI. 2007.

(56) References Cited

OTHER PUBLICATIONS

Wyman. Potential Synergies and Challenges in Refining Cellulosic Biomass to Fuels, Chemicals, and Power. Biotechnol. Prog. 2003; 19:254-262.
Wyman. Twenty Years of Trials, Tribulations, and Research Progress in Bioethanol Technology. Applied Biochemistry and Biotechnology. 2001; 91-93:5-21.
Wyman. What is (and is not) vital to advancing cellulosic ethanol. Trends in Biotechnology. 2007; 25(4):153-157.
Xiang, et al. Heterogeneous Aspects of Acid Hydrolysis of $\alpha$-Cellulose. Applied Biochemistry and Biotechnology. 2003; 105-108:505-514.
Xie, et al. Opportunities with Wood Dissolved in Ionic Liquids. In Cellulose Solvents: Foe Analysis, Shaping and Chemical Modification. Chapter 19. 2010;343-363.
Xing, et al. Production of furfural and carboxylic acids from waste aqueous hemicellulose solutions from the pulp and paper and cellulosic ethanol industries. Energy & Environmental Science. 2011; 4: 2193-2205.
Yang et al. Optimization of furfural production from D-xylose with formic acid as catalyst in a reactive extraction system. Bioresource technology. 2013; 133 : 361-369.
Yang, et al. Pretreatment: the key to unlocking low-cost cellulosic ethanol. Biofuels, Bioprod. Bioref. 2008; 2:26-40.
Yang et al. Synthesis of furfural from xylose, xylan, and biomass using AlCl3.6H2O in biphasic media via xylose isomerization to xylulose. ChemSusChem. 2012; 5: 405-410.
Ye, et al. Spontaneous High-Yield Production of Hydrogen from Cellulosic Materials and Water Catalyzed by Enzyme Cocktails. ChemSusChem. 2009; 2:149-152 .
Yeoh, et al. Comparisons between different techniques for water-based extraction of pectin from orange peels. Desalination 2008; 218:229-237.
Yoshida, et al. Gasification of biomass model compounds and real biomass in supercritical water. Biomass and Bioenergy.2004; 26:71-78.
Yuan, et al. Hydrolytic degradation of alkaline lignin in hot-compressed water and ethanol. Bioresource Technology 101 (2010) 9308-9313.
Yusmawati et al. Optical Properties and Sugar Content Determination of Commercial Carbonated Drinks using Surface Plasmon Resonance. American Journal of Applied Sciences. 2007;4: 1-4.
Zahalka, et al. Esterification of 1,4-dichlorobutane with sodium formate under solid-liquid phase transfer catalysis. A kinetic study. Can. J. Chem. 1989; 67:245-249.
Zahalka, et al. One-Pot Conversion of Primary Alkyl Chlorides and Dichlorides into Alcohols, Diols and Ethers via Formic Ester Intermediated under Phase-Transfer Conditions. Communications, Sep. 1986; 763-765.
Zahedifar. Novel uses of lignin and hemicellulosic sugars from acidhyrolysed lignocellulosic materials. for the degree of Doctor of Philosophy, in the University of Aberdeen, Sep. 1996.
Zakzeski, et al. The Catalytic Valorization of Lignin for the Production of Renewable Chemicals. Chem. Rev. 2010; 110:3552-3599.
Zhang et al. Conversion of Xylan and Xylose into Furfural in Biorenewable Deep Eutectic Solvent with Trivalent Metal Chloride Added. BioResources; 8(4);6014-6025.
Zhang, et al. Conversion of xylan, d-xylose and lignocellulosic biomass into furfural using AlCl3 as catalyst in ionic liquid. Bioresource technology. 2013; 130: 110-116.
Zhang et al. Hydrodeoxygenation of Lignin-Derived Phenolic Monomers and Dimers to Alkane Fuels over Bifunctional Zeolite-Supported Metal Catalysts. Substainable Chemistry and Engineering; 2013: A-I.
Zhang, et al. Quantitative 2D HSQC NMR Determination of Lignin-sub Structures by Selecting Suitable Internal Standard References. 2007.
Zhang, et al. Solid acids as catalysts for the conversion of D-xylose, xylan and lignocellulosics into furfural in ionic liquid. Bioresource technology. 2013; 136: 515-521.
Zhang, et al. Vapor Pressure Measurements for the H2SO4/HNO3/H2O and H2SO4/HCl/H2O Systems: Incorporation of Stratospheric Acids into Background Sulfate Aerosols. J. Phys. Chem. 1993; 97:8541-8548.
Zhang, et al. Vapor-Liquid Equilibria for Water+Hydrochloric Acid +Magnesium Chloride and Water+Hydrochloric Acid +Calcium Chloride Systems at Atmospheric Pressure. Chinese J. Chem. Eng. 2006; 14(2):276-280.
Zhang. Reviving the carbohydrate economy via multi-product lignocellulose biorefineries. J Ind Microbiol Biotechnol. 2008; 35:367-375.
Zhao et al. Aromatics Production via Catalytic Pyrolysis of Pyrolytic Lignins from Bio-Oil. Energy & Fuels. 2010; 24: 5735-5740.
Zhao, et al., Organosolv pretreatment of lignocellulosic biomass for enzymatic hydrolysis, Appl Microbiol Biotechnol (2009) 82:815-827.
Zhao, et al. Small-scale mashing procedure for predicting ethanol yield of sorghum grain. Journal of Cereal Science. 2009; 49:230-238.
Zhao, et al. Supercritical hydrolysis of cellulose for oligosaccharide production in combined technology. Chem. Eng. J. 2009; 150:411-417.
Zheng, et al. Electron beam induced changes in the surface properties of starch films functionalized by lignin. Italic 5 conference—Sep. 2-4—Varenna-2009.
Zheng, et al. Overview of biomass pretreatment for cellulosic ethanol production. Int J Agric & Biol Eng. 2009; 2(3):51-68.
Zheng, et al. Phenolation of walnut shell using sulfuric acid as a catalyst and application to PF resin adhesives. Abstracts / Journal of Biotechnology 136S (2008) S402-S459, doi:10.1016/j.jbiotec.2008.07.950.
Zheng, et al. Supercritical carbon dioxide explosion as a pretreatment for cellulose hydrolysis. Biotechnology Letters. Aug. 1995; 17(8):845-850.
Zhu, et al. Understanding methanol formation in pulp mills. 1999 International Environmental Conference, pp. 139-143.
Zimbardi, et al. Acid impregnation and steam explosion of corn stover in batch processes. Industrial Crops and Productions. 2007; 26:195-206.
Zinoviev, et al. Background Paper on biofuels Production Technologies. International Center for Science and High Technology and UNIDO. Nov. 2007; 1-106.
Zolotov. Hydration and solvation of acids and salts undergoing extraction. Russ. Chem. Rev. 1963; 32:107-116.
Zorina, et al. Study of acid heterogeneous hydrolysis of pulp. USSR. Editor(s): Kiprianov, A. I. Khim. Pererab. Drev. (1982), 35-8. Publisher: Leningr. Lesotekh. Akad., Leningrad, USSR CODEN: 49HIA6. Abstract only.
Zou, et al. Preparation of Activated Carbons from Chinese Coal and Hydrolysis Lignin. Adsorption Science & Technology. 2001; 19(1): 59-72.
Co-pending U.S. Appl. No. 16/243,888, filed Jan. 9, 2019.
Raveendran et al. Influence of mineral matter on biomass pyrolysis characteristics. Fuel 74(12):1812-1822 (1995).
Co-pending U.S. Appl. No. 16/560,653, filed Sep. 4, 2019.
Hirajama et al. Semibatch Hydrothermal Hydrolysis of Cellulose in a Filter Paper by Dilute Organic Acids. Ind Eng Chem Res 54:6052-6059 (May 22, 2015).
Zhuang et al. Analysis of cellulose hydrolysis products in extremely low acids. Nongye Gongcheng Xuebao 23(2):177-182 (2007). Abstract only. 1 page.
Grzenia, et al. Detoxification of biomass hydrolysates by reactive membrane extraction. Journal of Membrane Science. vol. 348, Issues 1-2, Feb. 15, 2010, pp. 6-12.

* cited by examiner

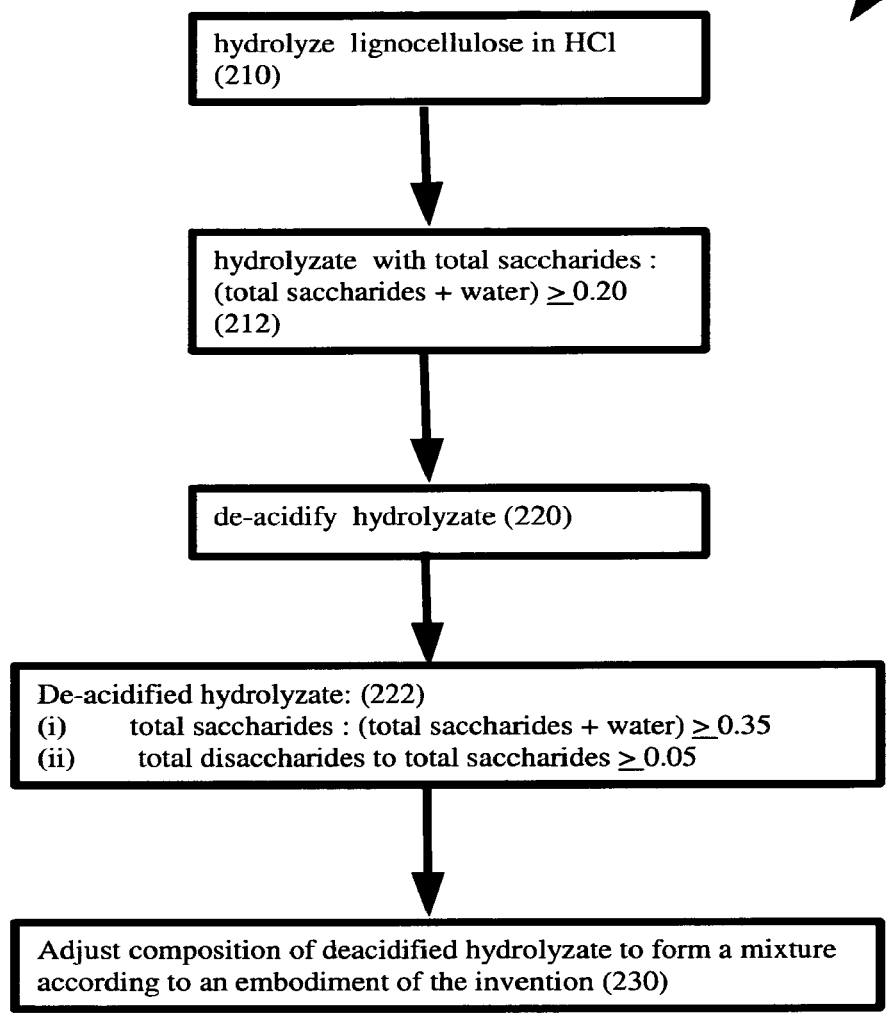

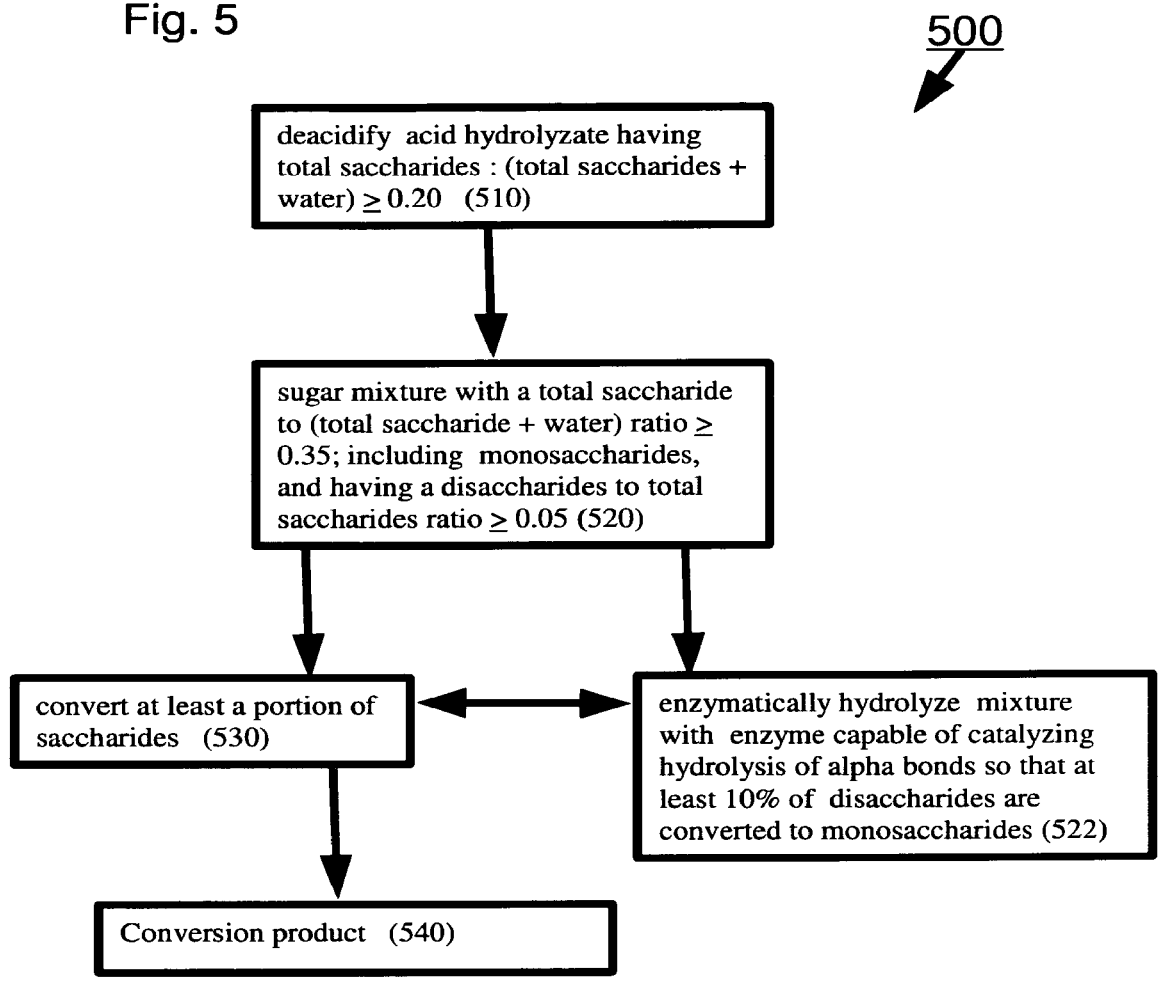

SUGAR MIXTURES AND METHODS FOR PRODUCTION AND USE THEREOF

CROSS-REFERENCE

This application is a continuation of U.S. application Ser. No. 15/191,376, filed Jun. 23, 2016, which is a continuation of U.S. application Ser. No. 13/378,657, filed Jan. 19, 2012, which is a National Stage 371 application of PCT/IL2011/000509, filed Jun. 26, 2011, which claims the benefit of U.S Application Nos. 61/358,894, filed Jun. 26, 2010, 61/491,243, filed May 30, 2011, and 61/500,169, filed Jun. 23, 2011, each of which is incorporated herein by reference in its entirety.

RELATED APPLICATIONS

In accord with the provisions of 35 U.S.C. § 119(e) and § 363, this application claims the benefit of:

U.S. 61/358,894 filed 26 Jun. 2010 by Aharon EYAL and entitled "Fermentation Feedstock Precursor and Methods for the Production Thereof"; and U.S. 61/491,243 filed 30 May 2011 by Robert JANSEN et al. and entitled "Lignin Compositions, Systems and Methods for Processing Lignin and/or HCl"; and U.S. 61/500,169 filed 23 Jun. 2011 by Aharon EYAL et al. and entitled "Sugar Mixtures and Methods for Production and Use thereof";

In accord with the provisions of 35 U.S.C. § 119(a) and/or § 365(b), this application claims priority from:

prior Israeli application IL206896 filed on 8 Jul. 2010 by Aharon EYAL and entitled "Fermentation Feedstock Precursor and Methods for the Production Thereof"; and prior Israeli application IL207313 filed on 29 Jul. 2010 by Aharon EYAL et al. and entitled "Methods for the Production of a Fermentation Feedstock"; and prior PCT application IL2011/000130 filed on 6 Feb. 2011 by Aharon EYAL et al. and entitled " Methods for the Separation of HCl from a Carbohydrate and Compositions Produced thereby" which corresponds to IL 210998 filed 1 Feb. 2011.

Each of these priority documents is fully incorporated by reference.

This application is also related to the following co-pending applications which are each fully incorporated herein by reference:

U.S. 61/473,134 filed 7 Apr. 2011 by Aharon EYAL and entitled "Lignocellulose Conversion Processes and Products"; and U.S. 61/483,663 filed 7 May 2011 by Aharon EYAL and entitled "Lignocellulose Conversion Processes and Products"

U.S. 61/483,777 filed 9 May 2011 by Robert JANSEN et al. and entitled "Hydrolysis Systems and Methods"; and U.S. 61/487,319 filed 18 May 2011 by Robert JANSEN et al. and entitled "Hydrolysis Systems and Methods"; and prior Israeli application IL 211093 filed on 6 Feb. 2011 by Aharon EYAL and entitled "A Method for Processing a Lignocellulosic Material and for the Production of a Carbohydrate Composition"

FIELD OF THE INVENTION

This invention relates to sugars and production and use thereof.

BACKGROUND OF THE INVENTION

The carbohydrate-conversion industry is large and rapidly increasing in size. Currently, about 100 million tons of carbohydrates are fermented annually, primarily to provide fuel-grade ethanol. This number is predicted to triple in the next decade.

Millions of tons of carbohydrates are also fermented every year to provide food and feed products, such as citric acid and lysine. Also large and increasing is fermentation to produce other products, such as monomers for the polymer industry, e.g. lactic acid for the production of polylactide.

Fermentation media typically include, in addition to carbohydrates and/or another carbon source, other nutrients and factors such as nitrogen sources, minerals, vitamins, and growth factors. In some cases, fermentation media comprise well identified chemicals. In other cases, various preparations (e.g. yeast extract or tryptone broth) are incorporated without fully understanding the effect of each component in the preparation. Some of those preparations result from natural sources, such as extracts. Some of those preparations are of relatively high cost.

With the advent of molecular biology techniques, a new generation of industrial fermentation, also known as conversion, based upon genetically modified microorganisms has emerged. In some cases these microorganisms rely upon inducible promoters for induction of a specific gene. Some of the inducible promoters respond to specific sugars.

Although conversion of lignocellulosic material to carbohydrates via enzyme-catalyzed and/or acid-catalyzed hydrolysis of polysaccharides and pyrolysis of lignocellulosic material have been previously described, industrial scale application of the proposed technologies has presented technical problems which remain to be overcome. Hydrolysis of hemicellulose is relatively easy, but hydrolysis of cellulose (typically more than 50% of total polysaccharides) is more difficult due to its partial crystalline structure.

This application refers to various solvents defined in terms of Hoy's cohesion parameter Delta-P and/or Delta-H. By way of review:

Delta-P is the polarity related component of Hoy's cohesion parameter and delta-H is the hydrogen bonding related component of Hoy's cohesion parameter.

The cohesion parameter, as referred to above or, solubility parameter, was defined by Hildebrand as the square root of the cohesive energy density:

$$\delta = \sqrt{\frac{\Delta E_{vap}}{V}}$$

where $\Delta E_{vap}$ and V are the energy or heat of vaporization and molar volume of the liquid, respectively. Hansen extended the original Hildebrand parameter to a three-dimensional cohesion parameter. According to this concept, the total solubility parameter, delta, is separated into three different components, or, partial solubility parameters relating to the specific intermolecular interactions:

$$\delta^2 = \delta_d^2 + \delta_p^2 + \delta_h^2$$

in which delta-D, delta-P and delta-H are the dispersion, polarity, and Hydrogen bonding components, respectively. Hoy proposed a system to estimate total and partial solubility parameters. The unit used for those parameters is $MPa^{1/2}$. A detailed explanation of that parameter and its components can be found in "CRC Handbook of Solubility Parameters and Other Cohesion Parameters", second edition, pages 122-138. That and other references provide tables with the parameters for many compounds. In addition, methods for calculating those parameters are provided.

SUMMARY OF THE INVENTION

One aspect of some embodiments of the invention relates to heterogeneous sugar mixtures. The term "sugar" as used in this specification and the accompanying claims refers to monosaccharides and oligosaccharides (disaccharides or greater) soluble in water at 25 degrees centigrade. Throughout this application, the term disaccharide refers to sugar dimers and "higher oligosaccharides" or "higher saccharide" refers to oligomers comprising three or more sugar units. According to various exemplary embodiments of the invention dimers may be homo-dimers and/or hetero-dimers. Alternatively or additionally, higher oligosaccharides may include same and/or different sugar units.

In many exemplary embodiments of the invention, the sugar mixtures result from acid hydrolysis of lignocellulosic or "woody" substrates. In some exemplary embodiments of the invention, acid hydrolysis is conducted with HCl, optionally at a concentration of 37% W/W HCl/[HCl+water], optionally 39, 41, 43 or even 45% HCl on the same basis. In some exemplary embodiments of the invention, the hydrolysis is conducted at temperatures below 50 degrees centigrade, optionally below 40 degrees, optionally below 30 degrees, optionally at 25 degrees or less. In some exemplary embodiments of the invention, at least a portion of the hydrolysis is conducted at 20 degrees or less, optionally 15 degrees or less.

According to various exemplary embodiments of the invention the sugar mixture is provided as a syrup and/or liquid, optionally including residual acid from hydrolysis. Total sugar concentrations in such a syrup/liquid can be 15, 20, 25, 30, 35, 40, 45 or 50% by weight or intermediate or higher percentages. Optionally, the mixture is provided as dry crystals.

In some exemplary embodiments of the invention, a percentage of oligosaccharides to total saccharides in the mixture is greater than 4, optionally 6, optionally 8, optionally 10, optionally 15% or intervening or greater percentages.

In some exemplary embodiments of the invention, a percentage of disaccharides to total saccharides in the mixture is greater than 3, optionally 5, optionally 7, optionally 10% or intervening or greater percentages.

"Disaccharide" indicates two sugars connected by an alpha bond or by a beta bonds or bonded via various hydroxyls on the molecule, and combinations thereof.

In some exemplary embodiments of the invention, a percentage of pentoses to total saccharides in the mixture is greater than 3, optionally 5, optionally 7, optionally 10% or intervening or greater percentages. Optionally, at least a portion of the pentose is present as part of a disaccharide or longer oligosaccharide.

According to various exemplary embodiments of the invention the mixture includes at least one alpha-bonded di-glucose and/or at least one beta-bonded di-glucose. Optionally, at least a portion of the di-glucoses are present as parts of higher oligosaccharides.

In some exemplary embodiments of the invention, residual acid (e.g. HCl) may be present in the mixture. Various exemplary embodiments of the invention are concerned with ways to remove this residual acid. Optionally, such removal contributes to added value for use in downstream processes (e.g. fermentation). In some exemplary embodiments of the invention, removal of residual acid involves extraction with an extractant containing an alcohol. Optionally, two or more extractions are conducted. In some exemplary embodiments of the invention, at least one of the extractions employs a mixture of two solvent types.

Another aspect of some embodiments of the invention relates to hydrolyzing a lignocellulosic substrate in HCl to form a hydrolyzate comprising total saccharides to (total saccharides+water) of at least 20%, optionally 25%, optionally 30% by weight and de-acidifying the hydrolyzate while increasing the sugar concentration. Optionally, the sugar concentration is increased to 35, 40, 45 or 50% or greater or intermediate percentages. In some exemplary embodiments of the invention, the disaccharides in the de-acidified hydrolyzate are at least 5%, optionally 10%, optionally 20%, optionally 30% of the total saccharides or intermediate or greater percentages. Optionally, a portion of the saccharides in the de-acidified hydrolyzate can be enzymatically digested.

Another aspect of some embodiments of the invention relates to fermenting such a sugar mixture in a fermentor to produce a desired fermentation product or "conversion product". Optionally, the fermentation product can include one or more of alcohols, carboxylic acids, amino acids, monomers for production of industrially important polymers and proteins. In some exemplary embodiments of the invention, a fermentation product is produced and then converted into the monomer (e.g. 3-hydroxy-propionic acid to be converted into acrylic acid, which is then polymerized). In other exemplary embodiments of the invention, the monomer is produced directly (e.g. lactic acid as a source of polylactide).

Optionally, the proteins are heterologous proteins produced by genetically modified microorganisms. Such heterologous proteins include, but are not limited to, hormones, enzymes (e.g. cellulases), growth factors, cytokines and antibodies. Optionally, the antibodies are fusion proteins including a non-immunoglobulin domain.

An additional aspect of some embodiments of the invention relates to enzymatic hydrolysis of a portion of the sugars in the mixture. For purposes of this specification and the accompanying claims, the term "enzyme" indicates a single enzyme or a mixture including two or more enzymes. Optionally, an enzyme is provided as a crude preparation (e.g. cell extract) characterized by a type and/or level of activity, as opposed to a precise molecular definition. According to various exemplary embodiments of the invention enzymes capable of hydrolyzing alpha and/or beta bonds are used. Optionally, specificity for a desired bond type can be achieved by appropriate enzyme selection and/or selection of suitable reaction conditions. In some exemplary embodiments of the invention at least 10% of disaccharides in the mixture are converted to monosaccharides by this enzymatic treatment. Alternatively or additionally, at least 10% of oligosaccharides in the mixture are enzymatically hydrolyzed to release additional monosaccharides. In some exemplary embodiments of the invention, enzymes are immobilized. Optionally, immobilization can be on beads and/or a membrane. In some exemplary embodiments of the invention, immobilization contributes to an increase in yield of an enzymatic hydrolysis product per unit of enzyme.

For purposes of this specification and the accompanying claims an "S1 solvent" or "S1" is an organic solvent with a water solubility of less than 15% characterized by a polarity related component of Hoy's cohesion parameter (delta-P) between 5 and 10 $MPa^{1/2}$ and/or by a hydrogen bonding related component of Hoy's cohesion parameter (delta-H) between 5 and 20 $MPa^{1/2}$. In some exemplary embodiments of the invention, HCl tends to selectively transfer to an S1 solvent upon contact therewith.

For purposes of this specification and the accompanying claims an "S2 solvent" or "S2" is an organic solvent having a water solubility of at least 30% and characterized by a delta-P greater than 8 $MPa^{1/2}$ and/or a delta-H greater than 12 $MPa^{1/2}$. In some exemplary embodiments of the invention, HCl tends to selectively transfer to an extractant including both S1 and S2 solvents upon contact therewith.

For purposes of this specification and the accompanying claims "extract" and "extraction" indicate bringing an extractant into contact with a substrate and then separating an extract from an extracted substrate.

According to various exemplary embodiments of the invention an extraction may be on an indicate stream or fraction per se or on a modified stream or fraction. Optional modifications include, but are not limited to, dilution, concentration, mixing with another stream or fraction, temperature adjustment, and filtration. Optionally, two or more modifications may be performed prior to extraction.

"Woody materials" or "lignocellulosic materials" are an attractive and environment-friendly substrate for sugar production since they are obtained from renewable resources. Many non-food lignocellulosic materials are potential sources of soluble carbohydrates. These lignocellulosic materials include, but are not limited to, wood and by-products of wood processing (e.g. chips, sawdust, and shavings) as well as residual plant material from agricultural products and paper industry byproducts (e.g. cellulose containing residues and/or paper pulp)

Residual plant material from agricultural products includes processing by-products and field remains.

Processing by-products include, but are not limited to, corn cobs, sugar cane bagasse, sugar beet pulp, empty fruit bunches from palm oil production, straw (e.g. wheat or rice), soy bean hulls, residual meals from the vegetable oil industry (e.g. soybean, peanut, corn or rapeseed), wheat bran and fermentation residue from the beer and wine industries.

Field remains include, but are not limited to, corn stover, post harvest cotton plants, post harvest soybean bushes and post harvest rapeseed plants.

Lignocellulosic materials also include "energy crops" such as switch grass and broom grass which grow rapidly and generate low-cost biomass specifically as a source of carbohydrates.

These lignocellulosic carbohydrate sources contain cellulose, hemicellulose and lignin as their main components and also contain mineral salts (ashes) and lipophilic organic compounds, such as tall oils. The degree and type of theses non-carbohydrate materials can create technical problems in production of soluble carbohydrates.

Lignocellulosic materials typically contain 65-80% cellulose and hemicelluloses on a dry matter basis. Cellulose and hemicellulose are polysaccharides which can release carbohydrates suitable for fermentation and/or chemical conversion to products of interest if they are hydrolyzed. Lignin is typically resistant to acid hydrolysis.

It will be appreciated that the various aspects described above relate to solution of technical problems associated with obtaining specific ratios of disaccharides and/or higher oligomers relative to total saccharides produced by acid hydrolysis of a lignocellulosic substrate.

Alternatively or additionally, it will be appreciated that the various aspects described above relate to solution of technical problems associated with the need for defined mixtures of sugars containing specific disaccharides and/or higher oligomers. In many cases this "need" is defined by a specific downstream application.

In some exemplary embodiments of the invention, there is provided a sugar mixture including: (i) monosaccharides; (ii) oligosaccharides in a ratio to total saccharides≥0.06; (iii) disaccharides in a ratio to total saccharides≥0.05; (iv) pentose in a ratio to total saccharides≥0.05; (v) at least one alpha-bonded di-glucose; and (vi) at least one beta-bonded di-glucose.

Optionally, the mixture has a higher oligosaccharides in a ratio to total saccharides≤0.2.

Optionally, the mixture has a ratio of at least one of the alpha-bonded di-glucose and the beta-bonded di-glucose relative to total saccharides is ≥0.01.

Optionally, the mixture has a ratio of at least one of the alpha-bonded di-glucose and the beta-bonded di-glucose relative to total saccharides is ≥0.03.

Optionally, the alpha-bonded di-glucose includes at least one member of the group consisting of maltose, isomaltose and trehalose.

Optionally, the beta-bonded di-glucose includes at least one member selected from the group consisting of gentiobiose, sophorose and cellobiose.

In some exemplary embodiments of the invention, there is provided a method including (a) hydrolyzing a lignocellulosic material in a medium containing HCl in a ratio to (HCl+water)≥0.37 to form a hydrolyzate including total saccharides in a ratio to (total saccharides+water)≥0.20 by weight; (b) de-acidifying the hydrolyzate to form a de-acidified hydrolyzate including: (i) total saccharides in a ratio to (total saccharides+water)≥0.35 and; (ii) total disaccharides in a ratio to total saccharides≥0.05; and (c) adjusting a composition of the de-acidified hydrolyzate to form a mixture according to any of claims 1 to 6.

In some exemplary embodiments of the invention, there is provided a method including (a) hydrolyzing a lignocellulosic material in a medium containing HCl in a ratio to (HCl+water)≥0.37 by weight to form a hydrolyzate including total saccharides in a ratio to (total saccharides+water)≥0.20 by weight; (b) de-acidifying the hydrolyzate to form a de-acidified hydrolyzate including a mixture as described above.

Optionally, the hydrolyzing is conducted in a counter-current mode of operation.

Optionally, the hydrolyzing is conducted at a temperature of less than 25° C.

Optionally, the lignocellulosic material includes softwood, for example, pine.

Optionally, the de-acidifying includes selective extraction of HCl and water with an extractant including alcohol.

Optionally, the de-acidifying is conducted at a temperature of less than 80° C.

In some exemplary embodiments of the invention, there is provided a method including: (i) providing a preparation including HCl and a sugar mixture according to any of claims 1 to 6, and (ii) de-acidifying the preparation to form a de-acidified preparation.

Optionally, the de-acidifying includes selective extraction of HCl with an extractant including alcohol.

Optionally, the de-acidifying is conducted at a temperature of less than 80° C.

In some exemplary embodiments of the invention, there is provided a method including: (a) providing a fermentor; and (b) fermenting a medium including a sugar mixture as described above in the fermentor to produce a fermentation product.

In some exemplary embodiments of the invention, there is provided a method including: (a) providing a fermentor; and (b) fermenting a medium including a de-acidified hydrolyzate according as described above or a de-acidified preparation as described above to produce a fermentation product.

Optionally, the fermentation product includes at least one member selected from the group consisting of alcohols, carboxylic acids, amino acids, monomers for the polymer industry and proteins.

Optionally, the method includes processing the fermentation product to produce a consumer product selected from the group consisting of detergent, polyethylene-based products, polypropylene-based products, polyolefin-based products, polylactic acid (polylactide)-based products, polyhydroxyalkanoate-based products and polyacrylic-based products.

Optionally, the detergent includes a sugar-based surfactant, a fatty acid-based surfactant, a fatty alcohol-based surfactant, or a cell-culture derived enzyme.

Optionally, the polyacrylic-based product is selected from plastics, floor polishes, carpets, paints, coatings, adhesives, dispersions, flocculants, elastomers, acrylic glass, absorbent articles, incontinence pads, sanitary napkins, feminine hygene products, and diapers.

Optionally, the polyolefin-based products are selected from milk jugs, detergent bottles, margarine tubs, garbage containers, water pipes, absorbent articles, diapers, non wovens, HDPE toys and HDPE detergent packagings.

Optionally, the polypropylene based products are selected from absorbent articles, diapers and non wovens.

Optionally, the polylactic acid based products are selected from packaging of agriculture products and of dairy products, plastic bottles, biodegradable products and disposables.

Optionally, the polyhydroxyalkanoate based products are selected from packaging of agriculture products, plastic bottles, coated papers, molded or extruded articles, feminine hygiene products, tampon applicators, absorbent articles, disposable nonwovens and wipes, medical surgical garments, adhesives, elastometers, films, coatings, aqueous dispersants, fibers, intermediates of pharmaceuticals and binders.

Optionally, the fermentation product includes at least one member of the group consisting of ethanol, butanol, isobutanol, a fatty acid, a fatty acid ester, a fatty alcohol and biodiesel.

Optionally, the method includes processing of the fermentation product to produce at least one product selected from the group consisting of an isobutene condensation product, jet fuel, gasoline, gasohol, diesel fuel, drop-in fuel, diesel fuel additive, and a precursor thereof.

Optionally, the gasahol is ethanol-enriched gasoline or butanol-enriched gasoline.

Optionally, the product is selected from the group consisting of diesel fuel, gasoline, jet fuel and drop-in fuels.

In some exemplary embodiments of the invention, there is provided a consumer product, a precursor of a consumer product, or an ingredient of a consumer product produced from a fermentation product as described above.

In some exemplary embodiments of the invention, there is provided a consumer product, a precursor of a consumer product, or an ingredient of a consumer product including at least one fermentation product produced by a method as described above, wherein the fermentation product is selected from carboxylic and fatty acids, dicarboxylic acids, hydroxylcarboxylic acids, hydroxyl di-carboxylic acids, hydroxyl-fatty acids, methylglyoxal, mono-, di-, or poly-alcohols, alkanes, alkenes, aromatics, aldehydes, ketones, esters, biopolymers, proteins, peptides, amino acids, vitamins, antibiotics, and pharmaceuticals.

Optionally, the product is ethanol-enriched gasoline, jet fuel, or biodiesel.

In some exemplary embodiments of the invention, there is provided consumer product, a precursor of a consumer product, or an ingredient of a consumer product according as described above, wherein the consumer product has a ratio of carbon-14 to carbon-12 of about $2.0 \times 10^{-13}$ or greater.

Optionally, the consumer product including an ingredient according as described above and an additional ingredient produced from a raw material other than lignocellulosic material.

Optionally, the ingredient and the additional ingredient produced from a raw material other than lignocellulosic material are essentially of the same chemical composition.

Optionally, the consumable product includes a marker molecule at a concentration of at least 100 ppb.

Optionally, the marker molecule is selected from the group consisting of furfural, hydroxy-methyl furfural, products of furfural or hydroxy-mathylfurfural condensation, color compounds derived from sugar caramelization, levulinic acid, acetic acid, methanol, galcturonic acid, and glycerol.

In some exemplary embodiments of the invention, there is provided a method including:

(a) de-acidifying an acid hydrolyzate including total saccharides in a ratio to (total saccharides+water)≥0.20 by weight to produce a sugar mixture with total saccharides in a ratio to (total saccharides+water) ratio≥0.35; the mixture including monosaccharides, the mixture having disaccharides in a ratio to total saccharides≥0.05; and (b) enzymatically hydrolyzing the mixture with an enzyme capable of catalyzing hydrolysis of alpha bonds in the mixture so that at least 10% of the disaccharides are converted to monosaccharides; and (c) converting at least a portion of the saccharides to a conversion product.

Optionally, the sugar mixture includes higher oligosaccharides.

Optionally, at least 10% of the higher oligosaccharides are hydrolyzed.

Optionally, the acid hydrolyzate is the result of counter-current hydrolysis.

Optionally, the acid hydrolyzate is the result of hydrolysis conducted at a temperature of less than 25° C.

Optionally, the de-acidifying includes extraction with an extractant including an alcohol.

Optionally, the de-acidifying is conducted at a temperature of less than 80° C.

Optionally, the enzymatically hydrolyzing includes use of an enzyme capable of catalyzing hydrolysis of beta bonds.

Optionally, the enzyme includes at least one enzyme selected from the group consisting of amylases cellulases, hemicellulases, transglucosidases, glucoamylases, alpha-glucosidases and pullulanases.

Optionally, the enzymatically hydrolyzing includes use of an immobilized enzyme.

Optionally, at least a portion of the converting is conducted simultaneously with the enzymatically hydrolyzing.

Optionally, the total saccharides ratio to (total saccharides+water) is ≥0.15 during the enzymatically hydrolyzing.

Optionally, the enzymatically hydrolyzing includes incubation of the mixture with a microorganism.

Optionally, the converting includes fermentation.

Optionally, the sugar mixture includes at least one pentose in a ratio to total saccharides≥0.05.

Optionally, the de-acidifying includes extracting the hydrolyzate, with a first extractant including an S1 solvent to form an HCl-carrying first extract and an HCl-depleted sugar solution.

Optionally, the de-acidifying includes including chromatographically separating the HCl-depleted sugar solution to produce a monosaccharide enriched monomer cut and an acid cut enriched in disaccharides and higher oligosaccharides.

Optionally, the de-acidifying includes subsequently extracting the HCl-depleted sugar solution with a second extractant including S1 and a second solvent (S2).

Optionally, the S1 of the extracting and the subsequently extracting each independently include at least one member selected from the group consisting of alcohols, ketones and aldehydes having at least 5 carbon atoms and combinations thereof.

Optionally, the second extractant is characterized by at least one of:
a delta-P greater than the delta-P of the first extractant by at least 0.2 $MPa^{1/2}$; and
a delta-H greater than the delta-H of the first extractant by at least 0.2 $MPa^{1/2}$.

Optionally, S2 includes at least one member selected from the group consisting of $C_1$-$C_4$ mono- or poly-alcohols, aldehydes and ketones.

Optionally, a ratio of HCl to total saccharides in the sugar mixture is ≤0.03 by weight.

Unless otherwise defined, all technical and scientific terms used herein have the same meaning as commonly understood by one of ordinary skill in the art to which this invention belongs. Although suitable methods and materials are described below, methods and materials similar or equivalent to those described herein can be used in the practice of the present invention. In case of conflict, the patent specification, including definitions, will control. All materials, methods, and examples are illustrative only and are not intended to be limiting.

As used herein, the terms "comprising" and "including" or grammatical variants thereof are to be taken as specifying inclusion of the stated features, integers, actions, ratios or components without precluding the addition of one or more additional features, integers, actions, ratios, components or groups thereof. This term is broader than, and includes the terms "consisting of" and "consisting essentially of" as defined by the Manual of Patent Examination Procedure of the United States Patent and Trademark Office.

The term "method" refers to manners, means, techniques and procedures for accomplishing a given task including, but not limited to, those manners, means, techniques and procedures either known to, or readily developed from known manners, means, techniques and procedures by practitioners of architecture and/or computer science.

Percentages (%) and/or ratios of sugars (saccharides) to a total mixture, as well as ratios of various sugars to one another (e.g. monosaccharides to disaccharides) are W/W (weight per weight) unless otherwise indicated. Percentages (%) and/or ratios of HCl are also expressed as W/W (weight per weight) unless otherwise indicate.

BRIEF DESCRIPTION OF THE DRAWINGS

In order to understand the invention and to see how it may be carried out in practice, embodiments will now be described, by way of non-limiting example only, with reference to the accompanying figures. In the figures, identical and similar structures, elements or parts thereof that appear in more than one figure are generally labeled with the same or similar references in the figures in which they appear. Dimensions of components and features shown in the figures are chosen primarily for convenience and clarity of presentation and are not necessarily to scale. The attached figures are:

FIGS. 2a and 2b are each simplified flow diagrams of methods according to exemplary embodiments of the invention;

FIG. 5 is a simplified flow diagram of a method according to an exemplary embodiment of the invention.

DETAILED DESCRIPTION OF EMBODIMENTS

Embodiments of the invention relate to sugar mixtures, their preparation and use. Specifically, some embodiments of the invention can be used as substrates for microbial fermentation. Optionally, the specific microorganisms employed are selected to utilize one or more sugars present in the mixture. Alternatively or additionally, some embodiments of the invention relate to adjusting one or more component ratios within a mixture to render the mixture more valuable for a specific downstream application.

The principles and operation of methods according to exemplary embodiments of the invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Overview of Exemplary System

Figure 1:
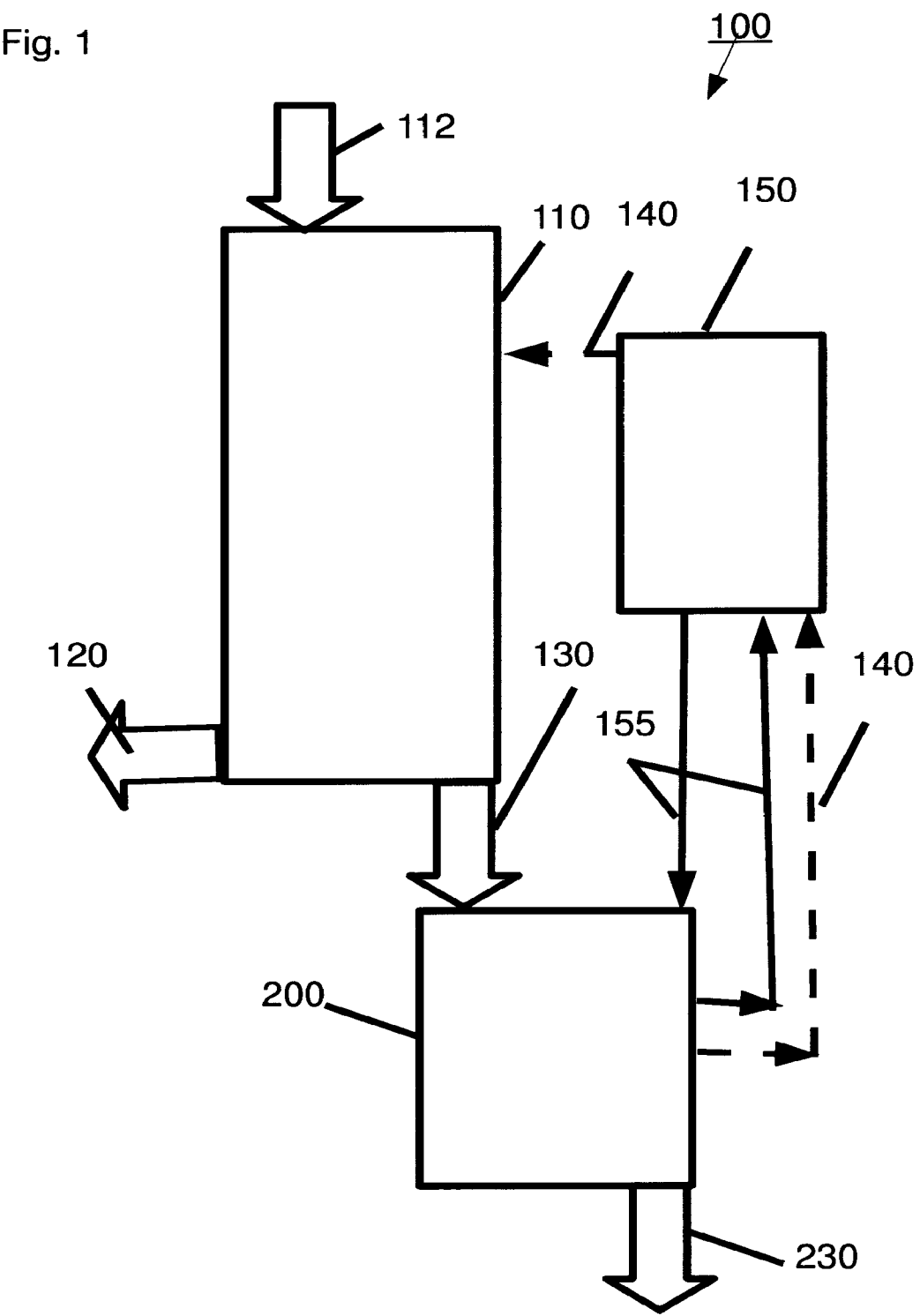
FIG. 1 is a schematic overview of a system illustrating the industrial context of some exemplary embodiments of the invention.

FIG. 1 is a simplified schematic diagram of a system for acid hydrolysis of a lignocellulosic substrate indicated generally as 100. Depicted system 100 includes a main hydrolysis reactor 110 adapted to receive a lignocellulosic substrate input 112. Optionally, substrate 112 is provided as wood chips, although any "woody material" as described in the background can be used instead of wood.

Substrate 112 is brought into contact with a concentrated HCl solution in reactor 110 and hemicellulose and/or cellulose in the substrate are hydrolyzed to produce a mixture of soluble sugars and residual lignin. These materials are collected separately as lignin stream 120 and sugar mixture 130, each of which contains a large amount of HCl.

Since the acid acts as a catalyst, it is not consumed in the process. In addition, residual acid content of the product and the co-products should be low in order to enable their use. Acid recovery from the hydrolyzate should be conducted under conditions minimizing thermal degradation.

Details of exemplary hydrolysis methods and systems are described in detail in co-pending U.S. provisional applications 61/483,777 and 61/487,319, each of which is fully incorporated herein by reference.

This application is primarily concerned with processing of sugar mixture 130. The processing includes removal of HCl and/or adjustment of the mixture to achieve one or more desired ratios of mixture components (e.g. disaccharides and/or monosaccharides). This processing is conducted in a sugar refining module, designated here generically as 200.

Optionally, additional sugar mixture is recovered from lignin stream 120 as described in co-pending U.S. provisional application U.S. 61/491,243 which is fully incorporated herein by reference. In some exemplary embodiments of the invention, this additional sugar mixture is routed to refining module 200. According to various exemplary embodiments of the invention this additional sugar mixture increase a total sugar yield and/or changes a composition of the mixture.

As will be explained in greater detail hereinbelow, refining module 200 employs a flow of organic solvent 155 (solid arrows) to extract HCl 140 (dashed arrows) from sugar mixture 130.

De-acidified sugars 230 are the primary product of refining module 200. Module 200 also produces a stream of HCl 140 mixed with solvent 155 (depicted as parallel dashed and solid arrows respectively for clarity) which is routed to a solvent/HCl recovery module 150. Recovery module 150 separates HCl 140 from solvent 155. In some exemplary embodiments of the invention, separation is by distillation. HCl 140 is recycled to hydrolysis reactor 110 and solvent 155 is recycled to refining module 200.

De-acidified sugars 230 can be used in various industrial conversion processes as described hereinbelow. Optionally, additional adjustments are made on de-acidified sugar 230 prior to these conversion processes as described below.

Exemplary Sugar Mixtures:

Some exemplary embodiments of the invention relate to sugar mixtures. In some exemplary embodiments of the invention, the mixtures can be characterized as: containing monosaccharides (e.g. hexoses such as glucose and/or galactose and/or mannose) and having an oligosaccharides to total saccharides ratio$\geq$0.06. Optionally, the mixture includes disaccharides and a disaccharides to total saccharides ratio$\geq$0.05. Optionally, the mixture includes a pentose (e.g. xylose and/or arabinose and/or ribose and/or lyxose) and a pentose to total saccharides ratio$\geq$0.05. In some exemplary embodiments of the invention, the mixture includes at least one alpha-bonded di-glucose (glucose bonded to glucose) and/or at least one beta-bonded di-glucose. Optionally, the mixture is characterized by a higher oligosaccharides to total saccharide ratio$\leq$0.2.

According to various exemplary embodiments of the invention the alpha-bonded di-glucose includes one or more of maltose, isomaltose and trehalose and the beta-bonded di-glucose includes one or more of gentiobiose, sophorose and cellobiose.

In some exemplary embodiments of the invention a ratio of at least one of said alpha-bonded di-glucose and said beta-bonded di-glucose relative to the total saccharide content is $\geq$0.01, optionally $\geq$0.03.

In some exemplary embodiments of the invention, the alpha-bonded di-glucose includes maltose and/or isomaltose and/or trehalose and/or kojibiose and/or nigerose. In some exemplary embodiments of the invention, the beta-bonded di-glucose includes gentiobiose and/or sophorose and/or cellobiose and/or laminaribiose and/or beta-trehalose.

In some exemplary embodiments of the invention, a proportion of the alpha-bonded di-glucose and/or the beta-bonded di-glucose is at least 0.01, optionally at least 0.02, optionally at least 0.03 relative to total saccharides.

According to some exemplary embodiments, the mixture includes multiple alpha-bonded di-glucoses and the combined proportion of these di-glucoses to total saccharides is at least 0.03. According to still another embodiment, the mixture includes multiple beta-bonded di-glucoses and the combined proportion to total saccharides of these beta-bonded di-glucoses is at least 0.03.

Exemplary Methods to Make Such Mixtures:

FIG. 2a is a simplified flow diagram depicting an exemplary method of making sugar mixtures as described above indicated generally as 202. According to the depicted method a lignocellulosic material is hydrolyzed 210 in HCl. In some exemplary embodiments of the invention, hydrolysis 210 employs a medium containing a ratio of HCl to (HCl+water)$\geq$0.37 by weight. Hydrolysis 210 yields a hydrolyzate 212 comprising total saccharides to (total saccharides+water)$\geq$0.20 by weight. The depicted method also includes de-acidifying 220 hydrolyzate 212 to form a de-acidified hydrolyzate 222 comprising: (i) a ratio of total saccharides to (total saccharides+water)$\geq$0.35 and; (ii) a ratio of total disaccharides to total saccharides$\geq$0.05. Optionally, an increase in saccharide concentration resulting from de-acidification 220 contributes to an increase in value.

Method 202 also includes adjusting 230 a composition of de-acidified hydrolyzate 222 to form a sugar mixture as described above. According to various exemplary embodiments of the invention adjusting 230 includes, but is not limited to, one or more of concentration, dilution, polishing, active carbon treatment, ion exchange chromatography and enzymatic oligomerization (e.g. to form dimers). Optionally, glycosyltransferases are employed.

Figure 2B:
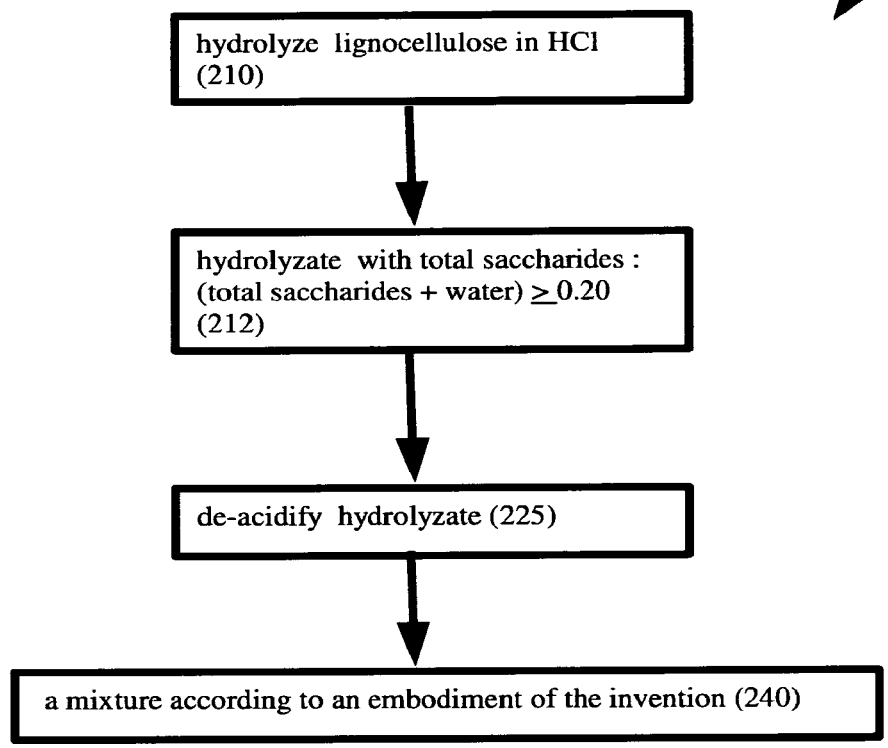

FIG. 2b is a simplified flow diagram depicting an additional exemplary method of making sugar mixtures as described above indicated generally as 204. Depicted method 204 includes hydrolyzing 210 to produce hydrolyzate 212 as described for method 202.

However, in depicted method 204 de-acidifying 225 of hydrolyzate 212 yields a de-acidified hydrolyzate comprising a mixture 240 according to an exemplary embodiment of the invention as described above.

With regards to methods 202 and/or 204 hydrolysis 210 is optionally conducted in a counter-current mode of operation and/or at a temperature of less than 25° C. In some exemplary embodiments of the invention, the lignocellulosic material hydrolyzed includes softwood, optionally pine.

According to various exemplary embodiments of methods 202 and/or 204 de-acidifying 220 or 225 includes selective extraction of HCl with an alcohol. In some exemplary embodiments of the invention, the alcohol has a water solubility of less than 15%, e.g. an alcohol with 5 to 8 carbon atoms. Optionally, some water is extracted with the HCl. Optionally; the de-acidifying is conducted at a temperature of less than 80° C.

Exemplary De-acidification Methods

Figure 3:
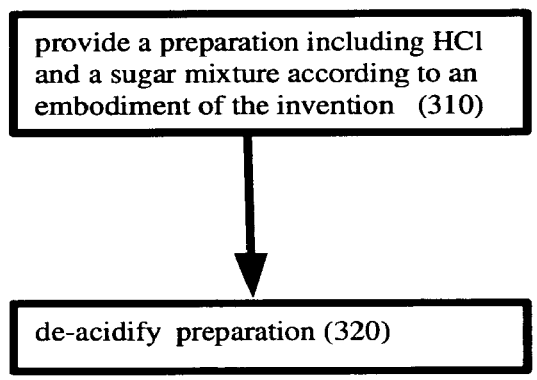
FIG. 3 is a simplified flow diagram of a method according to an exemplary embodiment of the invention.

FIG. 3 is a simplified flow diagram depicting an exemplary method of de-acidifying a sugar mixture as described above indicated generally as 300. According to the depicted method a preparation including HCl and a sugar mixture as described above is provided 310 and de-acidified 320. In some exemplary embodiments of the invention, de-acidifying 320 includes selective extraction of HCl with an alcohol. Optionally, hexanol or 2-ethyl-1-hexanol is employed for this extraction. Optionally, de-acidifying 320 is conducted at a temperature of less than 80° C., optionally less than 70° C. and optionally less than 60° C.

As used herein, "selective extraction" indicates that the HCl/carbohydrate ratio in the extract is greater than that ratio in the acidic hydrolyzate, optionally at least 5 fold greater, optionally at least 10 fold.

In some exemplary embodiments of the invention, de-acidifying is conducted according to methods disclosed in co-pending Israeli patent application IL 206,152 which is fully incorporated herein by reference.

Exemplary Downstream Processing of Sugar Mixtures

Figure 4A:
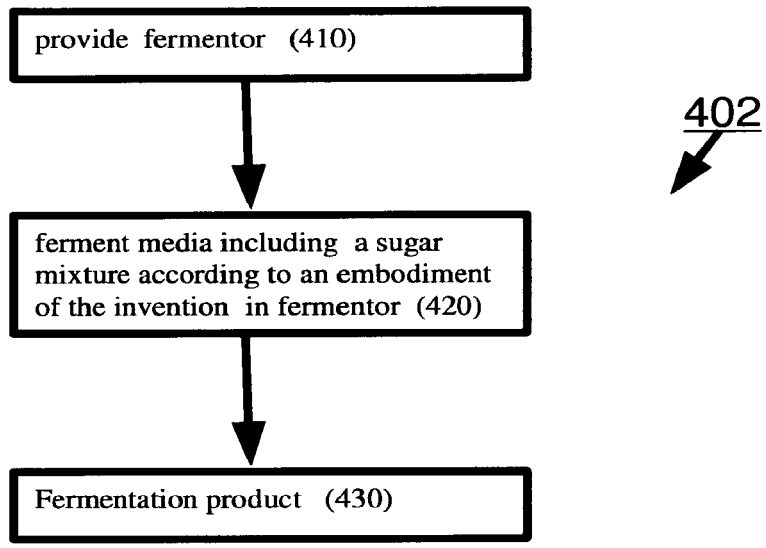
FIGS. 4a and 4b are each simplified flow diagrams of methods according to exemplary embodiments of the invention.

FIG. 4a is a simplified flow diagram depicting an exemplary method of producing a fermentation product from a sugar mixture as described above indicated generally as 402. According to the depicted method a fermentor is provided 410 and a media comprising a sugar mixture as described above is fermented 420 to produce a fermentation product 430.

Figure 4B:
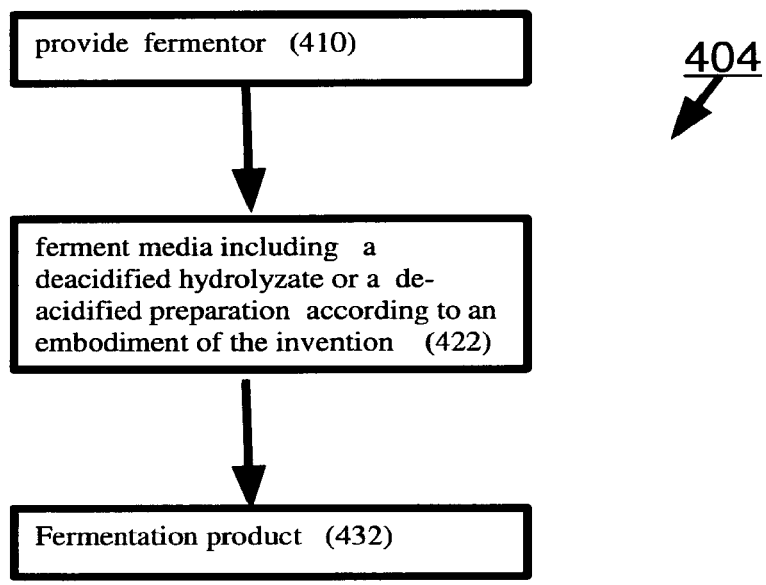

FIG. 4b is a simplified flow diagram depicting an exemplary method of producing a fermentation product from a sugar mixture as described above indicated generally as 404. According to the depicted method a fermentor is provided 410 and a media comprising a de-acidified hydrolyzate as described above or a de-acidified preparation as described above is fermented 422 to produce a fermentation product 432.

According to various exemplary embodiments of the invention fermentation product 430 and/or 432 includes an alcohol and/or a carboxylic acid and/or an amino acid and/or a monomer for the polymer industry and/or a protein.

One common fermentation product is ethanol, which may be useful, for example, as a fuel. For example, ethanol may be added to gasoline to produce "gasohol" as is commonly done in the United States, or used as a fuel itself as commonly done in Brazil.

Optionally, the fermentation product is a protein. In some exemplary embodiments of the invention, the protein is a heterologous protein and a disaccharide in the sugar mixture triggers an inducible regulatory element in a construct containing a sequence encoding the protein. In some exemplary embodiments of the invention, increasing an amount and/or ratio of a specific disaccharide in the sugar mixture contributes to an increased yield of fermentation product 430 and/or 432 per unit of sugar mixture in the media fermented 420 and/or 422.

Additional Methods Including Enzymatic Hydrolysis

FIG. 5 is a simplified flow diagram depicting an exemplary method for the production of a conversion product from a sugar mixture as described above indicated generally as 500. According to the depicted method, an acid hydrolyzate (as described above) including total saccharides to (total saccharides+water)≥0.20 by weight is de-acidified 510 to produce a sugar mixture 520 with a total saccharide to (total saccharide+water) ratio≥0.35 including monosaccharides and having a disaccharides to total saccharides ratio≥0.05. This mixture is an exemplary sugar mixture as described above.

Depicted exemplary method 500 also includes enzymatically hydrolyzing 522 a sugar mixture with an enzyme capable of catalyzing hydrolysis of alpha bonds in the mixture so that at least 10%, optionally at least 20%, optionally at least 30% of the disaccharides are converted to monosaccharides. The phrase "capable of catalyzing hydrolysis of alpha bonds" indicates any enzyme with at least 5% of the activity of alpha amylase with respect to alpha bonds. Optionally, at least 10% of the di-saccharides and higher saccharides are hydrolyzed to release additional monosaccharides. Optionally, higher saccharides release additional disaccharides.

In some exemplary embodiments of the invention, enzymatically hydrolyzing 522 is performed without having to concentrate dilute saccharide solutions, i.e. the enzymatic hydrolysis is performed at relatively high sugar concentration.

The depicted method also includes converting 530 at least a portion of the saccharides to a conversion product 540.

According to various exemplary embodiments of the invention converting includes fermentation and/or chemical conversion. Chemical conversion can be, for example, catalytic conversion.

According to various exemplary embodiments of the invention, converting and/or enzymatic hydrolysis may each be conducted in multiple stages in various sequences. Optionally, one or more converting processes are conducted between enzymatic hydrolysis stages. Alternatively or additionally, one or more enzymatic hydrolysis stages are conducted between converting processes.

In some exemplary embodiments of the invention, the sugar mixture comprises oligosaccharides with at least three sugar units.

In some exemplary embodiments of the invention, the initial acid hydrolyzate results from counter-current hydrolysis. Optionally, the acid hydrolysis is conducted at a temperature of less than 25° C.

In some exemplary embodiments of the invention, de-acidifying 510 includes extraction with an extractant including an alcohol. Optionally, de-acidifying 510 is conducted at a temperature of less than 80° C.

In some exemplary embodiments of the invention, enzymatically hydrolyzing 522 includes hydrolyzing beta bonds.

According to various exemplary embodiments of the invention enzymatically hydrolyzing 522 includes use of at least one of one enzyme belonging to EC 3.2.1 according to the Nomenclature Committee of the International Union of Biochemistry and Molecular Biology (NC-IUBMB) Enzyme Nomenclature Recommendations. This class of enzymes includes, but is not limited to, amylases cellulases, hemicellulases, transglucosidases, glucoamylases, alpha-glucosidases and pullulanases. Optionally, an alpha amylase and/or a beta amylase and/or a 1-4 alpha glucosidase are employed.

Optionally, one or more of these enzymes may be provided as part of an enzyme cocktail and/or a cellular extract including other undefined enzymes.

In some exemplary embodiments of the invention, an immobilized enzyme is used for enzymatically hydrolyzing 522. Optionally, immobilization contributes to hydrolysis of a greater number of bonds per enzyme molecule.

In some exemplary embodiments of the invention, at least a portion of converting 530 is conducted simultaneously with enzymatically hydrolyzing 522. Optionally, this concurrent processing prevents buildup of hydrolysis products which might adversely effect enzyme hydrolysis kinetics. For purposes of this specification and the accompanying claims the term "simultaneously" is used in its art accepted sense (i.e. simultaneous saccharification and fermentation).

Optionally, a ratio of total saccharides to (total saccharides+water)≥0.15, optionally ≥0.2 is maintained during enzymatic hydrolyzation.

According to some exemplary embodiments, enzymatically hydrolyzing 522 includes a single reaction, or temporally and/or distinct reactions, which reactions differ, in the composition of enzymes employed and/or in temperature and/or in pH.

In some exemplary embodiments of the invention, enzymatically hydrolyzing 522 includes fermentation with micro-organisms that produce the desired enzyme(s).

Alternatively or additionally, converting 530 comprises fermentation.

Optionally, sugar mixture 520 includes at least one pentose and a ratio between the at least one pentose and total saccharides is ≥0.05 by weight.

Exemplary De-acidification Processes

Figure 6:
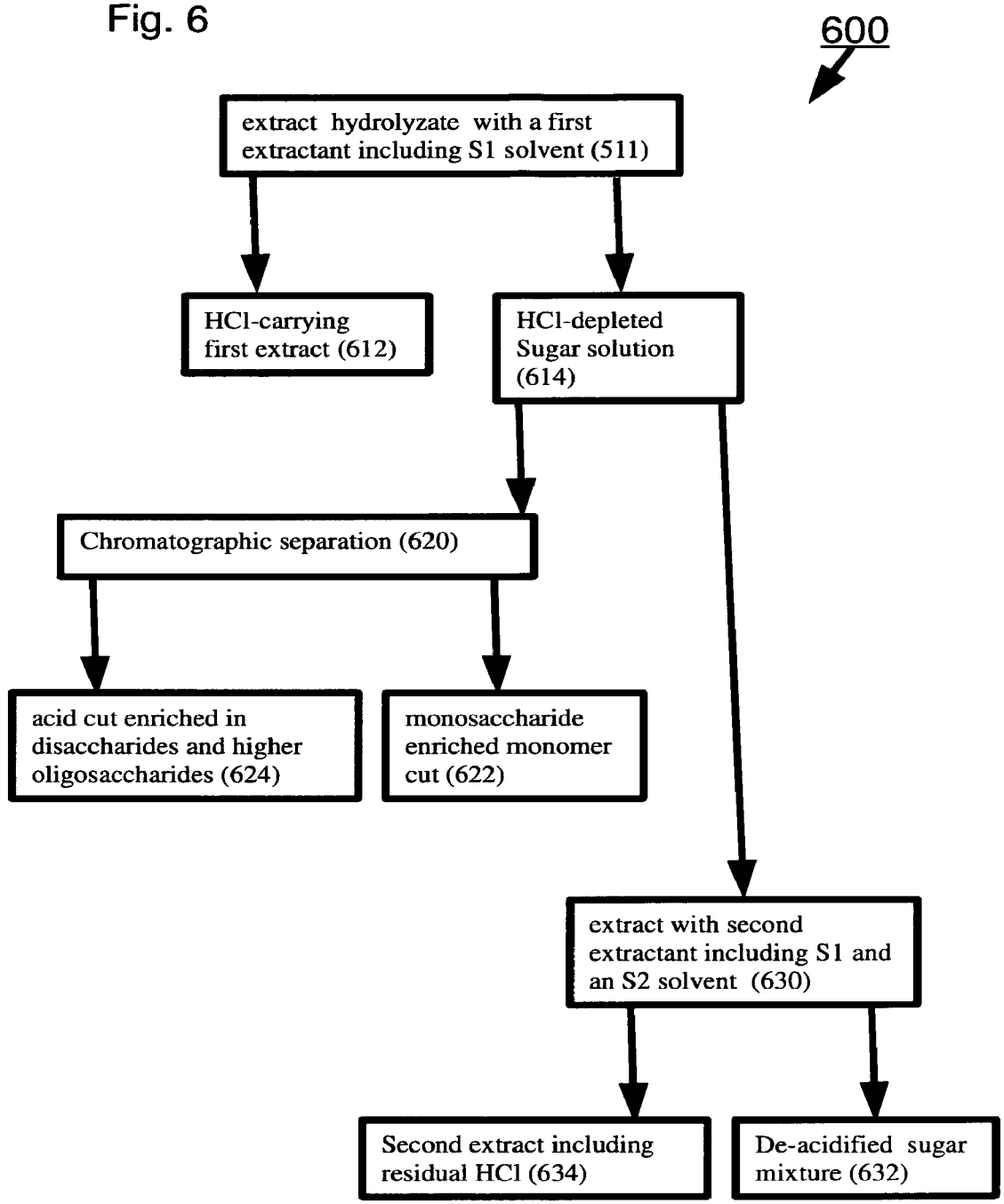
FIG. 6 is a simplified flow diagram of a portion of the method depicted in FIG. 5 in greater detail according to an exemplary embodiment of the invention.

FIG. 6 is a simplified flow diagram which illustrates some exemplary ways in which de-acidification 510 of FIG. 5 can be accomplished.

In the depicted exemplary embodiments of the invention, de-acidifying 510 includes extracting 511 the hydrolyzate with a first extractant including an S1 solvent to form an HCl-carrying first extract 612 and an HCl-depleted sugar solution 614. Optionally, the first extractant includes 70, 80, 90, 95 or substantially 100% of the S1 solvent. However, HCl may be present in sugar solution 614 at an unacceptable level. If that is the case, one or more additional separation strategies can optionally be employed.

According to various exemplary embodiments of the invention residual HCl in HCl-depleted sugar solution 614 is removed by chromatographic separation 620 and/or by a subsequent extraction 630 with a second extractant including S1 and a second solvent (S2).

Optionally, the total solvent concentration in the second extractant is 50 m 60, 70, 80, 90, 95 or substantially 100% or intermediate percentages.

In those exemplary embodiments of the invention which employ chromatographic separation 620 sugar solution 614 is separated into an HCl containing "acid cut" 624 which is enriched in disaccharides and higher saccharides relative to total saccharides and a "monomer cut" 622 enriched in monosaccharides relative to total saccharides. In some exemplary embodiments of the invention, acid cut 624 is subject to further treatment to separate saccharides from HCl and/or to adjust a ration of monosaccharides to total saccharides. Exemplary chromatographic separation techniques are disclosed in co-pending application IL 211093 which is fully incorporated herein by reference.

In those exemplary embodiments of the invention which employ a subsequent extraction 630, there is a selective transfer of HCl to the second extractant to form a second extract 634 and the de-acidified hydrolyzate 520 depicted here as de-acidified sugar mixture 632. Exemplary subsequent extraction techniques are disclosed in co-pending PCT application IL2011/000130 which is fully incorporated herein by reference.

Optionally, the S1 solvent employed in the initial extracting 511 and the subsequently extracting 630 includes a same solvent and/or a different solvent. S1 solvents employed in exemplary embodiments of the invention include, but are not limited to alcohols (e.g. hexanol and 2-ethyl hexanol), ketones and aldehydes having at least 5 carbon atoms and combinations thereof.

In some exemplary embodiments of the invention, the second extractant is characterized by a delta-P greater than the delta-P of the first extractant by at least 0.2 $MPa^{1/2}$ and/or a delta-H greater than the delta-H of the first extractant by at least 0.2 $MPa^{1/2}$.

According to various exemplary embodiments of the invention, S2 includes at least one member selected from the group consisting of $C_1$-$C_4$ mono- or poly-alcohols, aldehydes and ketones.

In some exemplary embodiments of the invention, a ratio of HCl to total saccharides in the de-acidified hydrolyzate 520 and/or 632 is ≤0.03 by weight.

Exemplary Industrial Contexts of Downstream Processing

Potential downstream applications of soluble carbohydrates include, but are not limited to, production of bio-fuels (e.g. ethanol, butanol or hydrocarbons), use in the food industry (e.g. fermentation to citric acid or xanthan gum and conversion of xylose to xylitol for use as an artificial sweetener) and industrially useful monomers.

As new processes are developed for the production of alternative fuels such as fatty acid esters and hydrocarbons (directly formed by fermentation or produced by conversion of fermentation products), the demand for soluble carbohydrates is expected to increase.

By way of example, sugar mixtures according to various exemplary embodiments of the invention are expected to be useful in fermentors which employ inducible promoters such as that described in U.S. Pat. No. 7,713,725 for example.

Alternatively or additionally, sugar mixtures according to various exemplary embodiments of the invention are expected to be useful in production of fatty ester compositions such as that described in, for example, US 2010/0071259.

Alternatively or additionally, sugar mixtures according to various exemplary embodiments of the invention are expected to be useful in extractive fermentation such as described in, for example, WO 2009/042950.

Alternatively or additionally, sugar mixtures according to various exemplary embodiments of the invention are expected to be useful in production of fatty acid derivatives as described in, for example, WO 2008/119082.

Alternatively or additionally, sugar mixtures according to various exemplary embodiments of the invention are expected to be useful in production of peptides as described in, for example, U.S. Pat. No. 7,595,173.

In summary, direct downstream products of sugar mixtures according to various exemplary embodiments of the invention resulting from fermentation and/or conversion (e.g. alcohols, lactic acid, acrylic acid and antimicrobial peptide) are expected to give rise to a wide variety of products resulting from further processing of these conversion products. Such products include, but are not limited to, automobile fuel (e.g. for automobiles and/or airplanes), diapers, plastic consumer products and paint.

Exemplary Consumer Products

Some exemplary embodiments of the invention, relate to consumer products and their manufacture or preparation.

In some exemplary embodiments of the invention, a sugar mixture according to one exemplary embodiment of the invention is converted to a fermentation product according to one or more additional embodiments of the invention. Optionally, the fermentation product includes at least one member selected from the group consisting of alcohols, carboxylic acids, amino acids, monomers for the polymer industry and proteins.

In some exemplary embodiments of the invention, the fermentation product is processed to produce a consumer product. Exemplary consumer products include but are not limited to detergent, polyethylene-based products, polypropylene-based products, polyolefin-based products, polylactic acid (polylactide)-based products, polyhydroxyalkanoate-based products and polyacrylic-based products.

In some exemplary embodiments of the invention, the detergent includes a sugar-based surfactant and/or a fatty acid-based surfactant and/or a fatty alcohol-based surfactant and/or a cell-culture derived enzyme.

In some exemplary embodiments of the invention, the polyacrylic-based product includes a plastic and/or a floor polish and/or a carpet and/or a paint and/or a coating and/or an adhesive and/or a dispersion and/or a flocculants and/or an elastomer and/or acrylic glass and/or an absorbent articles (e.g. incontinence pads, sanitary napkins, feminine hygene products, and diapers).

Polyolefin-based products may be, for example, milk jugs, detergent bottles, margarine tubs, garbage containers, water pipes, absorbent articles, diapers, non woven fabrics (e.g. pre-moistened towelettes), HDPE toys and HDPE detergent packagings.

In some exemplary embodiments of the invention, a polypropylene based product is provided as an absorbent articles, optionally a diaper.

In other exemplary embodiments of the invention, a polypropylene based product is provided as anon woven fabric item, optionally a pre-moistened towellette.

Polylactic acid based products may be, for example, packaging of agriculture or dairy products, plastic bottles, biodegradable products and disposables.

Polyhydroxyalkanoate based products may be, for example, packaging of agriculture products, plastic bottles, coated papers, molded or extruded articles, feminine hygiene products, tampon applicators, absorbent articles, disposable nonwovens and wipes, medical surgical garments, adhesives, elastometers, films, coatings, aqueous dispersants, fibers, intermediates of pharmaceuticals and binders.

Optionally, the fermentation product includes at least one member of the group consisting of ethanol, butanol, isobutanol, a fatty acid, a fatty acid ester, a fatty alcohol and biodiesel. In some exemplary embodiments of the invention, the fermentation product is processed to produce an isobutene condensation product and/or a jet fuel and/or gasoline and/or gasohol and/or diesel fuel and/or drop-in fuel and/or a diesel fuel additive and/or a precursor thereof. According to various exemplary embodiments of the invention gasahol is ethanol-enriched gasoline or butanol-enriched gasoline.

Optionally, the product is a diesel fuel. Optionally, the product is gasoline. Optionally, the product is jet fuel. Optionally, the product is a drop-in fuel.

According to various exemplary embodiments of the invention a consumer product, a precursor of a consumer product, or an ingredient of a consumer product is produced from a fermentation product. Optionally, the consumer product, precursor of a consumer product, or ingredient of a consumer product includes at least one fermentation product as described hereinabove including one or more of carboxylic and fatty acids, dicarboxylic acids, hydroxylcarboxylic acids, hydroxyl di-carboxylic acids, hydroxyl-fatty acids, methylglyoxal, mono-, di-, or poly-alcohols, alkanes, alkenes, aromatics, aldehydes, ketones, esters, biopolymers, proteins, peptides, amino acids, vitamins, antibiotics, and pharmaceuticals. In some exemplary embodiments of the invention, the product is ethanol-enriched gasoline, jet fuel, or biodiesel.

In some exemplary embodiments of the invention, a consumer product, or an ingredient of a consumer product according as described above has a ratio of carbon-14 to carbon-12 of $1.8 \times 10^{-13}$, optionally $2.0 \times 10^{-13}$ or greater.

In some exemplary embodiments of the invention, the consumer product includes an ingredient as described above and an additional ingredient produced from a raw material other than lignocellulosic material. Optionally, the ingredient and the additional ingredient are essentially of the same chemical composition.

Some exemplary embodiments of the invention relate to a consumable product as described above including a marker molecule at a concentration of at least 100 ppb. The marker molecule optionally includes one or more of furfural, hydroxy-methyl furfural, products of furfural or hydroxy-mathylfurfural condensation, color compounds derived from sugar caramelization, levulinic acid, acetic acid, methanol, galcturonic acid, and glycerol.

It is expected that during the life of this patent many EC 3.2.1 enzymes will be characterized and the scope of the invention is intended to include all such new enzymes a priori.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

Specifically, a variety of numerical indicators have been utilized. It should be understood that these numerical indicators could vary even further based upon a variety of engineering principles, materials, intended use and designs incorporated into the invention. Additionally, components and/or actions ascribed to exemplary embodiments of the invention and depicted as a single unit may be divided into subunits. Conversely, components and/or actions ascribed to exemplary embodiments of the invention and depicted as sub-units/individual actions may be combined into a single unit/action with the described/depicted function.

Alternatively, or additionally, features used to describe a method can be used to characterize an apparatus and features used to describe an apparatus can be used to characterize a method.

It should be further understood that the individual features described hereinabove can be combined in all possible combinations and sub-combinations to produce additional embodiments of the invention. The examples given above are exemplary in nature and are not intended to limit the scope of the invention which is defined solely by the following claims. Specifically, the invention has been described in the context of ethanol production but is widely applicable to any fermentation or conversion process.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

The terms "include", and "have" and their conjugates as used herein mean "including but not necessarily limited to".

Additional objects, advantages, and novel features of various embodiments of the invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Materials and Methods

The following materials and methods are used in performance of experiments described in examples hereinbelow:
Enzymes: Some enzymes (Examples 1-3) were from Novozymes (Novozymes A/S; Denmark):
Spyrizyme Fuel HS: Glucoamylase with α 1-4 and 1-6 activity; 1425 AGU/g declared activity; Light to dark-brown liquid.
Liquozyme SC DS: α-Amylase with 1-4 activity; 240 KNU-S/g declared activity; Amber liquid.
Manufaturer's instructions are:
Spyrizyme Fuel HS: 0.025-0.035% (w/w) grain "as is"
Liquozyme SC DS: n.a.
Cellic CTec: 1.5%, 3.0%, and 15% w/w (g enzyme/g cellulose).
Cellic HTech: 0.1-0.5% (w/w TS).
Additional enzymes were obtained from Genencor (Danisco; Genencor, Beloit Wis., USA):
Spezyme Alpha: <1% α-Amylase activity 13,775 (Alpha Amylase Units)/g (min.), thermostable, dark-brown liquid, optimal pH 5.5-6.5.
Transglucosidase L-2000: 1-5% Active enzyme, having α 1-4 activity, yellow-brown liquid, optimal pH 4.5-5.5.
The recommended usages of enzymes (A. Kelley, Genencor) are:
Spezyme Alpha: 0.025%
Transglucosidase L-2000: 0.01%
Accelerase BG: 8%
Accelerase DUET: 8%
Hydrolyzates: Hydrolyzates from Pinewood were employed as a substrate for enzymatic analyses. The hydrolyzates were adjusted to contain a desired % TS (Total Suaccharides). All experiments were conducted at pH 4.0-5.1 at various temperatures from 50 to 85° C. Loading doses of the enzymes were also varied.

In all of the enzymatic hydrolysis experiments time 0 (hrs.) refers to the blank (without enzyme).

Hydrolyzates from pinewood, sugarcane bagasse and eucalyptus wood were also subject to detailed analyses of monosaccharide and disaccharide concentrations.

Control of reaction conditions: The hydrolyzate was diluted with deionized (DI) water and buffer to a desired TS % and pH. The enzyme solution was added and the flask was kept at a selected temperature with stirring throughout incubation. Samples were withdrawn according to an experimental schedule and the enzyme was denatured by heating and filtered out.

Saccharide analyses:
Saccharide composition of the samples was analyzed by HPLC using a Varian Prostar® and a Rezex RSO-Oligosaccharide Ag+, 10×200 mm column and pre-column in the following conditions:
Column Temp.: 80° C., Mobile Phase: Water (HPLC grade), Flow Rate: 0.3 mL/min, Injection: 5-10 μL (depending on sugars conc.), Detector: RI, Detector Temp.: 40° C.

The DP groups HPLC results are given in area %, the x-axis in the graphs represents time (hrs.) and the y-axis area %.

DP stands for degree of polymerization, so that DP1 refers to all mono-saccharides, DP2 are all di-saccharides, DP3 are all tri-saccharides and DP>3 refers to oligosaccharides containing more than three sugar units (DP groups given as % area).

Example 1

Exemplary Enzymatic Hydrolysis of a De-acidified Hydrolyzate with 30% TS Using Spirizyme In order to examine the influence of enzyme amounts on total monosaccharide yield, enzyme amount was titrated and efficiency of enzymatic hydrolysis was measured.

In a first series of enzymatic hydrolysis experiment Spyrizyme Fuel HS and Liquozyme SC DS were employed.

A pinewood hydrolyzate with 30% TS at pH 4.9 was hydrolyzed with 3 mg enzyme solution/1 gr 100% sugar at a temperature of 62° C. with stirring (enzyme was 0.3%). Results are summarized in Table 1.

TABLE 1

Spirizyme Fuel HS (3 mg enzyme solution/1 gr 100% sugar)

| Time (Hr) | DP1 (% area) | DP2 (% area) | DP3 (% area) | DP > 3 (% area) |
| --- | --- | --- | --- | --- |
| 0 | 45.7 | 31.8 | 13.7 | 8.8 |
| 2.5 | 51.2 | 31.5 | 12.2 | 5.0 |
| 4.0 | 51.4 | 31.5 | 11.8 | 5.3 |
| 24 | 56.2 | 28.2 | 11.0 | 4.6 |

In order to assess the impact of increasing the amount of enzyme, 33 mg enzyme solution/1 gr 100% sugar were employed. Results are summarized in Table 2.

TABLE 2

Spirizyme Fuel HS (33 mg enzyme solution/1 gr 100% sugar)

| Time (hr) | DP1 (% area) | DP2 (% area) | DP3 (% area) | DP > 3 (% area) |
| --- | --- | --- | --- | --- |
| 0 | 45.7 | 31.8 | 13.7 | 8.8 |
| 2.5 | 64.0 | 26.8 | 7.0 | 2.3 |
| 4.0 | 65.1 | 26.2 | 6.4 | 2.3 |

Results summarized in Tables 1 and 2 demonstrate a trend towards increased proportion of DP1 and DP2 saccharides at the expense of DP3 and DP>3 saccharides. This trend increased as a function of time.

In order to assess the impact of increasing the amount of enzyme even further, 65.6 mg enzyme solution/1 gr 100% sugar were employed. Results are summarized in Table 3.

TABLE 3

Spirizyme Fuel HS (65.6 mg enzyme solution/1 gr 100% sugar)

| Time (hr) | DP1 (% area) | DP2 (% area) | DP3 (% area) | DP > 3 (% area) |
| --- | --- | --- | --- | --- |
| 0 | 45.7 | 31.8 | 13.7 | 8.8 |
| 2.5 | 68.2 | 26.8 | 7.0 | 2.3 |
| 4.0 | 68.1 | 26.2 | 6.4 | 2.3 |

Results presented in Table 3 indicate that it is possible to increase the yield of monosaccharides even further.

In order to assess the impact of increasing the amount of enzyme even further, 282.6 mg enzyme solution/1 gr 100% sugar were employed. Results are summarized in Table 4.

TABLE 4

Spirizyme Fuel HS (282.6 mg enzyme solution/1 gr 100% sugar)

| Time (hr) | DP1 (% area) | DP2 (% area) | DP3 (% area) | DP > 3 (% area) |
|---|---|---|---|---|
| 0 | 45.7 | 31.8 | 13.7 | 8.8 |
| 2.5 | 70.6 | 22.4 | 5.6 | 1.5 |
| 4.0 | 71.1 | 21.6 | 5.5 | 1.8 |

Results summarized in Tables 1 to 4 indicate that enzymes capable of hydrolyzing alpha bonds can be employed to increase monosaccharide concentrations in acid hydrolyzates of cellulose. The enzyme dose of 282.6 mg gave the highest yield of mono-saccharides.

However, other conditions may contribute to enzymatic hydrolysis results. Exemplary other conditions include, but are not limited to, reaction temperature, exact nature of the sugars in the hydrolyzate in terms of both bond type and oligomer length distribution.

Example 2

Influence of % TS on Enzymatic Hydrolysis of a De-acidified Hydrolyzate Using Spirizyme In order to examine the influence of % TS in the substrate on total monosaccharide yield, enzyme amount was titrated again against a hydrolyzate similar to that used in Example 1, but with decreasing amounts of % TS and efficiency of enzymatic hydrolysis was measured.

A pinewood hydrolyzate with 15% TS at pH 5.1 was hydrolyzed with 72.8 mg enzyme solution/1 gr 100% sugar at a temperature of 60° C. with stirring (enzyme ~243 of manufacturer's recommendation). Results are summarized in Table 5. This experiment confirms results presented in Table 2 of Example 1 and suggests that more dilute sugar solutions are more amenable to enzymatic hydrolysis.

TABLE 5

Spirizyme Fuel HS (72.8 mg enzyme solution/1 gr 100% sugar)

| Time (hr) | DP1 (% area) | DP2 (% area) | DP3 (% area) | DP > 3 (% area) |
|---|---|---|---|---|
| 0 | 45.7 | 31.8 | 13.7 | 8.8 |
| 2.5 | 71.3 | 20.6 | 6.1 | 2.1 |
| 4.0 | 71.8 | 21.0 | 4.9 | 2.3 |
| 5.8 | 71.8 | 20.2 | 5.7 | 2.3 |
| 24 | 71.1 | 24.3 | 3.4 | 1.2 |
| 50 | 76.0 | 17.9 | 4.7 | 1.4 |

A pinewood hydrolyzate with 5% TS at pH 5.0 was hydrolyzed with 67 mg enzyme solution/1 gr 100% sugar at a temperature of 62° C. with stirring (enzyme ~233 times manufacturer's recommendation). Results are summarized in Table 6. This experiment confirms results presented in Table 2 of Example 1 and suggests that more dilute sugar solutions are more amenable to enzymatic hydrolysis.

TABLE 6

Spirizyme Fuel HS (67 mg enzyme solution/1 gr 100% sugar)

| Time (hr) | DP1 (% area) | DP2 (% area) | DP3 (% area) | DP > 3 (% area) |
|---|---|---|---|---|
| 0 | 49.8 | 31.3 | 12.9 | 6.1 |
| 2.5 | 72.0 | 20.4 | 5.4 | 2.2 |
| 24 | 75.4 | 17.8 | 5.0 | 1.8 |
| 50 | 74.7 | 19.7 | 4.3 | 1.3 |
| 72 | 77.8 | 16.2 | 4.8 | 1.2 |
| 96 | 77.1 | 15.7 | 4.9 | 2.3 |

Results presented in table 6 confirm that enzymes capable of hydrolyzing alpha bonds can be employed to increase monosaccharide concentrations in acid hydrolyzates of cellulose.

Comparison of results presented in table 6 with those presented in Tables 2 and 5 suggests that dilution of sugar solutions prior to enzymatic hydrolysis contributes to an increase in monosaccharide yield.

Again, the exact nature of the sugars in the hydrolyzate in terms of both bond type and oligomer length distribution may influence the total yield of monosaccharides.

Example 3

Enzymatic Hydrolysis of a De-acidified Hydrolyzate with 30% TS Using Liquozyme SC DS In order to determine whether the results presented above were enzyme specific an additional experiment was conducted on a 30% TS hydrolyzate using Liquozyme. A pinewood hydrolyzate with 30% TS at pH 6.0 was hydrolyzed with 282.6 mg enzyme solution/1 gr 100% sugar at a temperature of 85° C. with stirring (enzyme ~942 times manufacturer's recommendation for Spirizyme). Results are summarized in Table 7. This experiment confirms results presented in Table 2 of Example 1 and suggests that more dilute sugar solutions are more amenable to enzymatic hydrolysis.

TABLE 7

Liquozyme SC DS (282.6 mg enzyme solution/1 gr 100% sugar)

| Time (hr) | DP1 (% area) | DP2 (% area) | DP3 (% area) | DP > 3 (% area) |
|---|---|---|---|---|
| 0 | 45.7 | 31.8 | 13.7 | 8.8 |
| 4.0 | 59.8 | 27.1 | 8.4 | 4.5 |

Results presented in table 7 indicate that the ability of enzymes capable of hydrolyzing alpha bonds to increase monosaccharide concentrations in acid hydrolyzates of cellulose is not specific to Spirizyme Fuel HS.

These results also suggest that Liquozyme SC DS provides a higher yield of mono-saccharides than Spirizyme Fuel HS at 282.6 mg enzyme solution/1 gr 100% sugar (see Table 4 for comparison). However, the desirability of one enzyme over another may also be influence by other considerations including, but not limited to, availability, purity, bond specificity and price.

Example 4

Enzymatic Hydrolysis of a De-acidified Sugarcane Bagasse Hydrolyzate with Various Enzymes In order to examine the possibility of applying enzymatic hydrolysis to hydrolyzates from non-wood substrates, a series of experiments was conducted on hydrolyzates prepared from sugar cane bagasse. The hydrolyzates used contained different TS (5%, 20%), the experiments were conducted at pH 4.5-5.1, and at various temperatures (50° C. and 60° C.). The loading doses of the enzymes were also varied.

A first experiment was conducted using Spezyme Alpha at a concentration of 34.2 mg enzyme solution/1 gr 100% sugar, at a temperature of 60° C. and at pH 5.1, applied to a bagasse hydrolyzate with 20% TS. Results are summarized in Table 8.

TABLE 8

Spezyme Alpha applied to Baggase hydrolyzate TS 20% (34.2 mg enzyme solution; about 137 times manufacturer's recommendation)

| Time (hr) | DP1 (% area) | DP2 (% area) | DP3 (% area) | DP > 3 (% area) |
|---|---|---|---|---|
| 0 | 52.0 | 35.4 | 10.6 | 1.9 |
| 2.5 | 52.0 | 34.9 | 10.8 | 2.3 |
| 4.0 | 53.6 | 34.2 | 10.1 | 2.1 |
| 24 | 52.4 | 35.1 | 10.3 | 2.2 |
| 50 | 51.7 | 35.1 | 10.9 | 2.3 |

An additional experiment was conducted using Transglucosidase L-2000 at a concentration of 14.8 mg enzyme/1 gr 100% sugar at a temperature of 60° C. at pH 5.0 applied to a bagasse hydrolyzate with 20% TS. Results are summarized in Table 9.

TABLE 9

Transglucosidase L-2000 applied to Baggase hydrolyzate TS 20% (14.8 mg enzyme; about 148 times manufacturer's recommendation)

| Time (hr) | DP1 (% area) | DP2 (% area) | DP3 (% area) | DP > 3 (% area) |
|---|---|---|---|---|
| 0 | 52.0 | 35.4 | 10.6 | 1.9 |
| 2.5 | 57.9 | 29.7 | 10.0 | 2.4 |
| 4.0 | 62.0 | 26.8 | 9.1 | 2.2 |
| 24 | 62.7 | 27.0 | 8.5 | 1.8 |
| 50 | 62.2 | 27.1 | 8.7 | 2.0 |

Results summarized in Tables 8 and 9 indicate that Transglucosidase L-2000 provides an increase in monosaccharides in the bagasse hydrolyzate while Spezyme Alpha does not provide such an increase.

The results from Transglucosidase L-2000 (Table 9) confirm that enzymes capable of hydrolyzing alpha bonds can be used to increase the yield of monosaccharides.

The negative results from Spezyme Alpha presented in table 8 suggest that there may be inhibitors present in the hydrolyzate. At this stage it is not clear whether these inhibitors are specific to the substrate subject to the initial acid hydrolysis (e.g. sugar cane bagasse as opposed to pine wood) or are specific to the enzyme.

Example 5

Saccharide Composition of Hydrolyzates of a First Pine Wood

In order to obtain a sugar mixture, dry first pinewood was introduced into a six stage hydrolysis reactor series in a counter-current operation as described in co-pending U.S. provisional application 61/48377 filed May 9, 2011 and entitled "Hydrolysis systems and methods". This application is fully incorporated herein by reference.

Briefly, an aqueous solution of 42% HCl was introduced continually at a temperature of 10-15° C. for 24 hours. The hydrolyzate was collected, HCl was removed by extraction and the deacidified hydrolyzate was concentrated to give a sugar composition. The composition was analyzed by HPLC, the sample's total sugars was 74.3%. Analysis results of monosaccharides and disaccharides are summarized in Tables 10 and 11 respectively. The results are calculated as % from sample's refractive total saccharides (%/RTS).

TABLE 10

Monosaccharides in hydrolyzate of the first pine wood

| Rhamnose | Arabinose | Galactose | Glucose | Xylose | Mannose | Sum |
|---|---|---|---|---|---|---|
| 0.1 | 1.6 | 2.7 | 27.7 | 7.0 | 7.4 | 46.5 |

TABLE 11

Disaccharides in hydrolyzate of the first pine wood

| Trehalose | Isomaltose | Gentiobiose | Cellobiose | Nigerose | Sophorose | Other DP2 | Sum |
|---|---|---|---|---|---|---|---|
| 1.4 | 4.8 | 1.0 | 0.7 | 0.4 | 0.2 | 14.5 | 22.9 |

Results summarized in table 10 illustrate the presence of pentoses such as Arabinose and Xylose and Rhamnose (de-oxy pentose). Since these pentoses are prone to degradation under harsh acidic conditions, their presence suggests that the counter current design of the hydrolysis reactor contributes to a "pentose sparing" effect.

Results summarized in Table 11 illustrate the presence of alpha-bonded di-glucose such as Trehalose and Isomaltose, as well as the presence of beta-bonded di-glucose such as Gentiobiose and Sophorose.

Example 6

Saccharide Composition of Hydrolyzates of a Second Pine Wood

Similarly, a second pine wood was hydrolyzed, deacidified and concentrated to 77% TS.

Analysis results of monosaccharides and disaccharides are presented in Tables 12 and 13 respectively. The results are calculated as % from sample's refractive total saccharides (%/RTS).

TABLE 12 monosaccharides in hydrolyzate of the second wood

| Arabinose | Galactose | Glucose | Xylose | Mannose | Sum |
|---|---|---|---|---|---|
| 0.3 | 0.8 | 36 | 8 | 1.0 | 46 |

TABLE 13

| results of disaccharides in hydrolyzate of the second wood | | | | | | | |
|---|---|---|---|---|---|---|---|
| Trehalose | Isomaltose | Gentiobiose | Cellobiose | Nigerose | Maltose | Other DP2 | Sum |
| 1.1 | 6.6 | 2.1 | 2.1 | 0.4 | 0.4 | 28 | 41 |

The second pine wood also contained 16.7% higher oligosaccharides.

Results summarized in tables 12 and 13 confirm the presence of pentose, of alpha-bonded di-glucose and of beta-bonded di-glucose. There are differences in the saccharide profiles of hydrolyzates of the two pine sources.

Example 7

Saccharide Composition of Hydrolyzate Prepared from Non-Pine Wood Substrates

In order to examine the effect of substrate composition on hydrolyzate composition in terms of specific sugars, deacidified hydrolyzates prepared from sugar cane bagasse and Eucalyptus wood were analyzed as in Example 6.

Analysis results of monosaccharides and disaccharides from the sugar cane bagasse hydrolyzate are presented in Tables 14 and 15 respectively. The results are calculated as % from sample's refractive total saccharides (%/RTS).

TABLE 14

| results of monosaccharides in hydrolyzate of sugar cane bagasse | | | | | | |
|---|---|---|---|---|---|---|
| Arabinose | Galactose | Glucose | Xylose | Mannose | Fructose | Sum |
| 2.2 | 7.2 | 48.7 | 4.9 | 4.8 | 2.4 | 70.2 |

TABLE 15

| results of disaccharides in hydrolyzate of sugar cane bagasse | | | | |
|---|---|---|---|---|
| Isomaltose | Gentiobiose | Maltose | Other DP2 | Sum |
| 4.5 | 0.6 | 2.9 | 27 | 35 |

Analysis results of monosaccharides and disaccharides from the eucalyptus wood hydrolyzate are presented in Tables 16 and 17 respectively. The results are calculated as % from sample's refractive total saccharides (%/RTS).

TABLE 16

| results of monosaccharides in hydrolyzate of Eucalyptus wood | | | | | | |
|---|---|---|---|---|---|---|
| Arabinose | Galactose | Glucose | Xylose | Mannose | Fructose | Sum |
| 2.6 | 7.24 | 46.1 | 8.27 | 5.83 | 3.38 | 73.42 |

TABLE 17

| results of disaccharides in hydrolyzate of sugar Eucalyptus wood | | | | |
|---|---|---|---|---|
| Isomaltose | Cellobiose | Maltose | Other DP2 | Sum |
| 7.1 | 1.85 | 2.16 | 11.11 | 22 |

Results presented in tables 14 to 17, taken together with results presented in tables 10 to 13 suggest that the substrate used for the initial acid hydrolysis can influence the saccharide profile of the resultant de-acidified hydrolyzate.

The invention claimed is:

1. A method comprising:
    (a) hydrolyzing a lignocellulosic material in a medium containing a mineral acid to form a hydrolyzate;
    (b) de-acidifying the hydrolyzate to form a de-acidified hydrolyzate comprising:
        monosaccharides;
        a ratio of higher oligosaccharides to total saccharides of ≤0.2 weight/weight;
        a ratio of pentose to total saccharides of ≥0.05 weight/weight;
        at least one alpha-bonded di-glucose;
        at least one beta-bonded di-glucose; and
        a ratio of mineral acid to total saccharides of ≤0.03 weight/weight.

2. The method of claim 1, wherein the hydrolyzing is conducted in a counter-current mode of operation.

3. The method of claim 1, wherein the hydrolyzing is conducted at a temperature of less than 50° C.

4. The method of claim 1, wherein the ratio of the mineral acid to total mineral acid and water in the medium is ≥0.37 by weight.

5. The method of claim 1, wherein the mineral acid is HCl.

6. The method of claim 1, wherein the de-acidifying is conducted at a temperature of less than 80° C.

7. The method of claim 1, wherein the de-acidifying comprises:
    (i) extracting the hydrolyzate with a first extractant comprising an S1 solvent to form a mineral acid-carrying first extract and a mineral acid-depleted sugar solution, and
    (ii) removing residual mineral acid in the mineral acid-depleted sugar solution by at least one of:
        (ii-a) chromatographic separation, and
        (ii-b) extraction with a second extractant comprising the S1 solvent and an S2 solvent;
    wherein the S1 solvent is an organic solvent with a water solubility of less than 15% and is characterized by one or more of a polarity related component of Hoy's cohesion parameter (delta-P) between 5 and 10 $MPa^{1/2}$ and a hydrogen bonding related component of Hoy's cohesion parameter (delta-H) between 5 and 20 $MPa^{1/2}$; and
    wherein the S2 solvent is an organic solvent with a water solubility of at least 30% and is characterized by one or more of a delta-P greater than 8 $MPa^{1/2}$ and a delta-H greater than 12 $MPa^{1/2}$.

8. The method of claim 7, wherein the S1 solvent is selected from an alcohol, a ketone, and an aldehyde having at least 5 carbon atoms.

9. The method of claim 8, wherein the S1 solvent is selected from hexanol and 2-ethyl hexanol.

10. The method of claim 7, wherein the S2 solvent is selected from a $C_1$-$C_4$ mono-alcohol, a $C_1$-$C_4$ poly-alcohol, an aldehyde, and a ketone.

11. The method of claim 7, comprising removing residual mineral acid in the mineral acid-depleted sugar solution by (ii-a) chromatographic separation.

12. The method of claim 1, wherein the de-acidifying comprises chromatographic separation.

13. The method of claim 1, wherein the hydrolyzing of (a) forms the hydrolyzate and residual lignin, wherein the method further comprises:
   (a-2) separating the hydrolyzate from the residual lignin before the de-acidifying of (b).

14. The method of claim 1, further comprising:
   (c) converting the saccharides in the de-acidified hydrolyzate to a conversion product.

15. The method of claim 14, wherein the conversion product is selected from a detergent, polyethylene-based products, polypropylene-based products, polyolefin-based products, polylactic acid-based products, polyhydroxyalkanoate-based products and polyacrylic-based products.

16. The method of claim 14, wherein the conversion product is selected from carboxylic acids, fatty acids, dicarboxylic acids, hydroxycarboxylic acids, hydroxy di-carboxylic acids, hydroxy-fatty acids, methylglyoxal, mono-, di-, or poly-alcohols, alkanes, alkenes, aromatics, aldehydes, ketones, esters, biopolymers, proteins, peptides, amino acids, vitamins, antibiotics, and pharmaceuticals.

17. The method of claim 14, wherein the conversion product is selected from ethanol, butanol, isobutanol, a fatty acid, a fatty acid ester, a fatty alcohol and biodiesel.

18. The method of claim 1, wherein the ratio of total saccharides to total saccharides and water in the hydrolyzate is $\geq 0.20$ by weight.

19. The method of claim 1, wherein the ratio of at least one of the alpha-bonded di-glucose and the beta-bonded di-glucose to total saccharides in the de-acidified hydrolyzate is $\geq 0.01$ weight/weight.

* * * * *

UNITED STATES PATENT AND TRADEMARK OFFICE
CERTIFICATE OF CORRECTION

PATENT NO. : 10,752,878 B2  
APPLICATION NO. : 15/933210  
DATED : August 25, 2020  
INVENTOR(S) : Aharon Meir Eyal et al.

Page 1 of 1

It is certified that error appears in the above-identified patent and that said Letters Patent is hereby corrected as shown below:

On the Title Page

Item (30) Foreign Application Priority Data: insert the following:  
--Feb. 6, 2011 (WO).............................. PCT/IL2011/000130--

Signed and Sealed this  
Eleventh Day of May, 2021

Drew Hirshfeld  
*Performing the Functions and Duties of the*  
*Under Secretary of Commerce for Intellectual Property and*  
*Director of the United States Patent and Trademark Office*